(12) United States Patent
Schnetz et al.

(10) Patent No.: US 11,213,258 B2
(45) Date of Patent: Jan. 4, 2022

(54) VARIABLE INDEX FOR DETERMINING PATIENT STATUS

(71) Applicants: University of Pittsburgh—Of the Commonwealth System of Higher Education, Pittsburgh, PA (US); UPMC, Pittsburgh, PA (US)

(72) Inventors: Michael Schnetz, Pittsburgh, PA (US); Ata Kaynar, Pittsburgh, PA (US)

(73) Assignees: University of Pittsburgh—Of the Commonwealth System of Higher Education, Pittsburgh, PA (US); UPMC, Pittsburgh, PA (US)

( * ) Notice: Subject to any disclaimer, the term of this patent is extended or adjusted under 35 U.S.C. 154(b) by 374 days.

(21) Appl. No.: 16/057,401

(22) Filed: Aug. 7, 2018

(65) Prior Publication Data
US 2019/0046122 A1    Feb. 14, 2019

Related U.S. Application Data

(60) Provisional application No. 62/542,909, filed on Aug. 9, 2017.

(51) Int. Cl.
*A61B 5/05* (2021.01)
*A61B 5/00* (2006.01)
(Continued)

(52) U.S. Cl.
CPC .......... *A61B 5/7275* (2013.01); *A61B 5/0205* (2013.01); *A61B 5/4821* (2013.01);
(Continued)

(58) Field of Classification Search
None
See application file for complete search history.

(56) References Cited

U.S. PATENT DOCUMENTS

| 8,608,656 B2 | 12/2013 | Greenwald et al. |
| 10,751,004 B2 | 8/2020 | Al Hatib et al. |
| (Continued) | | |

OTHER PUBLICATIONS

Aranake, et al. "Minimum alveolar concentration: ongoing relevance and clinical utility." *Anaesthesia* 68, No. 5 (2013): 512-522.
(Continued)

*Primary Examiner* — Michael J D Abreu
(74) *Attorney, Agent, or Firm* — Klarquist Sparkman, LLP

(57) ABSTRACT

Methods are disclosed for determining a prognosis of a test patient following or during a surgical procedure. In some embodiments, the disclosed methods comprise forming a test data vector characterizing concurrent measures of mean arterial pressure (MAP), bispectral index (BIS), and standard minimum alveolar concentration (MAC) of the test patient from sequential time intervals during the surgical procedure. A K-means clustering procedure is performed on the test data vector and a plurality of reference data vectors characterizing concurrent MAP, BIS, and MAC measures for sequential time intervals during surgical procedures from reference patients with known clinical outcome. A prognosis of one or more post-surgical outcomes of the test patient is determined based on the known surgical outcome of reference patients in the cluster including the test data vector.

25 Claims, 29 Drawing Sheets
(20 of 29 Drawing Sheet(s) Filed in Color)

| Group_ID | Case_Count |
|---|---|
| Elevated_30D | 20 |
| Mixed_30D | 61 |
| Depressed_30D | 88 |
| Elevated_1yr | 75 |
| Mixed_1yr | 159 |
| Depressed_1yr | 116 |
| Elevated_2yr | 46 |
| Mixed_2yr | 90 |
| Depressed_2yr | 67 |
| Elevated_S | 1238 |
| Mixed_S | 2056 |
| Depressed_S | 1280 |
| Random sample | Same as non-random sample |

(51) Int. Cl.
 *A61B 5/0205* (2006.01)
 *A61B 5/08* (2006.01)
 *A61B 5/021* (2006.01)

(52) U.S. Cl.
 CPC .......... *A61B 5/7264* (2013.01); *A61B 5/0022* (2013.01); *A61B 5/021* (2013.01); *A61B 5/082* (2013.01); *A61B 5/7267* (2013.01); *A61B 5/7475* (2013.01); *A61B 2505/05* (2013.01)

(56) References Cited

U.S. PATENT DOCUMENTS

| | | | | |
|---|---|---|---|---|
| 2003/0233086 | A1* | 12/2003 | Burns, Jr. | A61K 31/06 604/512 |
| 2008/0021337 | A1* | 1/2008 | Li | A61N 1/3702 600/513 |
| 2010/0256463 | A1* | 10/2010 | Greenwald | A61B 5/7275 600/301 |
| 2012/0053433 | A1 | 3/2012 | Chamoun et al. | |
| 2013/0123298 | A1* | 5/2013 | Julia | A61K 31/137 514/304 |
| 2013/0262140 | A1* | 10/2013 | Friedlander | G16H 50/70 705/3 |
| 2014/0316792 | A1* | 10/2014 | Siddiqui | G16H 40/67 705/2 |
| 2017/0105672 | A1* | 4/2017 | Addison | A61B 5/14553 |
| 2018/0011116 | A1* | 1/2018 | Chapman | G01N 33/86 |

OTHER PUBLICATIONS

Kertai, et al. "Cumulative duration of "triple low" state of low blood pressure, low bispectral index, and low minimum alveolar concentration of volatile anesthesia is not associated with increased mortality." *Anesthesiology: The Journal of the American Society of Anesthesiologists* 121, No. 1 (2014): 18-28.

Liem, et al. "Anesthetic requirement is increased in redheads." *Anesthesiology: The Journal of the American Society of Anesthesiologists* 101, No. 2 (2004): 279-283.

Monk, et al. "Association between intraoperative hypotension and hypertension and 30-day postoperative mortality in noncardiac surgery." *The Journal of the American Society of Anesthesiologists* 123, No. 2 (2015): 307-319.

Nickalls, et al. "Age-related iso-MAC charts for isoflurane, sevoflurane and desflurane in man." *British Journal of Anaesthesia* 91, No. 2 (2003): 170-174.

Salmasi, et al. "Relationship between Intraoperative Hypotension, Defined by Either Reduction from Baseline or Absolute Thresholds, and Acute Kidney and Myocardial Injury after Noncardiac Surgerya Retrospective Cohort Analysis." *Anesthesiology: The Journal of the American Society of Anesthesiologists* 126, No. 1 (2017): 47-65.

Schnetz et al., "Triple Variable Index (TVI): A Novel Approach to Identify Postoperative Mortality." *American Society of Anesthesiologists Annual Meeting*, Oct. 22, 2016, Chicago, IL, USA (5 pages).

Sessler, et al. "Hospital stay and mortality are increased in patients having a "triple low" of low blood pressure, low bispectral index, and low minimum alveolar concentration of volatile anesthesia." *Anesthesiology: The Journal of the American Society of Anesthesiologists* 116, No. 6 (2012): 1195-1203.

Sun, et al. "Association of intraoperative hypotension with acute kidney injury after elective noncardiac surgery." *Anesthesiology: The Journal of the American Society of Anesthesiologists* 123, No. 3 (2015): 515-523.

Van Waes, et al. "Association between intraoperative hypotension and myocardial injury after vascular surgery." *Anesthesiology: The Journal of the American Society of Anesthesiologists* 124, No. 1 (2016): 35-44.

Vernooij, et al. "Different methods of modelling intraoperative hypotension and their association with postoperative complications in patients undergoing non-cardiac surgery." *British Journal of Anaesthesia* 120, No. 5 (2018): 1080-1089.

Walsh, et al. "Relationship between intraoperative mean arterial pressure and clinical outcomes after noncardiac surgerytoward an empirical definition of hypotension." Anesthesiology: *The Journal of the American Society of Anesthesiologists* 119, No. 3 (2013): 507-515.

Willingham, et al. "Concurrence of intraoperative hypotension, low minimum alveolar concentration, and low bispectral index is associated with postoperative death." *Anesthesiology: The Journal of the American Society of Anesthesiologists* 123, No. 4 (2015): 775-785.

Zeileis, et al. "zoo: S3 infrastructure for regular and irregular time series." *arXiv preprint math/0505527* (2005).

Schuetz et al., "The triple variable index combines information generated over time from common monitoring variables to identify patients expressing distinct patterns of intraoperative physiology," *BMC Medical Research Methodology* 19.1: Jan. 17, 2019 (14 pages).

* cited by examiner

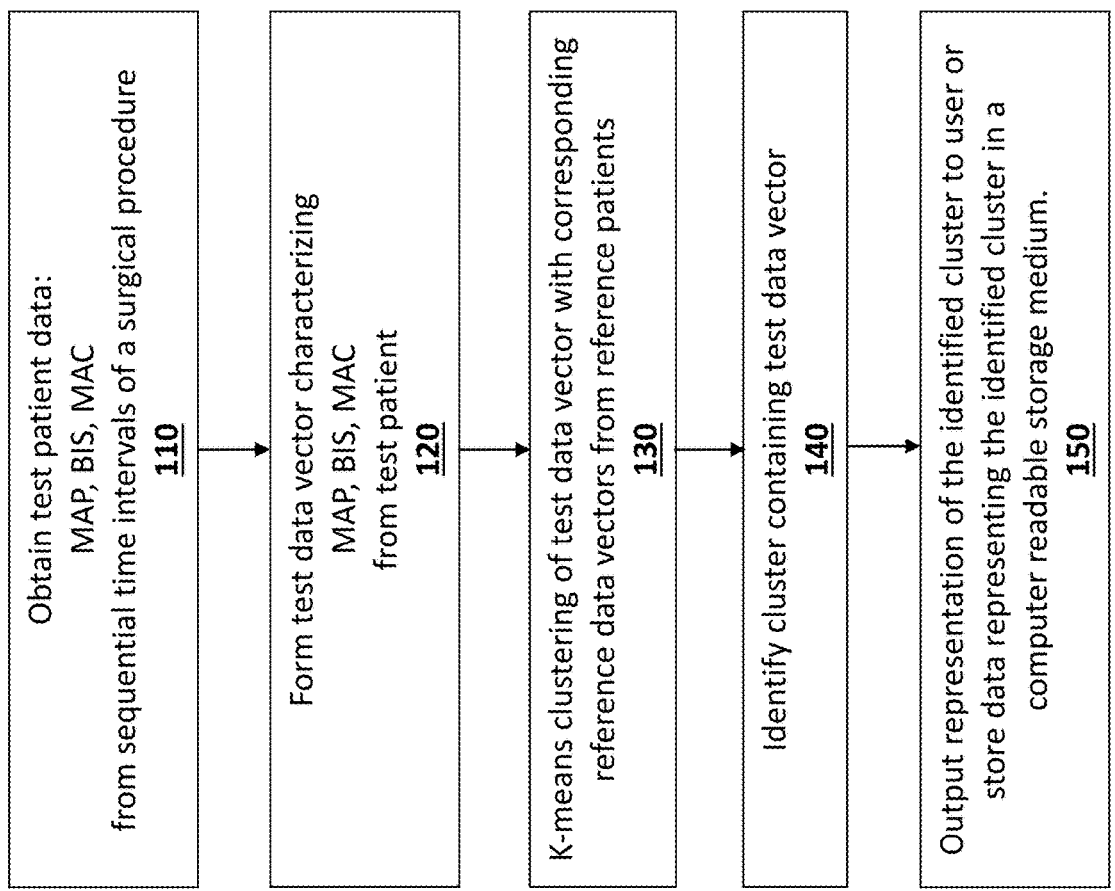

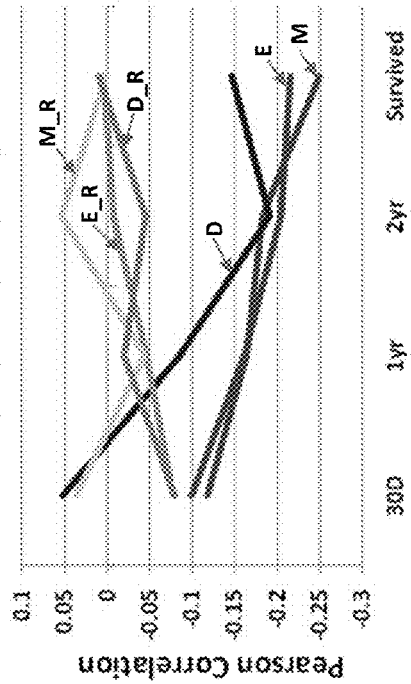
FIG. 8A
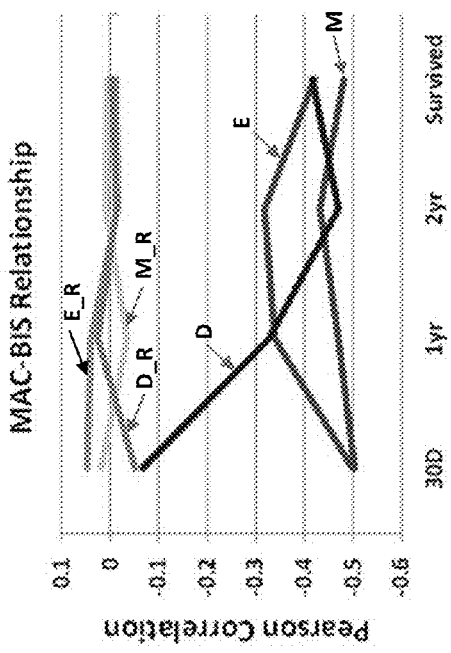
FIG. 8C
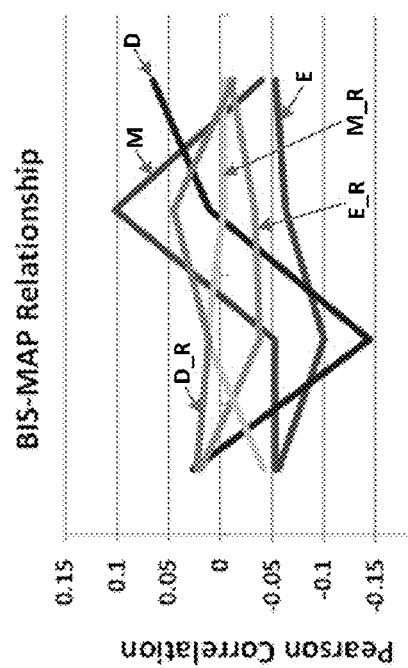
FIG. 8B
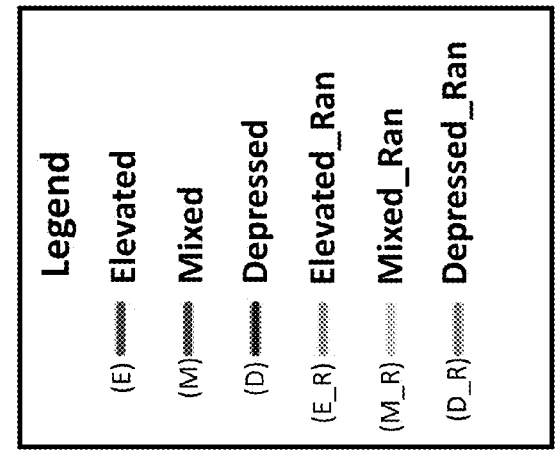

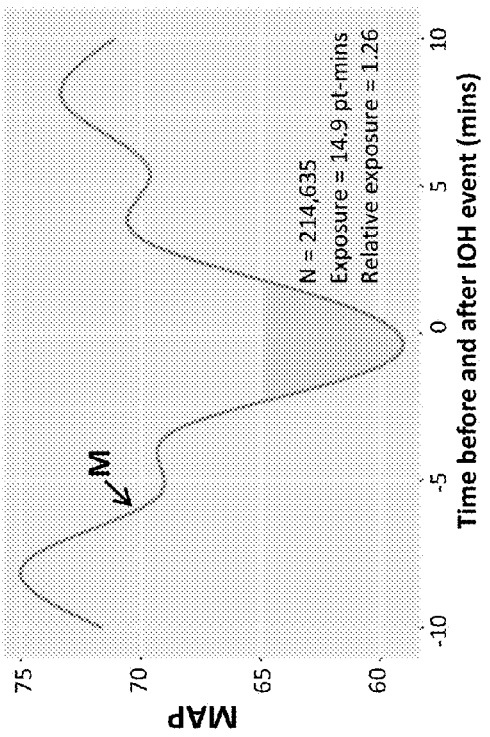
FIG. 19A Elevated
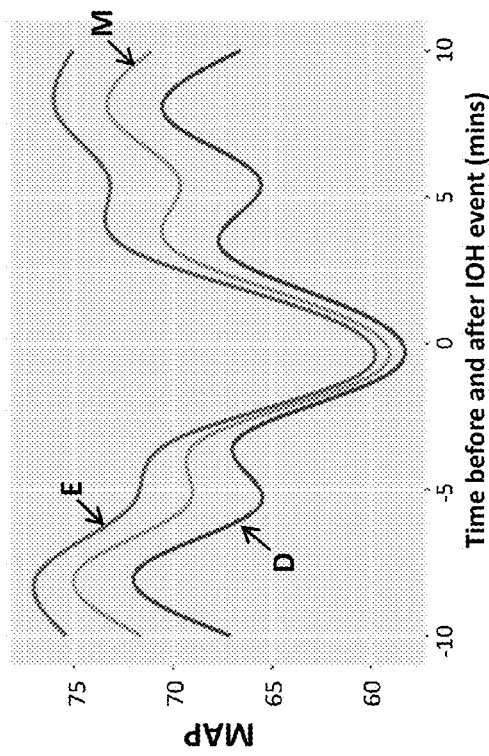
FIG. 19B Mixed
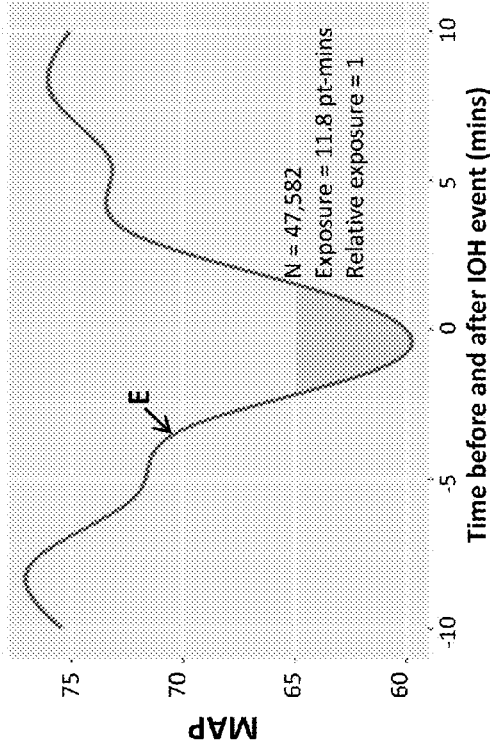
FIG. 19C Depressed
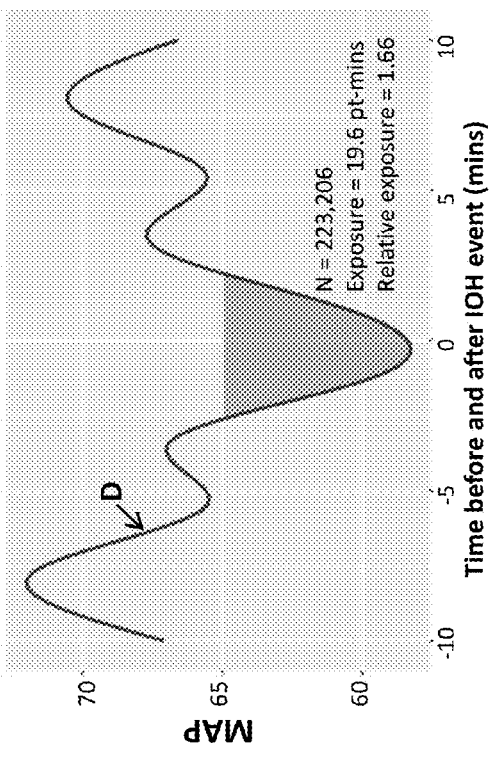
FIG. 19D All

VARIABLE INDEX FOR DETERMINING PATIENT STATUS

CROSS REFERENCE TO RELATED APPLICATIONS

The subject matter of this application is related to the subject matter of U.S. Provisional Application No. 62/542,909, filed Aug. 9, 2017, which is incorporated by reference in its entirety.

ACKNOWLEDGMENT OF GOVERNMENT SUPPORT

This invention was made with government support under grant numbers GM075770 and HG008540 awarded by the National Institutes of Health. The government has certain rights in the invention.

BACKGROUND

The perioperative period generates a tremendous volume of patient-specific data during each surgical encounter. Data are diverse and multi-dimensional as they are collected across distinct care settings (e.g. operating room (OR), post-anesthesia care unit (PACU), intensive care unit (ICU)) and time. Preferably, these data would be harnessed to provide real-time assessment and evidence-based treatment strategies to patients as they progresses through the perioperative period. For example, improving disease-specific guideline adherence during preoperative evaluation or leveraging physiologic responses that occur during surgery to better understand how adverse events occur post-surgically.

Strategies commonly employed to better understand the perioperative experience are ill equipped in both design and focus to meet such data utilization needs. Established methods are limited in scope (e.g. risk factor identification), require large patient populations and time to execute, incorporate subjective assessments that vary between clinicians, cannot be applied to individual patients, and do not consider the dynamic nature of changing patient populations and practice patterns that exist in health care systems and treatment centers.

SUMMARY

This disclosure provides novel methods for integration of heterogeneous patient monitoring data obtained during a surgical procedure on a test patient to provide improved analysis of homeostatic capacity and patient outcome during and following surgery, such as to monitor patient homeostasis during the procedure (for example, to monitor the risk of an intraoperative hypotension (IOH) event) and/or to determine a prognosis for the patient following the procedure. Surprisingly, and despite considerable patient population diversity, the disclosed methods successfully characterize intra- and post-surgical outcomes and patient homeostatic capacity across a wide range of surgical procedures and patient variables.

In some embodiments, a computer-implemented method is provided, the method comprising obtaining concurrent measures of mean arterial pressure (MAP), bispectral index (BIS), and standard minimum alveolar concentration (MAC) of the test patient from sequential time intervals (such as every five minutes) during the surgical procedure. The surgical procedure comprises administration of an inhalation anesthetic to the test patient. A test data vector is formed that characterizes the concurrent MAP, BIS, and MAC measures for the sequential time intervals during the surgical procedure. A K-means clustering procedure is performed to cluster the test data vector with a plurality of reference data vectors. The reference data vectors characterize concurrent MAP, BIS, and MAC measures for sequential time intervals during surgical procedures from reference patients. Following the clustering procedure, a cluster including the test data vector is identified, and a representation of the identified cluster is outputted to user (for example, in real time), and/or data representing the identified cluster is stored in a computer readable storage medium.

In some embodiments, the disclosed method comprises determining a prognosis of a test patient during or following the surgical procedure. In some such embodiments, the reference data vectors characterize concurrent MAP, MAC, and BIS measures for sequential time intervals during surgical procedures of reference patients with a known physiological state during and/or following the procedure post-surgical outcome; and the method further comprises determining a prognosis of the test patient based on the known physiological state during and/or following the procedure of the reference patients in the cluster including the test data vector. The prognosis can be, for example, a likelihood of one or more patient outcomes, and/or a likelihood of a level of homeostatic capacity of the patient during or following surgery.

In some embodiments, the disclosed method comprises determining a prognosis of a test patient during or following the surgical procedure. In some such embodiments, the reference data vectors characterize concurrent MAP, MAC, and BIS measures for sequential time intervals during surgical procedures of reference patients with a known post-surgical outcome; and the method further comprises determining a prognosis of the test patient based on the known post-surgical outcome of reference patients in the cluster including the test data vector. A prognosis of any relevant post-surgical outcome (or outcomes) can be determined using the disclosed method. For example, in some embodiments, the prognosis comprises a likelihood of one or more post-surgical outcomes comprising one or more of infection, pain, nausea, vomiting, delirium, post-surgical complications, acute kidney injury, respiratory failure, acute anemia, thrombocytopenia, heart failure, coagulopathy, acidosis, malnutrition, sepsis, shock, acute coronary events (such as myocardial injury and infarction), hospital stay length of greater than average, and death.

In some embodiments, the disclosed method comprises monitoring a risk of an intraoperative hypotension event (such as a MAP measurement of below 65 mmHg) in the test patient during a surgical procedure. In some such embodiments, the reference patients are patients who experienced zero, one, or multiple intraoperative hypotension events during a surgical procedure comprising administration of an inhalation anesthetic, and the K-means clustering procedure provides clusters of data vectors characterizing relative high, medium, and low concurrent MAP, MAC, and BIS measures. The representation of the identified cluster indicates whether the test data vector clusters with the cluster of reference data vectors characterizing the relative high, medium, or low concurrent MAP, MAC, and BIS measures. In some embodiments, the representation of the identified cluster is outputted to a user in real time. In some embodiments, clustering of the test data vector with the cluster of reference data vectors characterizing the relative high concurrent MAP, MAC, and BIS measures indicates a low risk of an intraoperative hypotension event. In some embodiments, clustering of the test data vector with the cluster of reference data vectors characterizing the relative low concurrent MAP, MAC, and BIS measures indicates a high risk of an intraoperative hypotension event. In some embodiments, the method further comprises preemptively treating the patient for hypotension to reduce the risk of the intraoperative hypotension event if the test data vector clusters with the cluster of reference data vectors characterizing the relative low concurrent MAP, MAC, and BIS measures.

In some embodiments, forming the test data vector comprises normalizing each of the MAP, BIS, and MAC measures of the test patient from the sequential time intervals, summing the normalized MAP, BIS, and MAC measures from each time interval, and forming the test data vector from the respective sums of normalized MAP, BIS, and MAC measures for the sequential time intervals. In some embodiments, obtaining the MAC measures comprises obtaining measures of end-tidal concentration of inhalation anesthetics of the test patient from the sequential time intervals during the surgical procedure. In some embodiments, the MAP, BIS, and MAC measures are normalized by calculating a Z-score for each individual measurement relative to respective reference MAP, BIS, and MAC values.

The K-means clustering procedure comprises a suitable number of centroids (such as three or five centroids) and generates a suitable number of clusters of data vectors characterizing the concurrent MAP, BIS, and MAC measures, one of which comprises the test data vector.

In some embodiments, the reference data vectors characterize concurrent MAP, BIS, and MAC measures for sequential time intervals during surgical procedures from reference patients (such as patients with a known post-surgical outcome or a known incidence of IOH) that are from the same hospital system as that performing the surgical procedure on the test patient. In additional embodiments, the reference data vectors characterize MAP, BIS, and MAC measures from reference patients with the same surgical procedure as that of the test patient. Non-limiting examples of surgical procedures for which the disclosed methods can be applied include outpatient/ambulatory surgical procedures, ear-nose-throat surgery, trauma surgery, urological surgery, neurosurgery, orthopedic surgery, vascular surgery, thoracic surgery, pediatric surgery, cardiac surgery, Ob-Gyn surgery, ophthalmologic surgery, transplant surgery, general surgery, plastic surgery, colon and rectal surgery, gynecologic oncology surgery, oral and maxillofacial surgery, critical care procedures, where inhalation anesthetics are used, and dental surgical services.

In several embodiments, the method comprises outputting the determined prognosis to a user, generating a generating a post-surgical report comprising the prognosis, outputting the post-surgical report to a user, and/or storing data representing the prognosis, or the port-operative report in a computer-readable storage medium. In several embodiments, the method comprises receiving data representing the prognosis following the surgical procedure for the test patient via a computer network.

In additional embodiments, computer systems, and computer readable media are provided that are configured to execute instructions to perform a method as described herein.

The foregoing and other features and advantages of the invention will become more apparent from the following detailed description of several embodiments which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A and 1B are flow charts depicting an example method for interrogating measures of MAP, MAC, and BIS of a test patient during or following surgery using and a K-means clustering procedure (FIG. 1A) and normalizing the MAP, BIS, and MAC measures to form a test data vector (FIG. 1B), according to disclosed technology.

FIGS. 8A-8C: MAC-BIS, MAC-MAP and BIS-MAP relationships were assessed in each TVI pattern-post-surgical mortality group from FIG. 3 using Pearson correlation. A control correlation was calculated for each experimental group by randomly ordering variable pairs before calculating the correlation. Experimental correlations are denoted with dark lines in each plot, while associated random controls are light lines of the same color.

FIGS. 19A-19D: Models of individual intraoperative hypotension (IOH) events for each TVI expression pattern. The x-axis is the relative time before and after an IOH occurred (time=0 minutes). The total number of IOH events analyzed for each model is shown. Both absolute and relative exposures, denoted by shaded areas below 65 mmHg in each curve, were calculated.

DETAILED DESCRIPTION

I. Introduction

Figure 1B:
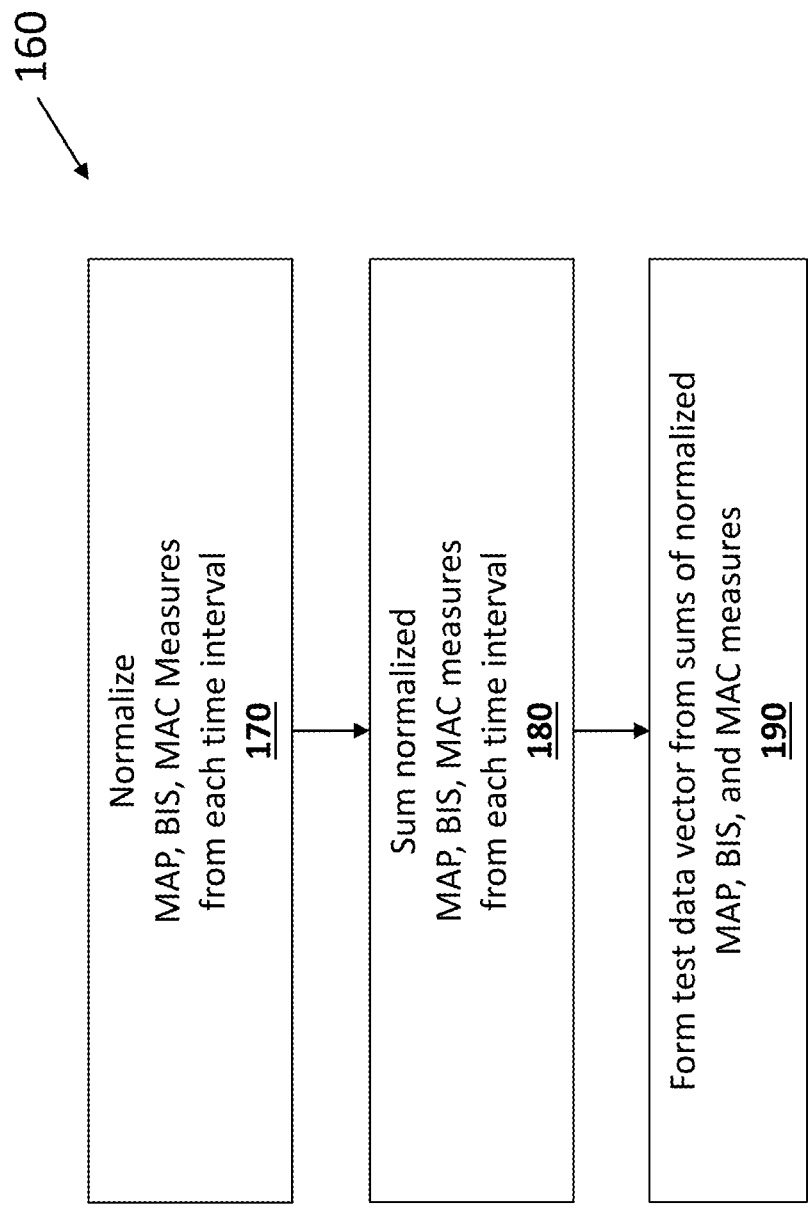

Presented herein are novel approaches to simultaneously integrate cardiovascular and neurologic function data in response to anesthesia and surgery to determine homeostatic capacity and patient outcome during and following surgery. An example is provided, termed the Triple Variable Index (TVI). The TVI has several features that distinguish it from prior attempts to integrate patient state data during surgery, such as Triple Low State identification or other markers of patient physiology, such as ASA physical status, used in clinical practice. TVI is objectively derived from patient-specific physiologic data and may be generated at any time when mean arterial pressure (MAP), Bispectral Index (BIS) and minimum alveolar concentration (MAC) of inhalation anesthetic data are concurrently available. The TVI is mapped moment-to-moment for individual patients. A map of TVI signal over time is used in total, without arbitrary thresholds, to inform patient physiologic status. By incorporating information from multiple variables over time, TVI reveals distinct patterns of organ system function that define specific states of intraoperative physiology characterized by a host of patient and procedure-related factors. Identified states exhibit both functional and clinical features including patient-specificity, organ system regulation/dysregulation, perioperative disease burden, and risk of death following surgery.

II. Terms

Unless otherwise noted, technical terms are used according to conventional usage. In case of conflict, the present specification, including explanations of terms, will control. To facilitate review of the various embodiments, the following explanations of terms are provided:

About: Plus or minus 5% from a set amount. For example, "about 5" refers to 4.75 to 5.25. A ratio of "about 5:1" refers to a ratio of from 4.75:1 to 5.25:1.

Bispectral index (BIS): A measure for assessing the level of consciousness in a patient undergoing anesthesia. BIS is a derived variable of the EEG that provides a measure of the consistency of phase and power relationships among the various frequencies of the EEG. The BIS describes the complex EEG pattern as a single variable which has been used for control of anesthesia and approved by FDA for anesthetic depth monitoring. BIS and its use is described, for example, in Myles et al. ("Bispectral Index monitoring to prevent awareness during anaesthesia: the B-Aware randomised controlled trial," Lancet 2004; 363:1757-1763, which is incorporated by reference herein).

Cluster: A cluster is a group of physiological measures (such as MAP, BIS, and MAC measures) having at least one similar property. In this description, physiological measures are described by data vectors, and a measure of similarity can be defined on the data vectors. Generally, on average, a vector of a cluster is more similar to other vectors in its own cluster than to vectors outside its cluster. Generally, the measure of similarity can be different for different clusters.

Data Vector: A data vector is a finite ordered collection of numerical quantities. A data vector having M components is dubbed an M-dimensional data vector and has a magnitude and direction in an M-dimensional space dubbed the vector space, except that no direction is defined for a data vector having zero magnitude. The magnitude of the data vector is its norm.

One of ordinary skill will recognize that the use of a data vector in this disclosure can offer convenient conceptualization but is not a requirement. The data vectors described herein could equivalently be cast in terms of other data structures, singly or in combination, including without limitation arrays, graphs, hashes, lists, tables, or trees, all of which are included within the scope of the disclosed technologies.

Inhalation anesthetic: A drug administered via an inhalation route to an individual leading to reduced sensation of pain. Inhalation anesthetics are typically administered prior to and during surgical procedures to reduce or mask the pain of the surgical procedure. In some embodiments, the inhalation anesthetic is a general anesthetic that induces a loss of consciousness. Non-limiting examples of inhalation anesthetics include isoflurane, desflurane, sevoflurane, and nitrous oxide.

Intraoperative hypotension (IOH): An occurrence of a MAP measurement below 65 mmHg in a patient during surgery involving administration of an inhalation anesthetic.

K-means clustering: An unsupervised clustering technique for partitioning a dataset of numeric vectors, where each numeric vector has dimensionality M and there are N such vectors. K-means clustering aims to partition the N vectors into K clusters in which each vector belongs to the nearest cluster. The value, K, refers to an input parameter of the algorithm that determines the number of such clusters that will be produced at completion of the clustering analysis. In general, K-means, from a given starting point, finds a locally optimum way to cluster the dataset into K partitions so as to minimize the average difference between the mean of each cluster (cluster centroid) and every member of that cluster. This difference is typically measured by some distance metric, such as Euclidean distance.

In several disclosed embodiments, the N vectors represent MAP, BIS, and MAC measures for the sequential time intervals during the surgical procedure for test patients, and for reference patients with known outcome following a surgical procedure and/or known physiological state during the procedure (such as known incidence of IOH). In such embodiments, dimensionality M refers to MAP, BIS and MAC measures at respective time intervals.

Mean arterial pressure (MAP): The average arterial pressure during a single cardiac cycle in an individual.

Minimum alveolar concentration (MAC): The alveolar (or end-expiratory) concentration of an inhaled anesthetic at which 50% of patients will not show a motor response to a standardized surgical incision. In situations where the patient is administered more than one inhaled anesthetic during a surgical procedure, the MAC measure typically refers to the sum of MAC values representing all inhaled anesthetics at a given interval in time during the surgery.

Normalization: Normalization refers to a process of balancing components (e.g., MAP, BIS, and MAC measures) relative to a reference value. Normalization coefficients provide weights to the different components, and can be used, for example, when making multi-dimensional calculations (e.g. of MAP, BIS, and MAC) with one, two, or more data vectors.

Patient: Living multi-cellular vertebrate organisms, a category that includes both human and non-human mammals. In some examples, a patient is human surgical patient.

Post-surgical outcome: A clinical outcome for a patient in a pre-determined period following a surgical procedure. The pre-determined time period is not more than one year and can begin immediately following surgery. In some examples, the pre-determined time period can be within one day, one week, one month, six months, or one year following surgery. Non-limiting examples of post-surgical outcomes that can be interrogated using the methods disclosed herein include development of a post-surgical infection, development or severity of post-surgical pain, time to achieve adequate level of post-surgical pain, development or severity of post-surgical nausea and/or vomiting, development or severity of post-surgical delirium, development or severity of post-surgical complications, death within a selected time period following surgery (such as within one day, within one week, within one month or within one year), acute kidney injury, respiratory failure, acute anemia, thrombocytopenia, heart failure, coagulopathy, acidosis, malnutrition, sepsis, shock, and post-surgical hospital stay length of greater than average time.

Prognosis: The likelihood that a patient will have a particular post-surgical outcome or level of homeostatic capacity (for example, an assessment of how well a patient can maintain homeostasis in the context of a physical/psychological challenge) following or during a surgical procedure, whether positive or negative. The predictive methods of can be used clinically to make treatment decisions by choosing the most appropriate treatment modalities for any particular patient and are valuable tools for predicting if a patient is likely to respond favorably to a treatment regimen.

As will be understood by those skilled in the art, the prediction, although preferred to be, need not be correct for 100% of the patients to be evaluated. However, a statistically significant portion of patients can be identified as having an increased probability of having a given outcome. Whether a patient is statistically significant can be determined by using various well known statistic evaluation tools, for example, determination of confidence intervals, p-value determination, cross-validated classification rates and the like. Preferred confidence intervals are at least 50%, at least 60%, at least 70%, at least 80%, at least 90% or at least 95%. The p-values are, preferably, 0.01, 0.005 or lower.

III. Methods

FIG. 1 is a flowchart 100 depicting an example computer-implemented method for interrogating physiological measures of a test patient during or following surgery using measures of MAP, MAC, and BIS and a K-means clustering procedure, according to disclosed technology.

At process block 110, MAP, MAC, and BIS measures are obtained by suitable means, for example, from data obtained when monitoring a patient in surgery. The MAP, BIS, and MAP measures are taken concurrently from sequential time intervals of the surgical procedure. For concurrent MAP, BIS, and MAC measures, the measures do not need to have been taken at exactly the same time falling within a particular time interval, as long each measure is taken during the allotted time interval for that concurrent measurement. In a non-limiting example, concurrent MAP, BIS, and MAC measures for every 5 minute time interval during the surgical procedure are obtained for analysis. In some examples, one or more of the MAP, BIS, and MAC measures for each time interval can be an average measures of the MAP, BIS, or MAC during the respective time interval. In some embodiments, the concurrent measures of MAP, MAC, and BIS are taken over at least 20 minutes (such as at least 30 minutes, at least 45 minutes, at least one hour or the time of the compete surgery) during the time that an inhalation anesthetic is administered to the patient during the surgical procedure.

The surgical procedure comprises administration of an inhalation anesthetic to the test patient. Non-limiting examples of such procedures include surgical procedures pertaining to ear-nose-throat, trauma, urological, neurosurgical, orthopedic, vascular, thoracic, pediatric, cardiac, OB-GYN, ophthalmologic, transplant surgery, general surgery, plastic surgery, colon and rectal surgery, gynecologic oncology surgery, oral and maxillofacial surgery, oral and maxillofacial surgery, critical care procedures, where inhalation anesthetics are used, and dental surgical services, and dental surgical services.

Non-limiting examples of inhalation anesthetics for use in the surgical procedure include halothane, isoflurane, desflurane, sevoflurane, nitrous oxide, and combinations thereof. In some embodiments, the inhalation anesthetic is administered to the test patient as a general anesthetic. In some such embodiments, the concurrent MAP, BIS, and MAC measures are from time intervals during the surgical procedure when the test patient was unconscious due to the inhalation anesthetic.

At process block 120, a test data vector is formed. The test data vector characterizes the concurrent MAP, BIS, and MAC measures for the sequential time periods of the surgery of the test patient that are obtained at step 110. For example, the test data vector can have three components for each time interval, each component characterizing one of the concurrent MAP, BIS, and MAC measures at that time interval. In additional embodiments, the data vector can have a single component for each time interval that characterizes the MAP, BIS, and MAC measures. In some embodiments, the MAP, BIS, and MAC measures are normalized prior to formation of the test data vector. For example, by calculating a Z-score for each individual measurement relative to respective reference MAP, BIS, and MAC values, as discussed in Example 1.

FIG. 1B depicts an exemplary process 160 for forming the test data vector comprising normalizing the MAP, BIS, and MAC measures of the test patient from the sequential time intervals. At process block 170, the MAP, BIS, and MAC measures from each time interval are normalized prior to formation of the test data vector. For example, by calculating a Z-score for each individual measurement relative to respective reference MAP, BIS, and MAC values, as discussed in Example 1. At process block 180, the normalized MAP, BIS, and MAC measures from each time interval are summed to produce a single value representing a combination of the MAP, BIS, and MAC measures at each time interval. At process block 190, the test data vector is formed from the summed MAP, BIS, and MAC measures from each time interval. Thus, the test data vector formed by exemplary process 200 provides a profile of the MAP, BIS, and MAC measures over the course of the surgical procedure.

Returning to exemplary process 100, at process block 130, a K-means clustering analysis of the test data vector with a plurality of reference data vectors is performed. By classifying the test data vector and the plurality of reference data vectors using a K-means clustering procedure, the test data vector is partitioned based on similarity with a cluster of reference data vectors from the plurality.

The reference data vectors in the plurality characterize concurrent MAP, BIS, and MAC measures for sequential time intervals during surgical procedures from a plurality of reference patients, for example patients with a known post-surgical outcome or known physiological state during or following procedure. The plurality of reference patients can be, for example, one or more of: surgical patients who have undergone similar (or the same) surgical procedure as that of the test patient, surgical patients who have undergone surgery at the same hospital system as that of the test patient, surgical patients who have undergone surgery at the same surgical center as that of the test patient. In some embodiments, the plurality of reference patients is a plurality of surgical patients who have undergone the same surgical procedure at the same surgical center as the test patient. In some embodiments, the reference patients are patients who experienced zero, one, or multiple intraoperative hypotension events during a surgical procedure comprising administration of an inhalation anesthetic.

K-means clustering is a centroid-initiated clustering procedure. The K-means clustering procedure utilized in the disclosed methods comprises at least three centroids (such as 3, 4, 5, 6, 7, 8, 9, 10, or more centroids) resulting in at least three clusters of data vectors characterizing concurrent MAP, BIS, and MAC measures for sequential time intervals during the surgical procedure, with one of the clusters comprising the test data vector. In some embodiments, the K-means clustering procedure comprises three centroids resulting in three clusters of data vectors characterizing concurrent MAP, BIS, and MAC measures for sequential time intervals during the surgical procedure, with one of the clusters comprising the test data vector.

In some embodiments, the K-means clustering procedure comprises five centroids resulting in five clusters of data vectors characterizing concurrent MAP, BIS, and MAC measures for sequential time intervals during the surgical procedure, with one of the clusters comprising the test data vector.

At process block 140, the cluster containing the test data vector is identified. This cluster contains the test data vector as well as reference data vectors partitioned in the cluster based on similarity with the test data vector.

At process block 150, a representation of the identified cluster is outputted to a user or data representing the identified cluster is stored in a computer readable storage medium. For example, the representation of the identified cluster can be outputted to a user (such as a treating surgeon) in real-time, included in a post-surgical report, stored in one or more computer-readable storage media, or outputted to a secondary computing system or network.

In some embodiments, the reference data vectors characterize concurrent MAP, MAC, and BIS measures for sequential time intervals during surgical procedures of reference patients with a known physiological state during and/or following the procedure; and the method further comprises determining a prognosis of the test patient based on the known physiological state of the reference patients in the cluster including the test data vector.

In some embodiments, the method is used to monitor a risk of an intraoperative hypotension event in the test patient during the surgical procedure. For example, the intraoperative hypotension event can be a MAP measurement of below 65 (such as below 60 or below 55) mmHg. In some such embodiments, the reference patients are patients who experienced zero, one, or multiple intraoperative hypotension events during a surgical procedure comprising administration of an inhalation anesthetic and the representation of the identified cluster indicates whether the test data vector clusters with the cluster of reference data vectors characterizing the relative (such as high, medium, or low) concurrent MAP, MAC, and BIS measures. For example, the reference patients are patients who experienced zero, one, or multiple intraoperative hypotension events during a surgical procedure comprising administration of an inhalation anesthetic, the K-means clustering procedure provides clusters of data vectors characterizing relative high, medium, and low concurrent MAP, MAC, and BIS measures; and the representation of the identified cluster indicates whether the test data vector clusters with the cluster of reference data vectors characterizing the relative (such as high, medium, or low) concurrent MAP, MAC, and BIS measures. In several such embodiments, clustering of the test data vector with the cluster of reference data vectors characterizing the relative high concurrent MAP, MAC, and BIS measures indicates a low risk of an intraoperative hypotension event; and clustering of the test data vector with the cluster of reference data vectors characterizing the relative low concurrent MAP, MAC, and BIS measures indicates a high risk of an intraoperative hypotension event. Some embodiments, further comprise preemptively treating the patient for hypotension to reduce the risk of the intraoperative hypotension event if the test data vector clusters with the cluster of reference data vectors characterizing the relative low concurrent MAP, MAC, and BIS measures.

In some embodiments, the reference data vectors characterize concurrent MAP, MAC, and BIS measures for sequential time intervals during surgical procedures of reference patients with a known post-surgical outcome; and the method further comprises determining a prognosis of the test patient based on the known post-surgical outcome of reference patients in the cluster including the test data vector. The prognosis following the surgical procedure for the test patient can be determined based on the similarity of the reference and test data vectors in the resulting cluster.

The prognosis following the surgical procedure for the test patient is determined based on the known post-surgical outcome of reference patients in the cluster including the test data vector. Thus, the prognosis for the test patient is based on the actual post-surgical outcome for reference patients with data vectors characterizing concurrent MAC, BIS, and MAP measures over the course of surgery that are similar to the test data vectors for the test patient. The prognosis provides an indication of the likelihood that a patient will have a particular post-surgical outcome or level of homeostatic capacity following the surgical procedure, whether positive or negative.

The prognosis can characterize a likelihood of any suitable post-surgical outcome, and can characterize the likelihood of one or more such outcomes. Non-limiting examples of post-surgical outcomes (such as an outcome within one day, one week, 30 days, 6 months, or one year from the time of surgery) include likelihood of development of a post-surgical infection, likelihood of post-surgical pain, likelihood of time to achieve adequate level of post-surgical pain, likelihood of post-surgical nausea and vomiting, likelihood of post-surgical delirium, likelihood of post-surgical complications, likelihood of acute kidney injury, likelihood of respiratory failure, likelihood of acute anemia, likelihood of thrombocytopenia, likelihood of heart failure, likelihood of coagulopathy, likelihood of acidosis, likelihood of malnutrition, likelihood of sepsis, likelihood of acute coronary events (such as myocardial injury and infarction), likelihood of shock, likelihood of death within a selected time period following surgery, likelihood of post-surgical hospital stay length of greater than average for similar procedures in similar hospital settings, and degree of patient satisfaction. In some embodiments, the prognosis provides a likelihood of death within a pre-defined time period, such as within 30 days, 6 months, or one year from the time of surgery. The prognosis is based on the actual death rate during the predefined time period for the reference patients characterized by the reference data vectors that partition into the same cluster as that test data vector characterizing the test patient.

In some embodiments, the prognosis is a likelihood of a particular post-surgical outcome relative to a suitable control, such as the actual incidence rate of the particular post-surgical outcome in the plurality of reference patients. As discussed above, the plurality of reference patients can be, for example, one or more of: surgical patients who have undergone similar (or the same) post-surgical procedure as that of the test patient, surgical patients who have undergone surgery at the same hospital system as that of the test patient, surgical patients who have undergone surgery at the same surgical center as that of the test patient. In some embodiments, the reference population is a plurality of surgical patients who have undergone the same surgical procedure at the same surgical center as the test patient.

In an example, if the test data vector partitions into a cluster of reference data vectors from reference patients with increased occurrence rate (for example, at least a 50% increase or at least a 100% increase) of a particular post-surgical outcome relative to the average rate of the post-surgical outcome for the reference patients in the plurality of reference patients, then the prognosis for the test patient comprises an increased likelihood of the post-surgical outcome relative to the average rate of the post-surgical outcome for the reference patients in the plurality of reference patients. In an example, if the test data vector partitions into a cluster of reference data vectors from reference patients with reduced occurrence rate (for example, at least a 50% decrease or at least a 25% decrease) of a particular post-surgical outcome relative to the average rate of the post-surgical outcome for the reference patients in the plurality of reference patients, then the prognosis for the test patient comprises a reduced likelihood of the post-surgical outcome relative to the average rate of the post-surgical outcome for the reference patients in the plurality of reference patients. In another example, if the test data vector partitions into a cluster of reference data vectors from reference patients with an average occurrence rate (for example, within 30%, such as within 20%, or within 10%) of a particular post-surgical outcome relative to the average rate of the post-surgical outcome for the reference patients in the plurality of reference patients, then the prognosis for the test patient comprises an average likelihood of the post-surgical outcome relative to the average rate of the post-surgical outcome for the reference patients in the plurality of reference patients.

In an example, if the test data vector partitions into a cluster of reference data vectors from reference patients with an increased occurrence (for example, at least a 50% increase or at least a 100% increase) of post-surgical infection relative to the average rate of post-surgical infection for the reference patients in the plurality of reference patients, then the prognosis for the test patient comprises an increased likelihood of post-surgical infection relative to the average rate of post-surgical infection for the reference patients in the plurality of reference patients. In another example, if the test data vector partitions into a cluster of reference data vectors from reference patients with a reduced occurrence (for example, at least a 25% decrease or at least a 50% decrease) of post-surgical infection relative to the average rate of post-surgical infection for the reference patients in the plurality of reference patients, then the prognosis for the test patient comprises an decreased likelihood of post-surgical infection average rate of post-surgical infection for the reference patients in the plurality of reference patients.

In an example, if the test data vector partitions into a cluster of reference data vectors from reference patients with an increased post-surgical hospital stay length (for example, at least a 50% increase or at least a 100% increase) relative to the average post-surgical hospital stay length for the reference patients in the plurality of reference patients, then the prognosis for the test patient comprises a likelihood of post-surgical hospital stay that is longer than average post-surgical hospital stay length for the reference patients in the plurality of reference patients. In another example, if the test data vector partitions into a cluster of reference data vectors from reference patients with an reduced post-surgical hospital stay length (for example, at least a 50% decrease or at least a 25% decrease) relative to the average post-surgical hospital stay length for the reference patients in the plurality of reference patients, then the prognosis for the test patient comprises a likelihood of post-surgical hospital stay that is shorter than the average post-surgical hospital stay length for the reference patients in the plurality of reference patients.

In some embodiments, the prognosis provides a likelihood of death within a pre-defined time period, such as within 30 days, 6 months, or one year from the time of surgery. The prognosis is based on the actual death rate during the predefined time period for the reference patients characterized by the reference data vectors that partition into the same cluster as that test data vector characterizing the test patient.

The methods described herein objectively measure patient physiology, and the prognosis of the test patient determined using such methods can serve as a general assessment of homeostatic capacity of the test patient. Thus, the determined prognosis can provide an indication of the likelihood of how well a patient can maintain homeostasis in the context of a physical/psychological challenge. This prognosis can be used, for example, to define how patients differentially respond to physical and psychological challenges during surgery and in the post-surgical period, and correspondingly customize their care to optimize outcome.

The determined prognosis (or data representing the determined prognosis) can be, for example, outputted to a user, included in a in a post-surgical report, stored in one or more computer-readable storage media, or outputted to a secondary computing system or network. In some embodiments, the determined prognosis is included in a post-surgical report, which, for example, can be outputted to a user, stored in one or more computer-readable storage media, or outputted to a secondary computing system or network. In some embodiments, the method further comprises receiving data representing the prognosis following the surgical procedure for the test patient via a computer network.

The prognosis can be used by a treating physician to make treatment decisions by choosing the most appropriate treatment modalities for any particular patient. As will be understood by those skilled in the art, the prognosis need not be correct for 100% of the patients to be evaluated. However, a statistically significant portion of patients can be identified as having an increased probability of having a given outcome.

The description of flowcharts 100 and 160 above encompasses numerous variants. With this disclosure in hand, one of ordinary skill will appreciate that many additional variations are possible within the scope of disclosed technologies, as described herein.

Additional Embodiments

In an alternative embodiment, the computer-implemented method as discussed above can be performed using measures of MAC and MAP (instead of MAP, MAC, and BIS). As in the method described above, the MAP and MAC measures are taken concurrently from sequential time intervals of the surgical procedure, and a test data vector is formed that characterizes the concurrent MAP and MAC measures for the sequential time periods of the surgery of the test patient. Next, a K-means clustering analysis of the test data vector with a plurality of reference data vectors is performed. The reference data vectors in the plurality characterize concurrent MAP and MAC measures for sequential time intervals during surgical procedures from a plurality of reference patients, such as those with a known post-surgical outcome. By classifying the test data vector and the plurality of reference data vectors using a K-means clustering procedure, the test data vector is partitioned based on similarity with a cluster of reference data vectors from the plurality.

In some such embodiments, the reference data vectors characterize concurrent MAP and MAC measures for sequential time intervals during surgical procedures of reference patients with a known physiological state during and/or following the procedure; and the method further comprises determining a prognosis of the test patient based on the known physiological state of the reference patients in the cluster including the test data vector. The prognosis following the surgical procedure for the test patient can be determined based on the similarity of the reference and test data vectors in the resulting cluster. The prognosis provides an indication of the likelihood that a patient will have a particular physiological state (such as an increased risk of IOH) or post-surgical outcome following the surgical procedure, whether positive or negative. The prognosis can be determined, assessed, and utilized as discussed above for methods involving MAP, MAC, and BIS measures.

In an alternative embodiment, the computer-implemented method as discussed above can be performed using measures of MAC and BIS (instead of MAP, MAC, and BIS). As in the method described above, the MAP and BIS measures are taken concurrently from sequential time intervals of the surgical procedure, and a test data vector is formed that characterizes the concurrent MAC and BIS measures for the sequential time periods of the surgery of the test patient. Next, a K-means clustering analysis of the test data vector with a plurality of reference data vectors is performed. The reference data vectors in the plurality characterize concurrent MAC and BIS measures for sequential time intervals during surgical procedures from a plurality of reference patients, such as those with a known post-surgical outcome. By classifying the test data vector and the plurality of reference data vectors using a K-means clustering procedure, the test data vector is partitioned based on similarity with a cluster of reference data vectors from the plurality. In some such embodiments, the reference data vectors characterize concurrent MAC and BIS measures for sequential time intervals during surgical procedures of reference patients with a known physiological state during and/or following the procedure; and the method further comprises determining a prognosis of the test patient based on the known physiological state of the reference patients in the cluster including the test data vector. The prognosis following the surgical procedure for the test patient can be determined based on the similarity of the reference and test data vectors in the resulting cluster. The prognosis provides an indication of the likelihood that a patient will have a particular physiological state (such as an increased risk of IOH) or post-surgical outcome following the surgical procedure, whether positive or negative. The prognosis can be determined, assessed, and utilized as discussed above for methods involving MAP, MAC, and BIS measures.

In an alternative embodiment, the computer-implemented method as discussed above can be performed by interrogating an average of the sum of the concurrent MAP, MAC, and BIS measures at each sequential time interval over the course of the surgical procedure, instead of using a K-means clustering procedure to classify the test data vector characterizing the MAC, MAP, and BIS values. For a reference population of patients, the average of the sum of the concurrent MAP, MAC, and BIS measures at each sequential time interval of the surgical procedure can be associated to an outcome of interest. Accordingly, the average of the sum of the concurrent MAP, MAC, and BIS measures at each sequential time interval of the surgical procedure of a test patient can be compared with the corresponding values from the reference population of patients, for example to determine a prognosis for the test patient.

IV. Example Computing Environment

Figure 2:
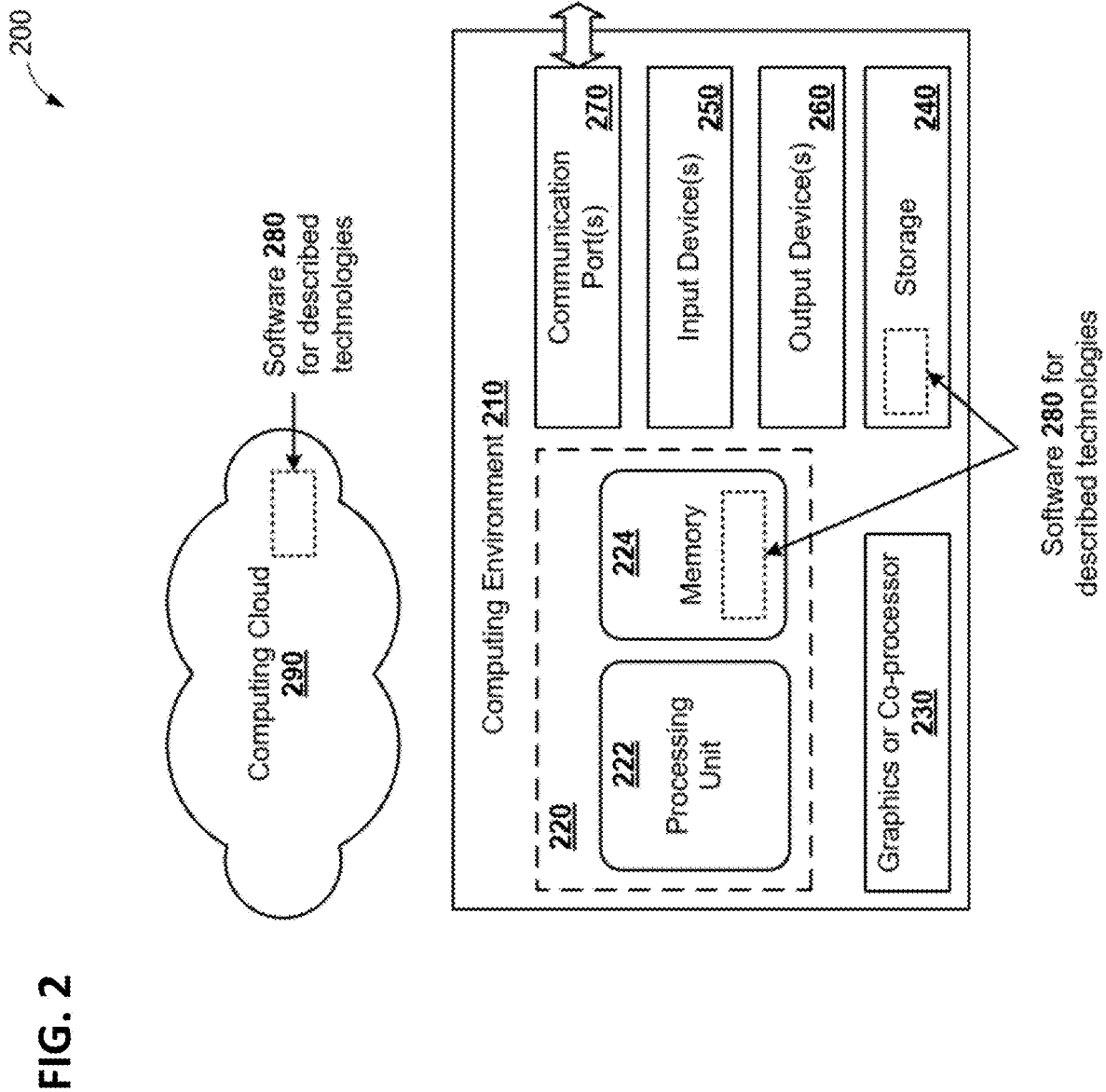
FIG. 2 illustrates a generalized example of a suitable computing environment in which described embodiments, techniques, and technologies, including performing classification, can be implemented.

FIG. 2 illustrates a generalized example of a suitable computing system 200 in which described examples, techniques, and technologies, including K-means clustering of data vectors characterizing concurrent MAP, BIS, and MAC measures, or MAC and MAP measures, or MAC and BIS measures, for sequential time periods of a surgery of a test patient, can be implemented. For example, the computing system 200 can implement all of the functions described with respect to FIG. 1, as described herein.

The computing system 200 is not intended to suggest any limitation as to scope of use or functionality of the technology, as the technology can be implemented in diverse general-purpose or special-purpose computing environments. For example, the disclosed technology can be implemented with other computer system configurations, including hand held devices, multiprocessor systems, microprocessor-based or programmable consumer electronics, network PCs, minicomputers, mainframe computers, integrated anesthesia monitors, and the like. The disclosed technology can also be practiced in distributed computing environments where tasks are performed by remote processing devices that are linked through a communications network. In a distributed computing environment, program modules can be located in both local and remote memory storage devices.

With reference to FIG. 2, the computing environment 210 includes at least one central processing unit 222 and memory 224. In FIG. 2, this most basic configuration 220 is included within a dashed line. The central processing unit 222 executes computer-executable instructions and can be a real or a virtual processor. In a multi-processing system, multiple processing units execute computer-executable instructions to increase processing power and as such, multiple processors can be running simultaneously. The memory 224 can be volatile memory (e.g., registers, cache, RAM), non-volatile memory (e.g., ROM, EEPROM, flash memory, etc.), or some combination of the two. The memory 224 stores software 280 that can, for example, implement the technologies described herein. Computing environment 210 can also include a graphics processing unit or co-processing unit 230.

A computing environment can have additional features. For example, the computing environment 200 includes storage 240, one or more input devices 250, one or more output devices 260, and one or more communication connections 270. An interconnection mechanism (not shown) such as a bus, a controller, or a network, interconnects the components of the computing environment 200. Typically, operating system software (not shown) provides an operating environment for other software executing in the computing environment 200, and coordinates activities of the components of the computing environment 200.

The storage 240 can be removable or non-removable, and includes magnetic disks, magnetic tapes or cassettes, CD-ROMs, CD-RWs, DVDs, or any other medium which can be used to store information and that can be accessed within the computing environment 200. The storage 240 stores instructions for the software 280 and measurement data, which can implement technologies described herein.

The input device(s) 250 can be a touch input device, such as a keyboard, keypad, mouse, touch screen display, pen, or trackball, a voice input device, a scanning device, or another device, that provides input to the computing environment 210. The input device(s) 250 can also include interface hardware for connecting the computing environment to control and receive data from host and client computers, storage systems, measurement acquisition components, control excitation sources, or to display or output data processed according to methods disclosed herein, including data acquisition systems coupled to a plurality of sensors.

In some embodiments, the computing system 200 includes one or more sensors for collecting the MAP, MAC, and BIS measurements from the patient during the surgery. In some embodiments, the computing system 200 includes one or more anesthetic data devices that generate data for the MAP, BIS, and/or MAC measurements. In some embodiments, the computing system 200 includes a display for real-time presentation of the representation of an identified cluster to a user. For example, the display can be configured for indicating to a treating anesthesiologist, anesthesia-care providers, and surgeon the status of a patient during a surgery. In some embodiments, the computing system 200 includes one or more alarms that indicate when a patient is in a particular physiological state during the surgery, such as a state having in increased risk of an IOH event.

For audio, the input device(s) 250 can be a sound card or similar device that accepts audio input in analog or digital form, or a CD-ROM reader that provides audio samples to the computing environment 200. The output device(s) 260 can be a display, printer, speaker, CD-writer, or another device that provides output from the computing environment 210.

The communication connection(s) 270 enable communication over a communication medium (e.g., a connecting network) to another computing entity. The communication medium conveys information such as computer-executable instructions, compressed graphics information, video, or other data in a modulated data signal.

Some examples of the disclosed methods can be performed using computer-executable instructions implementing all or a portion of the disclosed technology in a computing cloud 290. For example, construction of data vectors for MAP, BIS, and MAC measure profile, or MAC and MAP measure profile, or MAC and BIS measure profile, can be executed locally in the computing environment, while partitioning of the profile using a K-means clustering analysis can be performed on remote servers located in the computing cloud 290.

Computer-readable media are any available media that can be accessed within a computing environment 200. By way of example, and not limitation, with the computing environment 210, computer-readable media include memory 220 and/or storage 240. As should be readily understood, the term computer-readable storage media includes the media for data storage such as memory 220 and storage 240, and not transmission media such as modulated data signals.

The present innovations can be described in the general context of computer-executable instructions, such as those included in program modules, being executed in a computing system on a target real or virtual processor. Generally, program modules or components include routines, programs, libraries, software objects, classes, components, data structures, etc. that perform particular tasks or implement particular abstract data types. The functionality of the program modules can be combined or split between program modules as desired in various embodiments. Computer-executable instructions for program modules can be executed within a local or distributed computing system.

The terms "system," "environment," and "device" are used interchangeably herein. Unless the context clearly indicates otherwise, none of these terms implies any limitation on a type of computing system, computing environment, or computing device. In general, a computing system, computing environment, or computing device can be local or distributed, and can include any combination of special-purpose hardware and/or general-purpose hardware and/or virtualized hardware, together with software implementing the functionality described herein. Virtual processors, virtual hardware, and virtualized devices are ultimately embodied in one or another form of physical computer hardware.

V. Example Cloud Computing Environment

Figure 3:
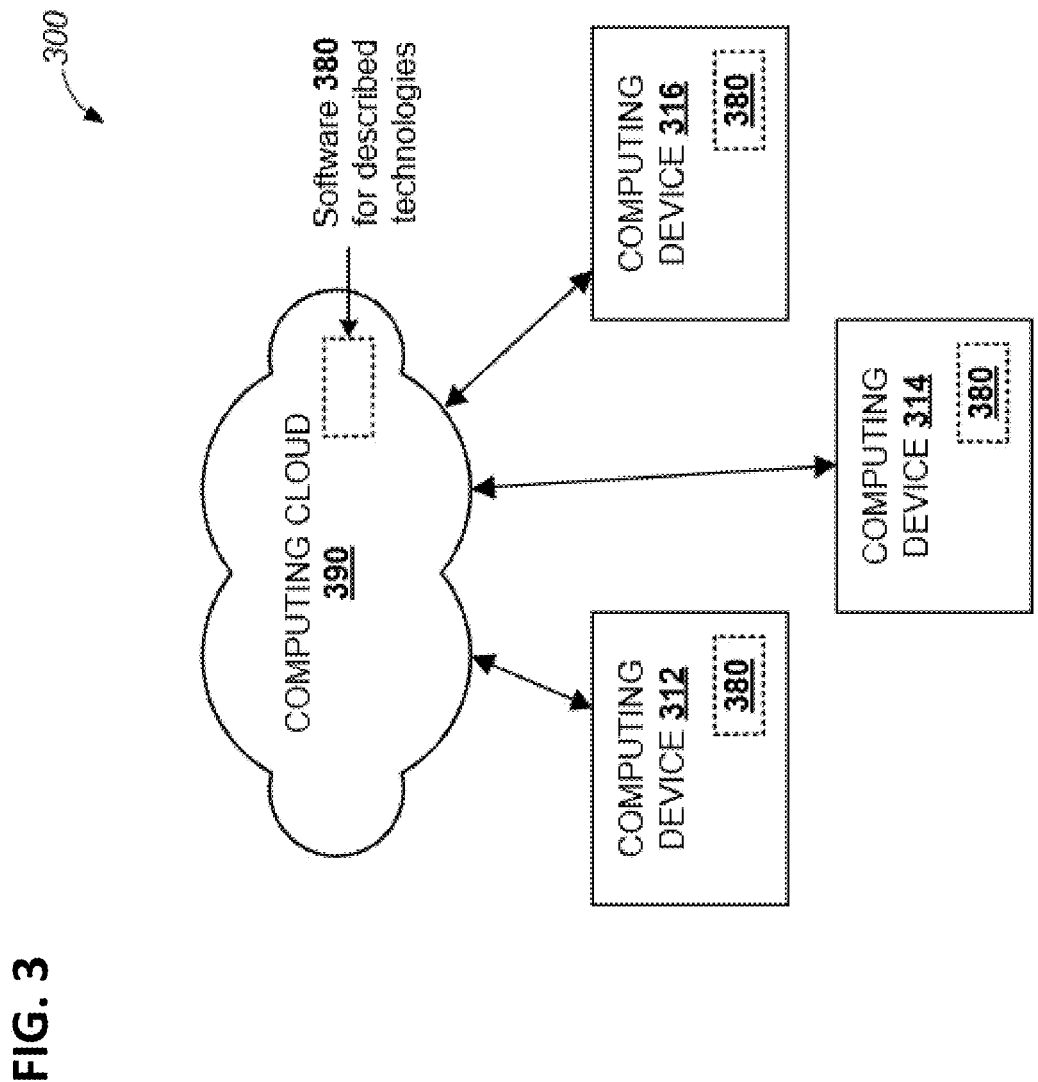
FIG. 3 is a diagram schematically depicting computing devices operating in conjunction with a computing cloud for implementation of disclosed technologies.

FIG. 3 depicts an example cloud computing environment 300 in which the described technologies can be implemented. The cloud computing environment 300 comprises a computing cloud 390 containing resources and providing services. The computing cloud 390 can comprise various types of cloud computing resources, such as computer servers, data storage repositories, networking resources, and so forth. The computing cloud 390 can be centrally located (e.g., provided by a data center of a business or organization) or distributed (e.g., provided by various computing resources located at different locations, such as different data centers and/or located in different cities or countries).

The computing cloud 390 can be operatively connected to various types of computing devices (e.g., client computing devices), such as computing devices 312, 314, and 316, and can provide a range of computing services thereto. One or more of computing devices 312, 314, and 316 can be computers (e.g., server, virtual machine, embedded systems, desktop, or laptop computers), mobile devices (e.g., tablet computers, smartphones, or wearable appliances), or other types of computing devices. Connections between computing cloud 390 and computing devices 312, 314, and 316 can be over wired, wireless, or optical links, or any combination thereof, and can be short-lived or long-lasting. These connections can be stationary or can move over time, being implemented over varying paths and having varying attachment points at each end. Computing devices 312, 314, and 316 can also be connected to each other.

Computing devices 312, 314, and 316 can utilize the computing cloud 390 to obtain computing services and perform computing operations (e.g., data processing, data storage, and the like). Particularly, software 380 for performing the described innovative technologies can be resident or executed in the computing cloud 390, in computing devices 312, 314, and 316, or in a distributed combination of cloud and computing devices.

VI. General Considerations

As used in this application the singular forms "a," "an," and "the" include the plural forms unless the context clearly dictates otherwise. Additionally, the term "includes" means "comprises." Further, the term "coupled" encompasses mechanical, electrical, magnetic, optical, as well as other practical ways of coupling or linking items together, and does not exclude the presence of intermediate elements between the coupled items. Furthermore, as used herein, the term "and/or" means any one item or combination of items in the phrase.

The systems, methods, and apparatus described herein should not be construed as being limiting in any way. Instead, this disclosure is directed toward all novel and non-obvious features and aspects of the various disclosed embodiments, alone and in various combinations and subcombinations with one another. The disclosed systems, methods, and apparatus are not limited to any specific aspect or feature or combinations thereof, nor do the disclosed things and methods require that any one or more specific advantages be present or problems be solved. Furthermore, any features or aspects of the disclosed embodiments can be used in various combinations and subcombinations with one another.

Although the operations of some of the disclosed methods are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed things and methods can be used in conjunction with other things and methods. Additionally, the description sometimes uses terms like "accept," "accumulate," "analyze," "apply," "assign," "attain," "calculate," "change," "complete," "configure," "control," "copy," "defines," "delete," "determine," "display," "estimate," "execute," "extract," "follow," "generate," "instantiate," "iterate," "log," "minimize," "modify," "move," "optimize," "proceed," "produce," "randomize," "record," "reject," "restart," "return," "select," "store," "swap," "take effect," or "vary" to describe the disclosed methods. These terms are high-level abstractions of the actual operations that are performed. The actual operations that correspond to these terms will vary depending on the particular implementation and are readily discernible by one of ordinary skill in the art.

Theories of operation, scientific principles, or other theoretical descriptions presented herein in reference to the apparatus or methods of this disclosure have been provided for the purposes of better understanding and are not intended to be limiting in scope. The apparatus and methods in the appended claims are not limited to those apparatus and methods that function in the manner described by such theories of operation.

Any of the disclosed methods can be implemented using computer-executable instructions stored on one or more computer-readable media (e.g., non-transitory computer-readable media, such as one or more optical media discs, volatile memory components (such as DRAM or SRAM), or nonvolatile memory components (such as flash drives or hard drives)) and executed on a computer (e.g., any commercially available computer, including smart phones or other mobile devices that include computing hardware). Any of the computer-executable instructions for implementing the disclosed techniques, as well as any data created and used during implementation of the disclosed embodiments, can be stored on one or more computer-readable media (e.g., non-transitory computer-readable media). The computer-executable instructions can be part of, for example, a dedicated software application, or a software application that is accessed or downloaded via a web browser or other software application (such as a remote computing application). Such software can be executed, for example, on a single local computer (e.g., as a process executing on any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C, C++, Common Lisp, Dylan, Erlang, Fortran, Go, Haskell, Java, JavaScript, Julia, Python, Scheme, or any other suitable programming language. Likewise, the disclosed technology is not limited to any particular computer or type of hardware. Certain details of suitable computers and hardware are well-known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

Having described and illustrated the principles of the innovations in the detailed description and accompanying drawings, it will be recognized that the various examples can be modified in arrangement and detail without departing from such principles.

VII. Additional Description of Disclosed Embodiments

Clause 1. A method for determining a prognosis of a test patient following a surgical procedure, comprising:
on one or more computer processors having memory attached thereto:
obtaining concurrent measures of one of
(a) mean arterial pressure (MAP), standard minimum alveolar concentration (MAC), and bispectral index (BIS) of the test patient from sequential time intervals during a surgical procedure that comprises administration of an inhalation anesthetic to the test patient;
(b) MAC and MAP of the test patient from sequential time intervals during a surgical procedure that comprises administration of an inhalation anesthetic to the test patient; and
(c) MAC and BIS of the test patient from sequential time intervals during a surgical procedure that comprises administration of an inhalation anesthetic to the test patient;
forming a test data vector characterizing the concurrent MAP and MAC measures, or the MAP, MAC, and BIS measures, for the sequential time intervals;
performing a K-means clustering procedure of the test data vector with a plurality of reference data vectors, wherein the reference data vectors characterize concurrent MAP and MAC measures, or MAP, MAC, and BIS measures, for sequential time intervals during surgical procedures of reference patients with a known post-surgical outcome;
identifying a cluster including the test data vector; and
determining a prognosis of the test patient based on the known post-surgical outcome of reference patients in the cluster including the test data vector.

Clause 2. The method of clause 1, comprising:

obtaining the concurrent measures of MAP, MAC, and BIS of the test patient from the sequential time intervals during the surgical procedure;

forming the test data vector characterizing the concurrent MAP, MAC, and BIS measures for the sequential time intervals;

performing the K-means clustering procedure of the test data vector with the plurality of reference data vectors, wherein the reference data vectors characterize the concurrent MAP, MAC, and BIS measures for sequential time intervals during surgical procedures of reference patients with a known post-surgical outcome.

Clause 3. The method of clause 1 or clause 2, wherein forming the test data vector, comprises:

normalizing each of the BIS and MAC measures of the test patient from the sequential time intervals, summing the normalized BIS and MAC measures from each time interval, and forming the test data vector from the respective sums of normalized BIS and MAC measures for the sequential time intervals; or normalizing each of the MAP and MAC measures of the test patient from the sequential time intervals, summing the normalized MAP and MAC measures from each time interval, and forming the test data vector from the respective sums of normalized MAP and MAC measures for the sequential time intervals; or normalizing each of the MAP, BIS, and MAC measures of the test patient from the sequential time intervals, summing the normalized MAP, BIS, and MAC measures from each time interval, and forming the test data vector from the respective sums of normalized MAP, BIS, and MAC measures for the sequential time intervals.

Clause 4. The method of any of the prior clauses, wherein the inhalation anesthetic is administered to the test patient as a general anesthetic.

Clause 5. The method of any of the prior clauses, wherein the concurrent MAP and MAC measures, the concurrent MAC and BIS measures, or the concurrent MAP, BIS, and MAC measures, are from time intervals during the surgical procedure when the test patient was unconscious due to the inhalation anesthetic.

Clause 6. The method of any of the prior clauses, wherein:

the concurrent BIS and MAC measures are normalized by calculating a Z-score for each individual measurement relative to respective reference BIS and MAC values;

the concurrent MAP and MAC measures are normalized by calculating a Z-score for each individual measurement relative to respective reference MAP and MAC values; or the concurrent MAP, BIS, and MAC measures, are normalized by calculating a Z-score for each individual measurement relative to respective reference MAP, BIS, and MAC values.

Clause 7. The method of any of the prior clauses, wherein the K-means clustering procedure comprises at least three centroids resulting in at least three clusters of data vectors characterizing the concurrent MAP and MAC measures, the concurrent BIS and MAC measures, or the concurrent MAP, BIS, and MAC measures, one of which comprises the test data vector.

Clause 8. The method of clause 6, wherein the K-means clustering procedure comprises five centroids resulting in five clusters of data vectors characterizing the concurrent MAC and MAP measures, the concurrent BIS and MAC measures, or the concurrent MAP, BIS, and MAC measures, one of which comprises the test data vector.

Clause 9. The method of any of the prior clauses, wherein the reference patients are from the same hospital system that performed the surgical procedure on the test patient.

Clause 10. The method of any of the prior clauses, wherein the surgical procedure of the reference patients is the same as the surgical procedure performed on the test patient.

Clause 11. The method of any of the prior clauses, wherein the surgical procedure comprises ear-nose-throat surgery, trauma surgery, urological surgery, neurosurgery, orthopedic surgery, vascular surgery, thoracic surgery, pediatric surgery, cardiac surgery, OB-GYN surgery, ophthalmologic surgery, transplant surgery, general surgery, plastic surgery, colon and rectal surgery, gynecologic oncology surgery, oral and maxillofacial surgery, or dental surgical services.

Clause 12. The method of any of the prior clauses, wherein the prognosis comprises a likelihood of a level of homeostatic capacity of the test patient following surgery.

Clause 13. The method of any of the prior clauses, wherein the prognosis comprises a likelihood of one or more post-surgical outcomes comprising one or more of infection, pain, nausea, vomiting, delirium, post-surgical complications, acute kidney injury, respiratory failure, acute anemia, thrombocytopenia, heart failure, coagulopathy, acidosis, malnutrition, sepsis, shock, hospital stay length of greater than average, and death hospital stay length of greater than average, and death.

Clause 14. The method of clause 13, wherein the prognosis comprises a likelihood of death within 30 days or 1 year following surgery.

Clause 15. The method of any of the prior clauses, wherein the sequential time intervals are five minutes in length.

Clause 16. The method of any of the prior clauses, comprising generating a post-surgical report comprising the prognosis following the surgical procedure for the test patient.

Clause 17. The method of clause 16, comprising outputting the post-surgical report to a user.

Clause 18. The method of any one of the prior clauses, further comprising storing data representing the prognosis following the surgical procedure for the test patient in a computer-readable storage medium.

Clause 19. The method of any one of the prior clauses, further comprising receiving data representing the prognosis following the surgical procedure for the test patient via a computer network.

Clause 20. A computing system comprising:

at least one processor with memory attached thereto;

wherein the computing system is configured to execute instructions to perform a method for determining a prognosis following a surgical procedure for a test patient according to any one of the prior clauses.

Clause 21. One or more computer-readable media storing computer-readable instructions, which, when executed by one or more processors, cause a computer comprising the processors to perform any one of the disclosed methods.

VIII. Examples

The following examples are provided to illustrate particular features of certain embodiments, but the scope of the claims should not be limited to those features exemplified.

Example 1

Triple Variable Index: A Novel Data Integration Tool that Identifies Distinct Intraoperative States of Physiology Linked to Disease Burden and Post-Surgical Death Health care systems generate a tremendous volume of data for the patient populations they treat. The growing data may enable health care systems to learn patient pathophysiology, predict outcomes, and allow timely interventions. This example provides a novel profiling system, Triple Variable Index (TVI), that integrates heterogeneous monitoring data representing cardiovascular and neurologic system functions, moment-to-moment, for individual patients responding to anesthetic and surgical interventions. Despite considerable study population diversity, surgical patients expressed one of three general TVI patterns, each representing a distinct physiologic state characterized by a host of patient and procedure-specific factors. Patterns reflect essential components of human physiology including organ system regulation and homeostasis, patient specificity, perioperative disease burden, and death following surgery. TVI profiling represents a novel platform to better understand the translation of patient risk into post-surgical outcome.

Introduction

To investigate data utilization strategies, physiologic monitoring data collected during surgery was evaluated. These data are dense and heterogeneous, yet represent the tightly regulated functions of multiple organ systems working in concert to maintain homeostatic balance. The coordinated actions of cardiovascular, neurologic, endocrine, metabolic, immune systems are required to meet the demand of surgical intervention, and as result, are often the target of intense intraoperative monitoring. Although there exists a large body of literature linking isolated physiologic variables to post-surgical outcomes, it remains a challenge to comprehensively assess patient physiology across multiple organ systems in ways that connect their regulated function over time to clinical outcomes.

Here, a novel approach called the Triple Variable Index (TVI) is described that simultaneously integrates cardiovascular and neurologic function data in response to anesthesia and surgery. The TVI may be generated at any time when mean arterial pressure (MAP), Bispectral Index (BIS) and minimum alveolar concentration (MAC) of inhalation anesthetic data are concurrently available. The TVI is mapped moment-to-moment for individual patients. By incorporating information from multiple variables over time, TVI reveals distinct patterns of organ system function that define specific states of intraoperative physiology characterized by a host of patient and procedure-related factors. Identified states exhibit both functional and clinical features including patient-specificity, organ system regulation/dysregulation, perioperative disease burden and risk of death following surgery.

Methods

Surgical Case Selection.

Surgeries that took place between Jan. 1, 2014 and Jul. 31, 2014 at University of Pittsburgh Medical Center Presbyterian and Montefiore hospitals were evaluated for study inclusion. 16,104 total surgeries occurred over this time period and included non-cardiac, cardiac and emergent cases. All ASA physical status categories were represented in available cases except category 6. Cases were included if MAP, BIS, and inhalation anesthetic concentration data were monitored and recorded during the surgery. Cases were excluded if MAP, BIS, inhalational anesthetic concentration variables were not available in the electronic anesthetic record, not measured concurrently, or inhalation anesthetics were not used during the case. Notably, 5528 cases did not record BIS values and 7097 cases did not use inhalation anesthetics. Total study cases were 5296 (Table 1).

Data Collection.

The following perioperative data for each study case from the electronic health care record systems at the University of Pittsburgh Medical Center was collected: MAP, end tidal concentration of inhalation anesthetics (isoflurane, desflurane, sevoflurane, nitrous oxide), BIS, medication/fluid administration, date, length, and type of surgery, International Classification of Diseases, Ninth Revision (ICD-9) codes, as well as patient ASA physical status, age, gender and date of post-surgical death if death occurred within 2 years following surgery. Mortality data were collected from the United States Social Security Death Index on Aug. 22, 2016. Both noninvasive and arterial line MAP values were collected and when both were present, arterial line measurements were used. Total MAC values were calculated by summing end tidal inhalation anesthetic concentrations using standard 1 MAC concentrations: isoflurane=1.17%, desflurane=6.6%, sevoflurane=1.8%, nitrous oxide=105% (see Nickalls, Br J Anaesth 91, 170-174, 2003). For this example, the term 'MAC' refers to the summed MAC values representing all inhaled anesthetics at a given measurement in time. Inhalation anesthetics were considered to be used any time MAC values were greater than 0.001, values less than this were considered clinically negligible. Outliers in the data were defined as MAP values greater than 250 and less than 10 mm Hg, MAC values greater than 3, and BIS values greater than 100 or less than 1.

Z-Scores, Sliding-Window Aggregation, and Triple Variable Index (TVI) Profiling.

MAP, MAC and BIS raw data were normalized using a Z-score as these variables exist on different scales. Specifically, a Z-score was calculated for each individual measurement relative to the total population of values for that given variable (e.g. MAP) collected from all available cases (16, 104). Variables were not consistently measured at the same time point or frequency (e.g. every 1 min vs. 5 min), thus were aggregated using a sliding window (Zeileis and Grothendieck (2005) Journal of Statistical Software, 1-27). For each variable, an average value was calculated over every five measurements starting at the beginning of the monitoring period. The sliding window was performed in non-overlapping, sequential manner. For example, window 1 represents averaged data from the $1^{st}$ five measurements, while window 2 represents the next five measurements. The TVI was calculated by summing Z scores of MAP, MAC and BIS variables within each window. A TVI value was only calculated if data from all three variables were available within the same monitoring window. A TVI profile was created for each study case by plotting the TVI across the intraoperative monitoring period.

K-Means Cluster Analysis.

K-means cluster analysis (see Hartigan and Wong, J Royal Statistical Society, Series C (Applied Statistics), 28:100-108, 1979, incorporated by reference herein) was performed to identify groups of similar TVI profiles. The K-means algorithm works to segregate TVI profiles into clusters where the sum of squares between the data points within a cluster and a reference value (known as a centroid) is minimized. The number of centroids included is user-defined and represents the total number of clusters used to segregate the dataset. TVI profiles were clustered using 3, 4 and 5 centroids each using 10 random starts and 100 maximum iterations.

Perioperative Mortality and Morbidity.

TVI profiles were given a mortality assignment based upon when the patient associated with the profile died. Assignments were mutually exclusive and were defined as (1) death occurring within 30 days, (2) after 30 days and within 1 year, (3) after 1 year and within 2 years, and (4) survived 2 years following surgery. Profiles were separated into groups based on their identified TVI pattern and mortality combinations (e.g. elevated TVI pattern profiles representing 30-day post-surgical mortality). Three TVI patterns and four possible post-surgical outcomes yielded twelve total groups. ICD-9 billing codes shared among 25, 30, and 35% of profiles within each group were identified.

Triple Low State Identification.

The Triple Low State, defined as MAP<75 mmHg, BIS<45, and MAC<0.8, represents a pathologic state associated with perioperative morbidity and mortality. The Triple Low State was assessed within each identified TVI pattern. For each TVI pattern, 400 profiles were randomly selected. Each monitoring window within the selected profiles was assessed for Triple Low State exposure. A window met Triple Low State criteria if MAP<75 mmHg, BIS<45, and MAC<0.8 occurred concurrently. Note MAC included nitrous oxide concentrations. The average percentage of total monitoring windows meeting Triple Low State criteria per profile was calculated for each sampled TVI pattern.

Organ System Regulation/Dysregulation.

Pearson correlations between MAC-MAP and MAC-BIS variable pairs were calculated using the profiles from each TVI pattern-post-surgical mortality group described above. Correlations were calculated for all available MAC-MAP and MAC-BIS pairs within a given group. Pairs were defined as variable values that occurred during the same intraoperative monitoring period. As a control, a correlation was calculated for the variable pairs by randomly pairing values.

Patient Specificity.

One thousand TVI profile pairs were randomly sampled from the dataset that shared a clinical variable of interest. Selected variables included individual patient, age, ASA physical status, procedure performed, gender, and post-surgical mortality outcomes as defined above. Pairs represented two individual surgeries and two unique patients, unless patient was the variable being tested (the same patient undergoing two different surgeries composed these pairs). The percentage of pairs that shared the same TVI pattern was calculated. As a control, the percentage of profiles sharing a TVI pattern in 1,000 random, non-variable matched pairs was calculated. Three independent extractions of 1,000 random pairs were performed for both experimental and control samples (n=3).

Statistical Software.

Data organization and analysis described herein were performed using the R Project for Statistical Computing (RStudio, Version 1.0.44, Vienna, Austria).

Results

Figure 4:
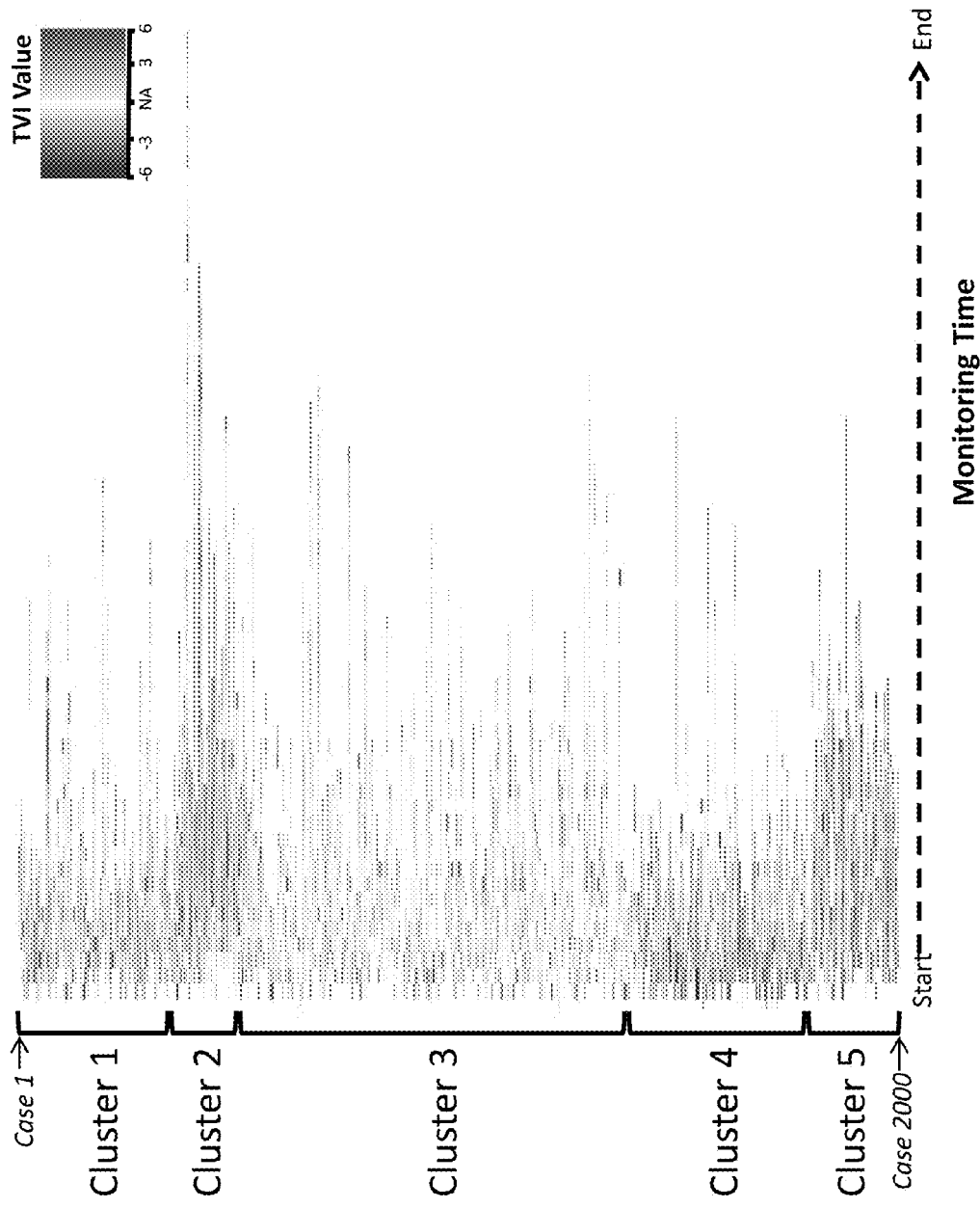
FIG. 4: 2000 sampled Triple Variable Index (TVI) profiles following K-means cluster analysis where k clusters=5. White in the heatmap represents periods of monitoring where TVI could not be calculated because 1) monitoring was not taking place or 2) MAP, BIS, and MAC values were not concurrently measured.
Figure 10:
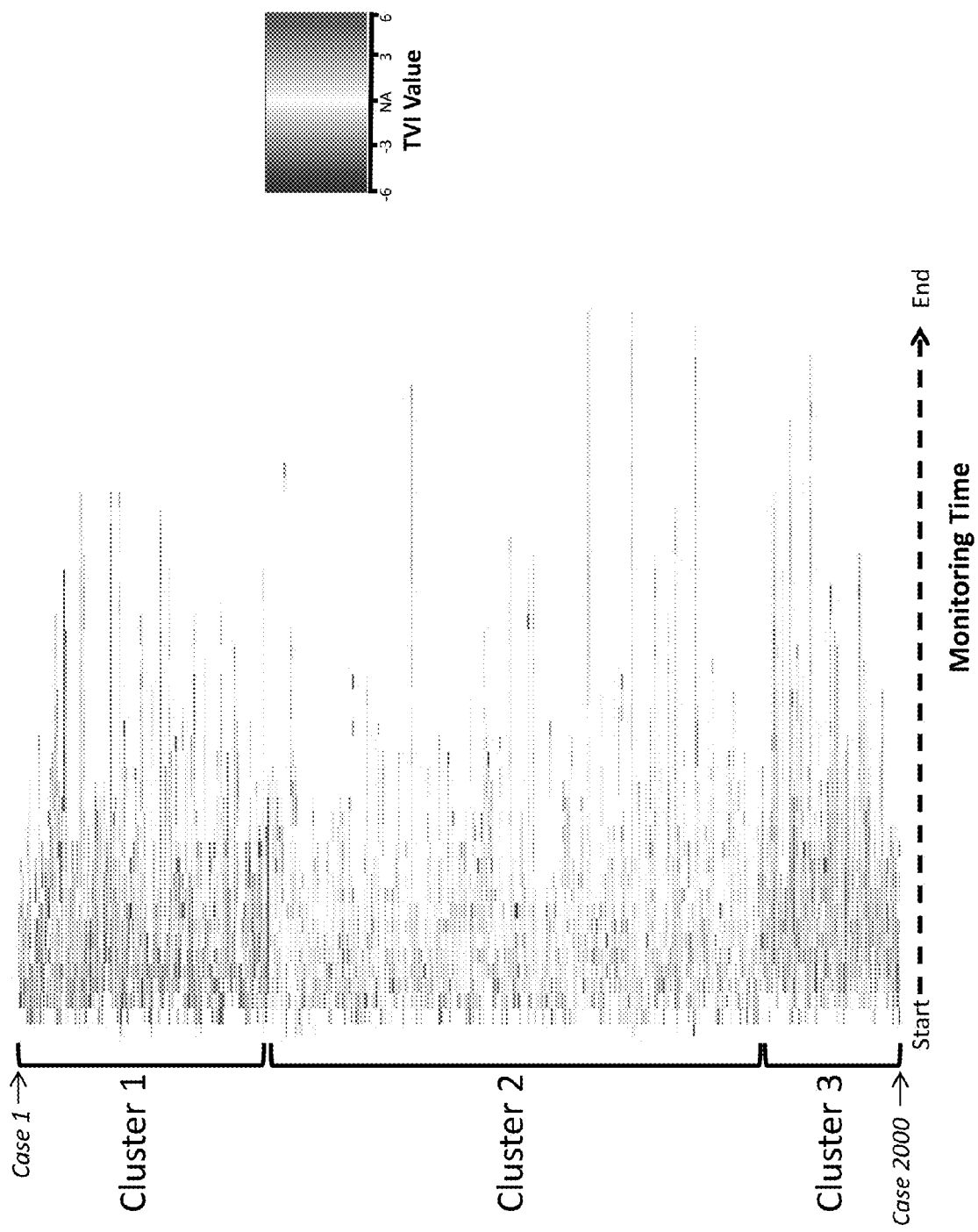
FIG. 10: 2000 sampled TVI profiles following K-means cluster analysis where k clusters=3. White in the heatmap represents periods of monitoring where TVI could not be calculated because 1) monitoring was not taking place or 2) MAP, BIS, MAC values were not concurrently measured.
Figure 11:
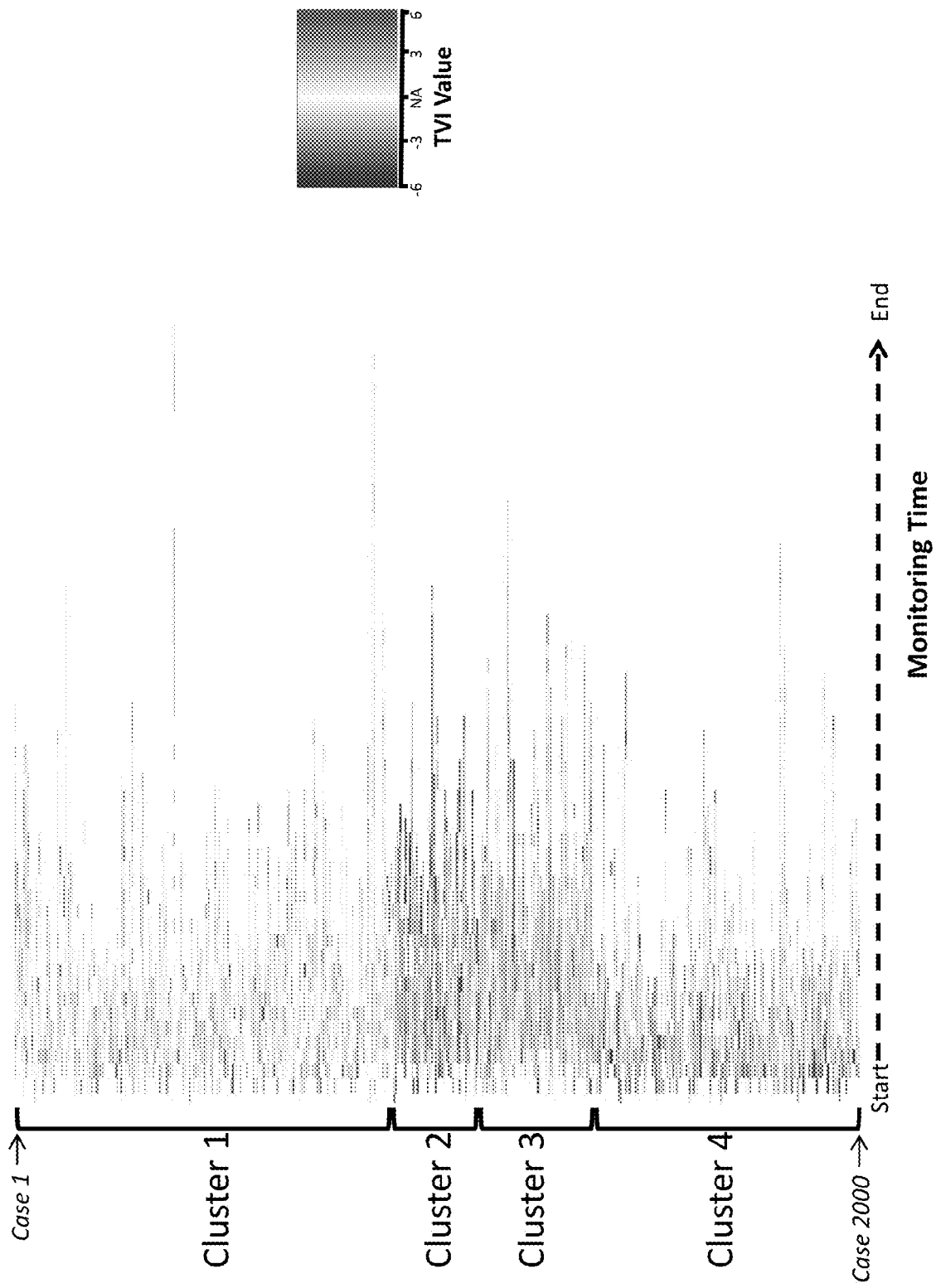
FIG. 11: 2000 sampled TVI profiles following K-means cluster analysis where k clusters=4. White in the heatmap represents periods of monitoring where TVI could not be calculated because 1) monitoring was not taking place or 2) MAP, BIS, MAC values were not concurrently measured.

FIG. 4 shows 2,000 randomly selected TVI profiles after K-means clustering. Three distinct patterns were expressed during surgery: cases that expressed consistently elevated index values (clusters 1 and 2), cases that expressed consistently depressed index values (clusters 4 and 5) and cases that expressed a mix of intermediate index values (cluster 3). To test if the expressed, depressed, and mixed TVI patterns are a function of cluster number, clustering was performed using 3, 4, and 5 clusters. Elevated, depressed and mixed TVI patterns remain clearly evident independent of the number of clusters used in the analysis (FIGS. 10 and 11).

Figure 12:
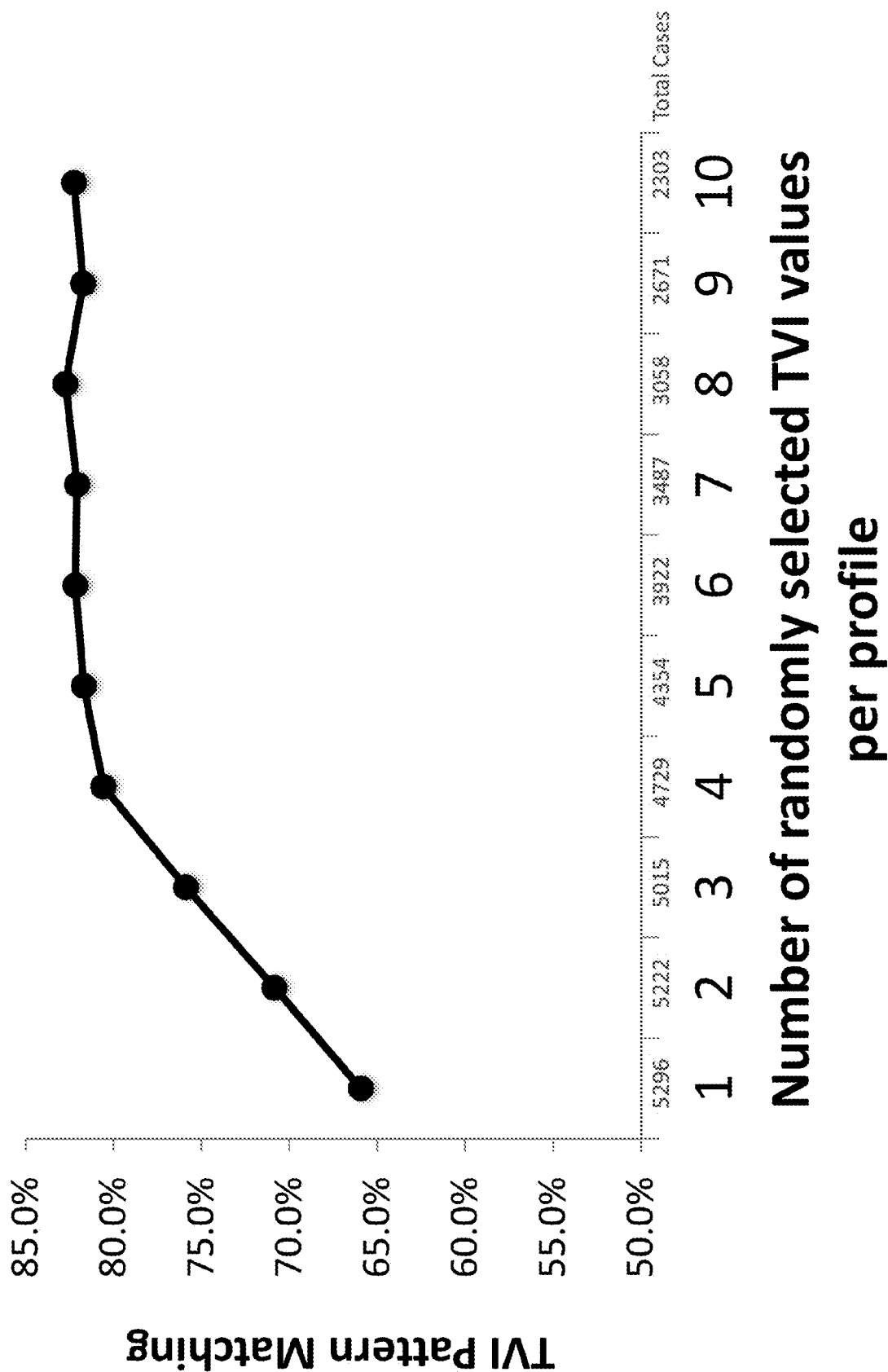
FIG. 12: K-means clustering was performed on TVI profiles, however only randomly sampled TVI values from each profile were used in the analysis. Up to 10 random values per profile were sampled (x-axis). The percentage of profiles that shared the same TVI pattern using sampled data as was identified using non-sampled, full profile data was calculated for each sample number. TVI patterns were defined as elevated, intermediate and depressed. Only profiles containing the minimum number of values to be sampled were included in each sampled data experiment (total cases on x-axis); duplicates were not permitted in sampled data.

Despite similar expression patterns, profiles in clusters 1 and 2 as well as those in clusters 4 and 5 are segregated in the 5-cluster analysis. Profiles in cluster 1 contain an average of 3.8 TVI values over the monitoring period compared to 17.9 TVI values per profile in cluster 2. Similarly, cluster 4 contains 3.1 TVI values per profile, on average, compared to 12.4 TVI values per profile in cluster 5. Clusters 1 and 4 likely contain less TVI data per profile because their associated procedures were shorter in length compared to clusters 2 and 5, respectively (Table 1). To test if TVI pattern assignment is a function of the amount of data collected during the monitoring period, a random sample of TVI values was taken from each TVI profile and K-means clustering performed using sampled data. For each profile tested, TVI pattern assignment was compared between whole and sampled data scenarios (FIG. 12). Even 1 randomly selected TVI value matches more than 65% of profiles to the same TVI pattern that is assigned when using all available data. If four or more values are sampled, a profile is matched to the same pattern more than 80% of the time. Taken together, TVI profiling combined with K-means cluster analysis identifies three physiologic patterns expressed by patients during the intraoperative period independent of cluster number, total amount of data collected, and monitoring time.

Figure 5:
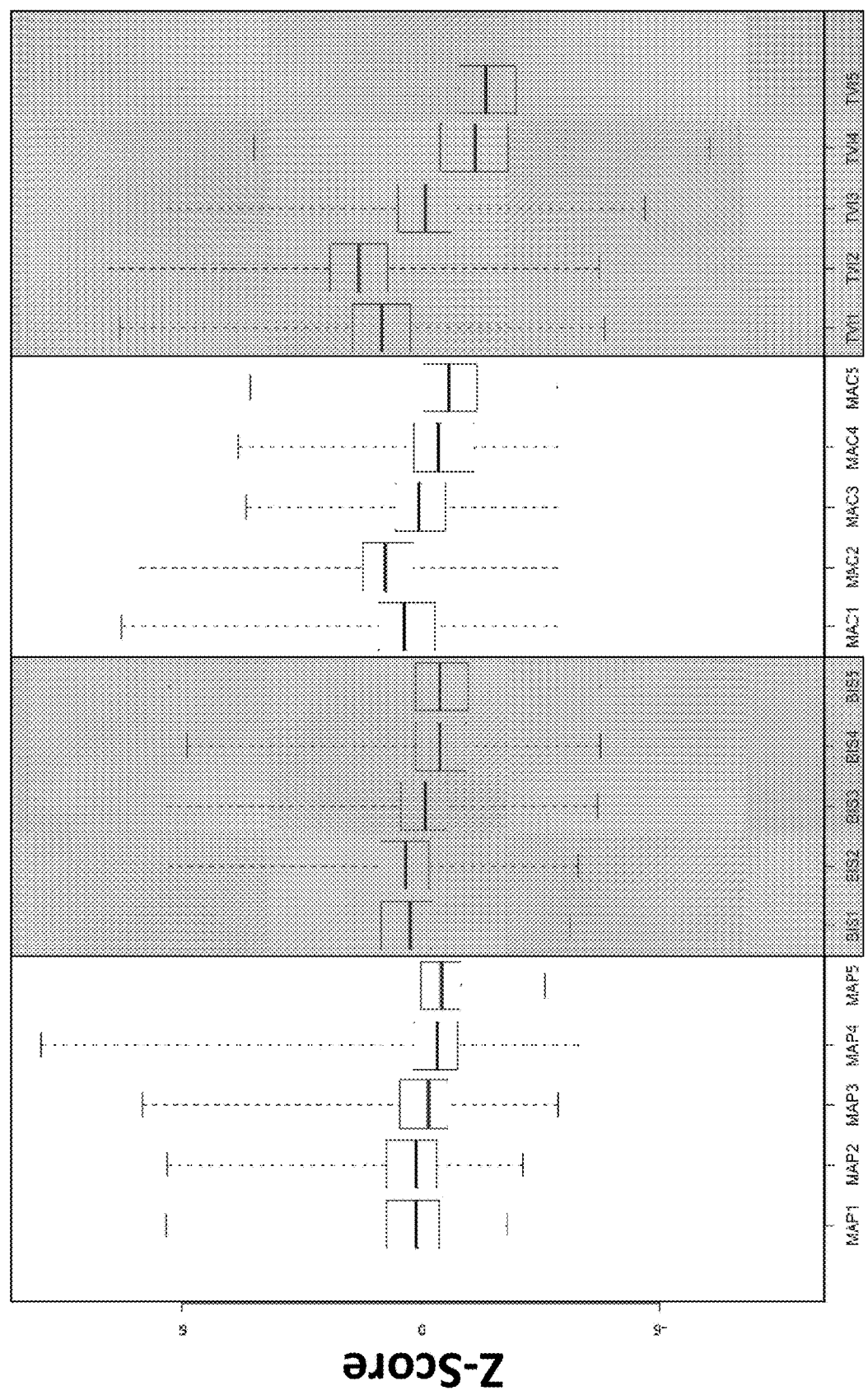
FIG. 5: 400 TVI profiles were randomly selected from each cluster (1-5). For each set of TVI profiles, the distribution of each study variable (MAP, BIS, MAC, TVI) was evaluated using boxplots. For example, MAP1 represents all of the MAP Z-scores within 400 randomly selected Cluster 1 TVI profiles. For each boxplot, upper and lower whiskers represent maximum and minimum Z-scores, respectively. Upper and lower hinges represent $3^{rd}$ and $1^{st}$ quartiles, respectively. The horizontal, bold line in the boxplot represents the median Z score.

Each TVI value represents three distinct variables simultaneously. To evaluate each variable's contribution to the observed TVI patterns, MAP, BIS and MAC variables were compared between 400 randomly selected profiles across clusters (FIG. 5, Table 3). The boxplots in FIG. 5 demonstrate that each variable contributes to the observed TVI patterns. Profiles in clusters 1 and 2, cluster 3, and clusters 4 and 5 that expressed an elevated, mixed, and depressed TVI pattern also exhibited the highest, intermediate and lowest MAP, BIS and MAC values in the study population, respectively.

The MAC variable has a well-established relationship with the MAP and BIS variables. Inhalational anesthetics are potent vasodilators (except NO) and central nervous system suppressants, thus increasing MAC levels decreases MAP and BIS levels. However, many factors can affect how an individual's MAP and BIS levels will respond to a given MAC level (Aranake et al., Anaesthesia, 68, 512-522, 2013). TVI patterns reveal the differential relationships between MAC, MAP and BIS variables expressed by surgical patients. For example, patients represented in cluster 4 that exhibited a depressed TVI pattern experienced low MAC levels (mean Z-score −0.52) in combination with low MAP and BIS levels (mean Z-scores −0.23 and −0.34, respectively). In contrast, cluster 1 patients representing an elevated TVI pattern experienced high MAC levels (mean Z-score 0.22) in combination with high MAP and BIS levels (mean Z-scores 0.24 and 0.38, respectively).

To further characterize the identified TVI patterns, patient and procedure data were examined across clusters (Table 1 Panel A and B). The mixed TVI pattern was the most commonly observed pattern representing more than 44% of total study cases. The depressed and elevated patterns occurred in 29.2% and 26.0% of cases, respectively. TVI profiles reflect individual surgeries and thus individual patients that were treated with more than one surgery between January and July 2014 were associated with more than one TVI profile. 4358 individual patients were represented in total; 17.7% of TVI profiles shared the same patient with another TVI profile. Patients that expressed an elevated TVI pattern experienced repeat surgical intervention in less than 6% of cases. In contrast, mixed TVI pattern patients experienced repeat surgical intervention in 11.1% of cases. Depressed TVI pattern patients represented patients at both high and low risk of repeat surgical intervention (12.9% vs. 3.3%).

ASA physical status assignment, incidence of emergent surgery and percentage of female patients were lowest, intermediate, and highest in patients that exhibited elevated, mixed and depressed TVI patterns, respectively (Table 1, Panel A). TVI profiles were associated most commonly with four surgical specialties: general, orthopedic, thoracic and cardiac surgery (Table 1, Panel B). Specifically, general, orthopedic and cardiac surgery were most commonly performed in cases that expressed a depressed TVI pattern, while general, orthopedic and thoracic surgery were most commonly performed in elevated and mixed TVI pattern cases. The types of procedures performed further distinguished TVI patterns. Cardiac valve replacement/repair and CABG procedures most commonly associated with a depressed TVI pattern, while anterior spine surgery and laparoscopic cholecystectomy were commonly associated with an elevated TVI pattern. Certain procedures were shared between TVI patterns such as irrigation and debridement and exploratory laparotomy, however their frequencies were cluster-dependent and neither was commonly performed in all clusters (defined as one of the top three most frequently performed procedures).

Commonly administered hypnotic, opioid, and vasopressor medications and fluids were compared between TVI patterns using the same 400 randomly selected profiles in FIG. 5 (Tables 4-7). Etomidate, ketamine, hydromorphone, vasopressin, norepinephrine, epinephrine, phenylephrine, normal saline 0.9% and albumin 5% were differentially administered to patients across TVI patterns. Etomidate was administered in 4.3, 7.3 and 13.8% of sampled cases that expressed an elevated, mixed and depressed TVI pattern, respectively. Ketamine was administered in the opposite fashion: 11.5, 6.0 and 2.5% of sampled cases that expressed an elevated, mixed and depressed TVI pattern, respectively. Hydromorphone was administered in 46% of sampled cases that expressed an elevated TVI pattern, but less than 28% of other cases. Vasopressin, norepinephrine, epinephrine, and phenylephrine were all administered in more sampled cases moving from elevated to mixed to depressed TVI patterns. Finally, normal saline 0.9% and albumin 5% were administered in larger volumes, on average, in sampled cases from cluster 2 and 5. These cases expressed an elevated and depressed TVI pattern, respectively, and were associated with the longest procedures (Table 1, Panel B).

In sum, the evidence presented herein suggests TVI patterns represent distinct intraoperative states of physiology that are defined by 1) the level of cardiovascular and central nervous system function maintained at a given MAC level, 2) patient-specific factors such as ASA physical status and gender, and 3) procedure-specific factors such as the type of surgery performed and intraoperative fluid/medication administration. It was concluded that patients that share the same physiologic state, defined by TVI pattern, share additional features closely linked to patient physiology. Post-surgical mortality, disease burden, organ system regulation during surgery, and patient-specificity were compared between TVI patterns.

Table 2 shows the percentage of patients from each TVI pattern that died or survived within 2 years of surgery. Cluster 1 and 2 profiles as well as cluster 4 and 5 profiles were combined for this and subsequent analyses as these profiles represent the same physiologic state defined by elevated and depressed TVI patterns, respectively. Cluster 3 profiles represent the mixed TVI pattern. Risk of death within 2 years of surgery is lowest, intermediate and highest in patients that expressed an elevated, mixed, and depressed TVI pattern, respectively. However, differences in mortality are most pronounced in patients that die within 30 days of surgery. Specifically, 1.5, 2.6 and 5.7% of patients that expressed an elevated, mixed and depressed TVI pattern died within 30 days of surgery, respectively. 30-day mortality represents a 3.8 fold difference in risk of death between elevated and depressed TVI patterns, while death that occurred in the $2^{nd}$ post-surgical year represents a 1.3 fold difference between these groups of patients. These data suggest the relationship between a patient's current physiologic status and risk of post-surgical death is dynamic and changes over time. Risk is best informed when physiologic status is measured soon before death (e.g. within 30 days).

We assessed post-surgical mortality among profiles representing only unique patients for each TVI pattern (Table 2, panel B). Importantly, mortality trends among individual patients are similar to the trends observed among all study profiles shown in panel A. Comparing mortality between total cases and individual patients, the risk of death decreased most in patients that expressed mixed and depressed TVI patterns. This suggests these groups experience more repeat surgeries that are associated with 2-year post-surgical mortality than patients that express an elevated TVI pattern. This is further supported by the observation that patients in these groups experience the most surgeries per patient overall (Table 1 Panel A).

Figure 6:
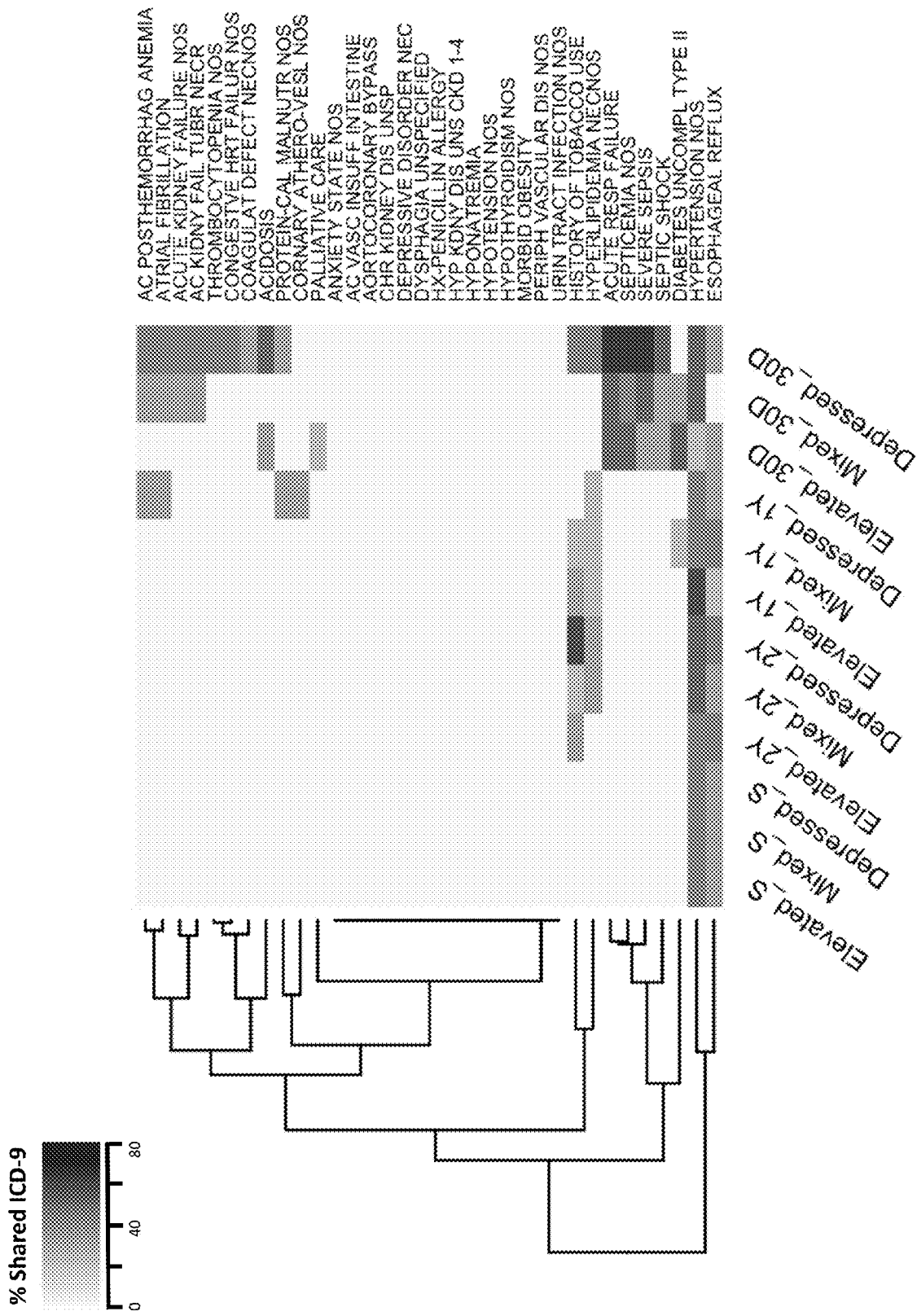
FIG. 6: Profiles were grouped according to their TVI pattern and post-surgical mortality. X-axis represents each unique TVI pattern-post-surgical mortality group. Y-axis represents International Classification of Disease (ICD)-9 billing codes that were shared among at least 25% of profiles within at least 1 TVI pattern-post-surgical mortality group. Each colored block in the heatmap represents the percentage of profiles that share the corresponding ICD-9 code. The darker the block, the higher number of profiles that share the given code. Rows were ordered using a dendrogram, columns were ordered along their TVI pattern-post-surgical mortality IDs. Codes represented by light orange (denoted by the red box) were shared below the chosen threshold (30%).

To test if patients sharing the same physiologic state also experienced similar disease processes during the perioperative period, we evaluated shared ICD-9 billing codes across TVI patterns. FIG. 6 demonstrates a relationship between specific diseases and post-surgical death. Hyperlipidemia and history of tobacco use were frequently shared among patients that died between 30 days and 2 years of their surgery. In contrast, patients that died within 30 days of surgery shared acute disease processes including sepsis, acute respiratory failure, acute kidney failure, post-hemorrhage anemia, and acidosis. Prevalent disease states such as esophageal reflux and hypertension were commonly shared between all TVI pattern-mortality groups.

Figure 13:
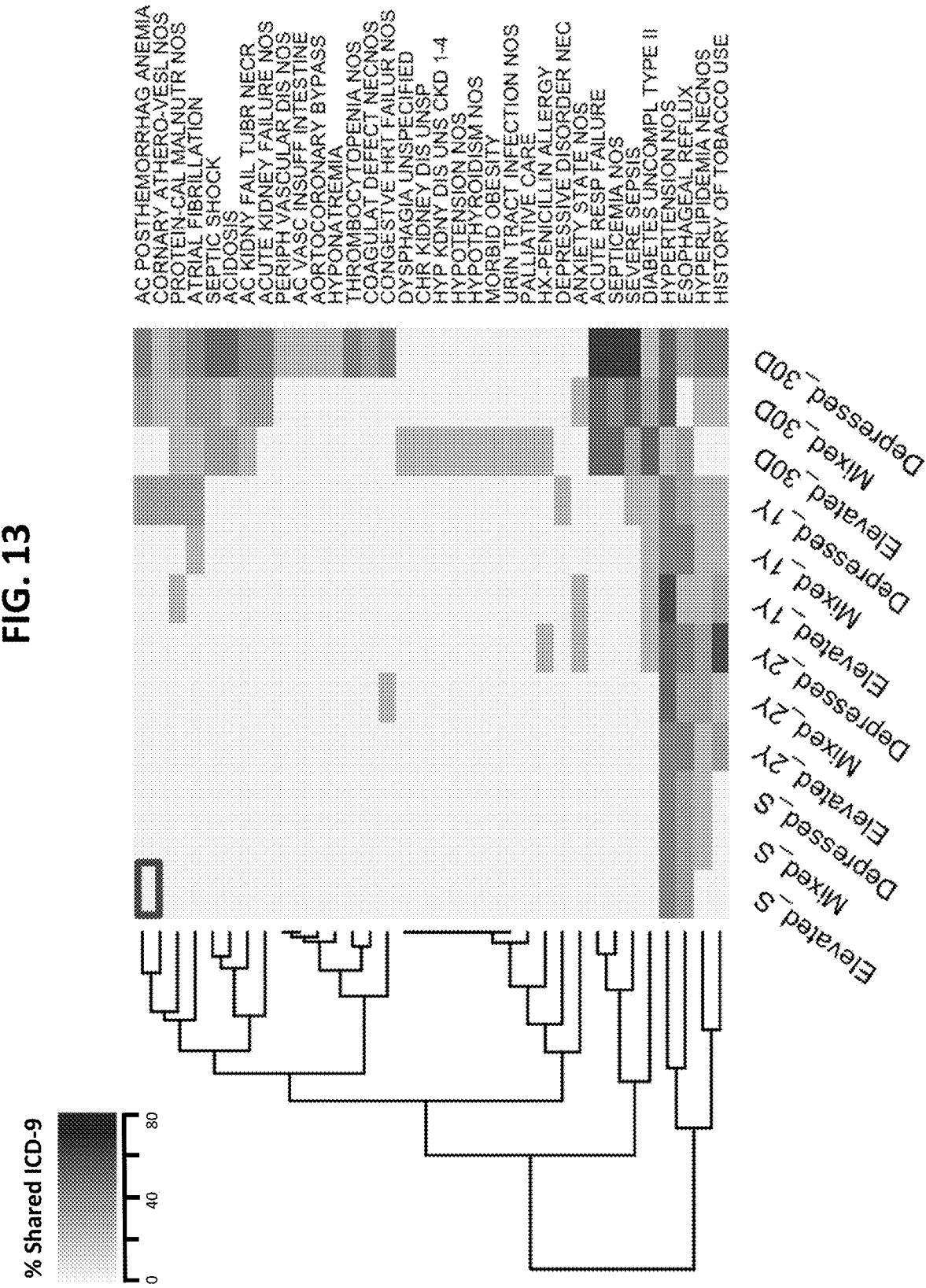
FIG. 13: Profiles were grouped according to their TVI pattern and post-surgical mortality. X-axis represents each unique TVI pattern-post-surgical mortality group. Y-axis represents ICD-9 billing codes that were shared among at least 25% of profiles within at least 1 TVI pattern-post-surgical mortality group. Each colored block in the heatmap represents the percentage of profiles that share the corresponding ICD-9 code. The darker the block, the higher number of profiles that share the given code. Rows were ordered using a dendrogram, columns were ordered along their TVI pattern-post-surgical mortality IDs. Codes represented by light orange (denoted by the red box) were shared below the chosen threshold (25%).
Figure 14A:
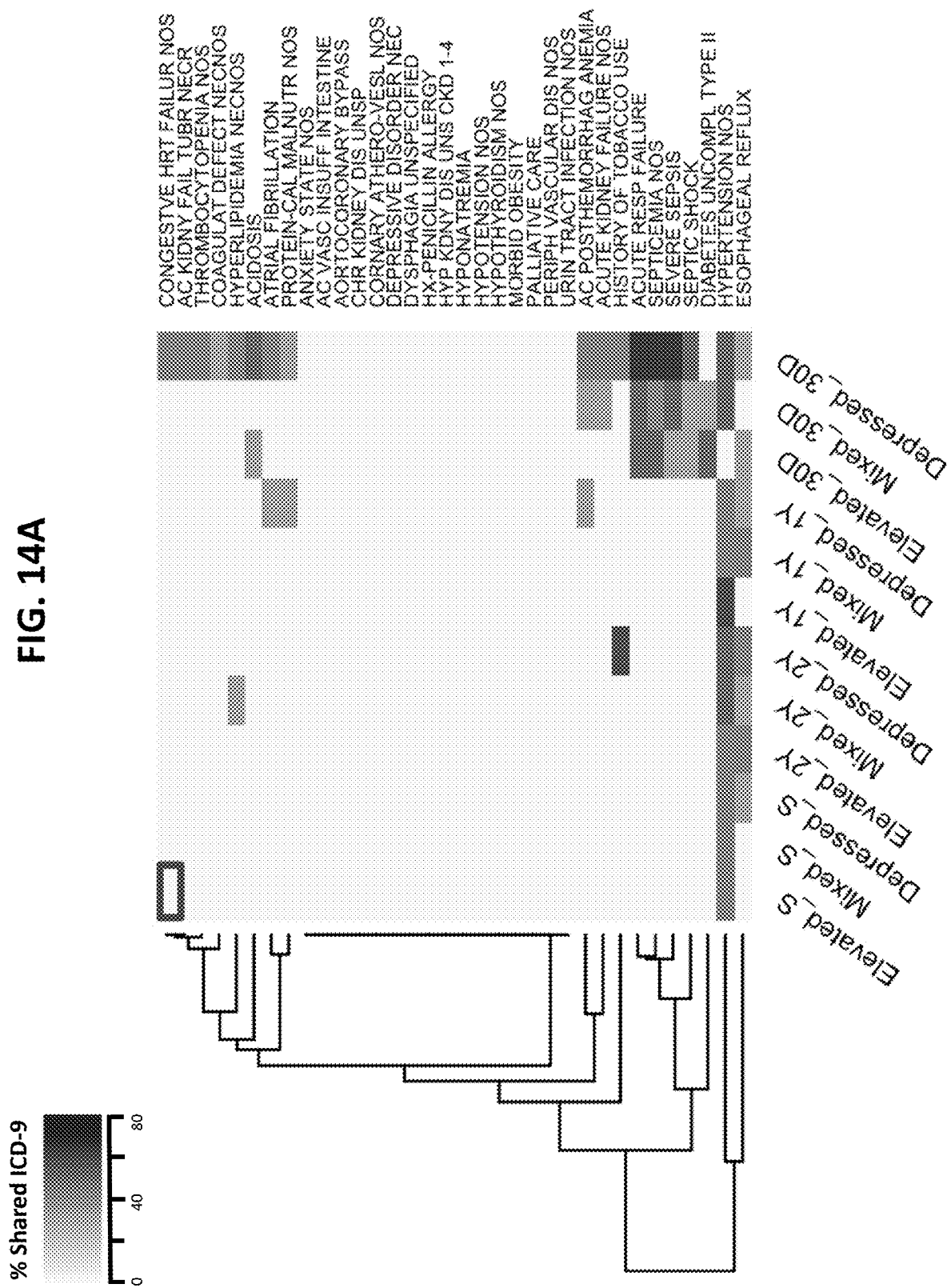
FIG. 14A: Profiles were grouped according to their TVI pattern and post-surgical mortality. X-axis represents each unique TVI pattern-post-surgical mortality group. Y-axis represents ICD-9 billing codes that were shared among at least 25% of profiles within at least 1 TVI pattern-post-surgical mortality group. Each colored block in the heatmap represents the percentage of profiles that share the corresponding ICD-9 code. The darker the block, the higher number of profiles that share the given code. Rows were ordered using a dendrogram, columns were ordered along their TVI pattern-post-surgical mortality IDs. Codes represented by light orange (denoted by the red box) were shared below the chosen threshold (35%).

TVI patterns demonstrate unique combinations of disease states. For example, patients that died within 30 days of surgery and expressed a depressed TVI pattern suffered from a wide range of diseases affecting multiple organ systems including sepsis, acute respiratory failure, acute kidney failure secondary to tubular necrosis, thrombocytopenia, coagulopathy, congestive heart failure and malnutrition. Patients that also died within 30 days of surgery but expressed mixed and elevated TVI patterns did not experience such breadth and frequency of disease. Performing the analysis using lower and higher thresholds of sharing (25% and 35%) revealed similar findings shown in FIG. 6 (FIGS. 13 and 14).

Figure 14B:
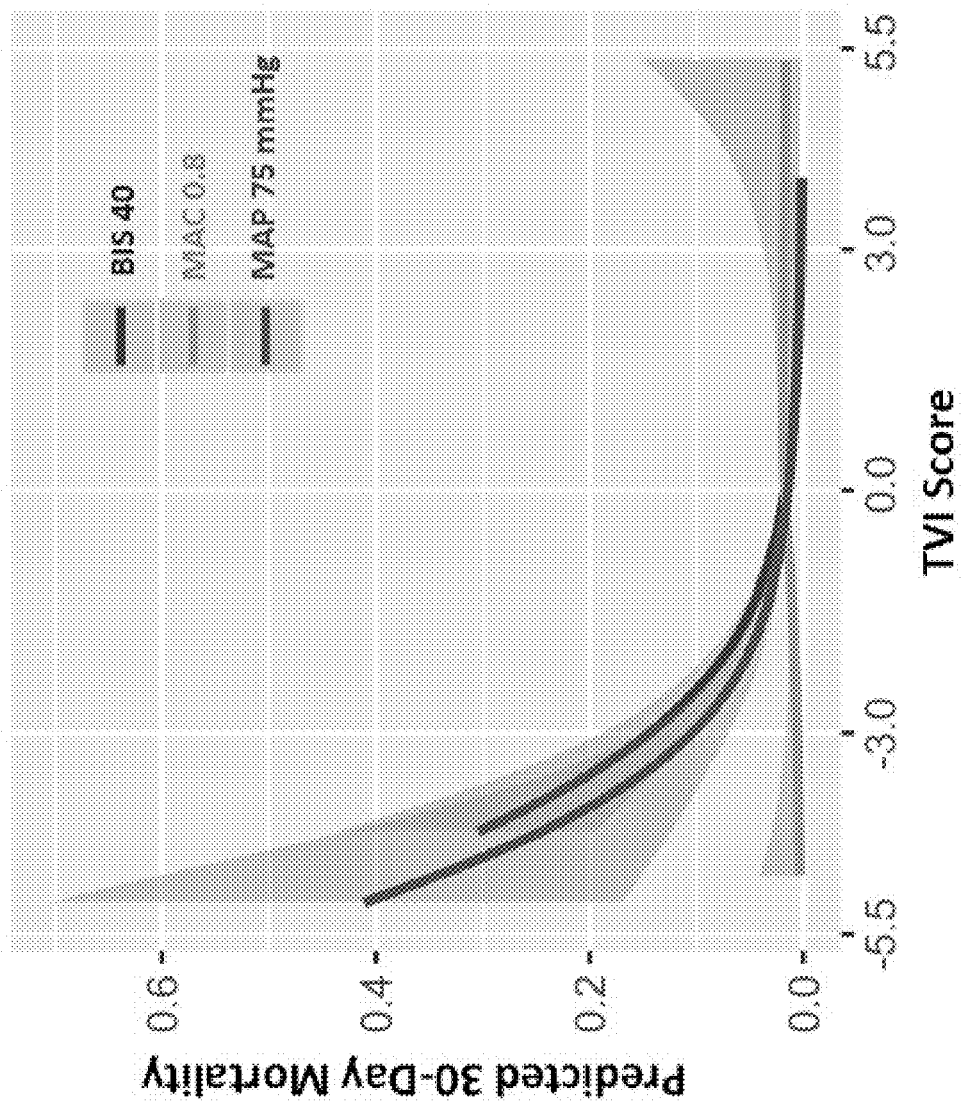
FIG. 14B: 30-day postoperative mortality predicted at individual TVI, MAP, BIS, and MAC z-scores. Grey shading represents 95% confidence interval. MAP=Mean arterial pressure. BIS=Bispectral Index. MAC=Minimum alveolar concentration. TVI=Triple Variable Index.
Figure 14C:
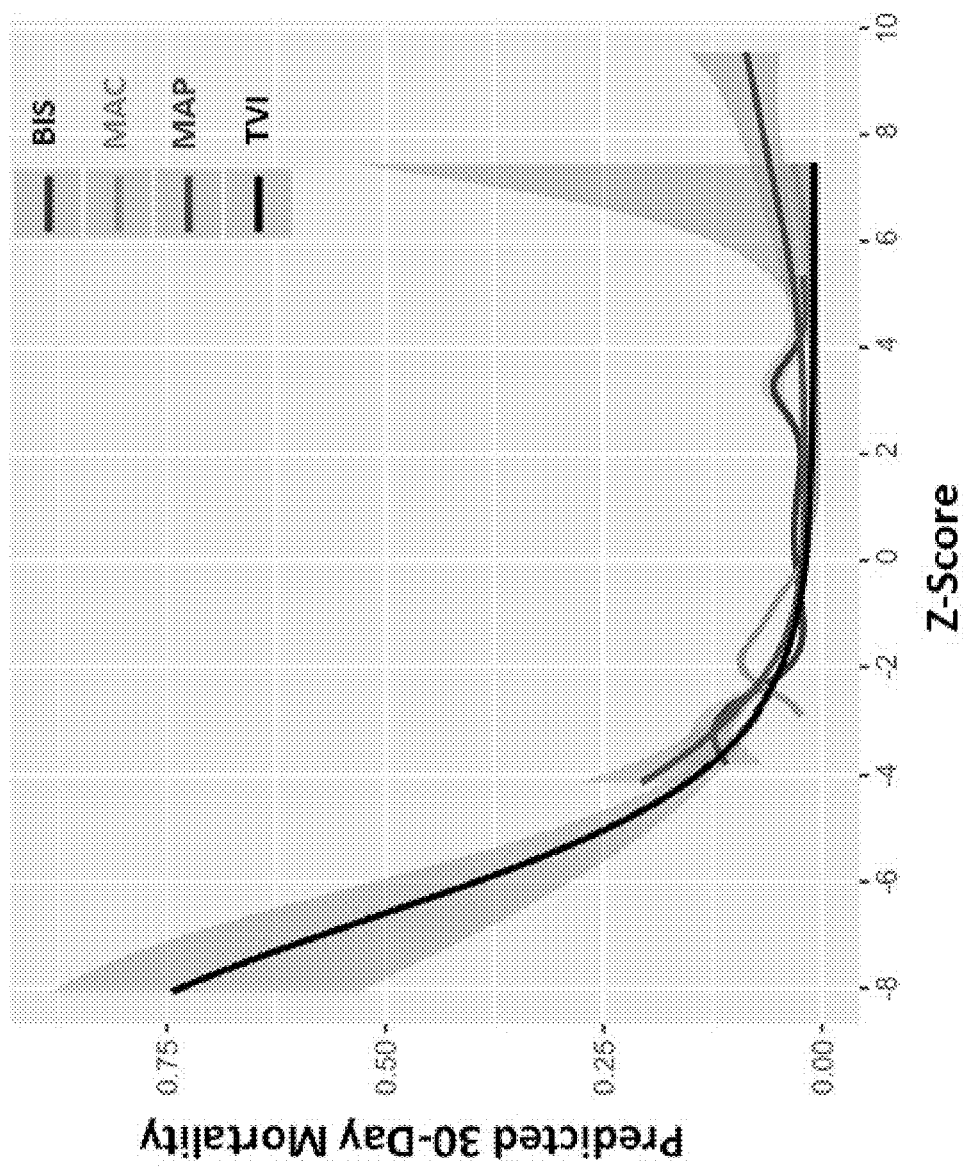
FIG. 14C: Relationship between TVI expression and 30-day postoperative mortality at defined MAP, BIS, and MAC levels. TVI values and predicted 30-day postoperative mortality for all MAP measurements of 75 mmHg that existed in the study population (red line). The same relationship is plotted for all BIS measurements of 40 (blue line) and all MAC measurements of 0.8 (green line) in the study population. Grey shading represents 95% confidence interval. MAP=Mean arterial pressure. BIS=Bispectral Index. MAC=Minimum alveolar concentration. TVI=Triple Variable Index.

TVI expression informed the risk of 30-day postoperative mortality beyond its composite MAP, BIS, and MAC variables. Clustering profiles using MAP and BIS data individually yielded no significant differences in associated postoperative mortality, while clustering using MAC data identified only high and low risk clusters. The highest predicted risk associated with individual TVI values was greater than 50%, while the highest predicted risk associated with any observed MAP, BIS, and MAC 460 value was less than 30% (FIG. 14B). The most common MAP level measured in the study population was 75 mmHg Despite representing the same physiologic measurement, its associated postoperative mortality varied with TVI expression (FIG. 14C). A MAP of 75 mmHg was associated with high risk when it occurred within low TVI values, and low risk when it occurred within high TVI values. Similar findings were observed with the mode BIS value, 40, but not the mode MAC value, 0.8.

Figure 7:
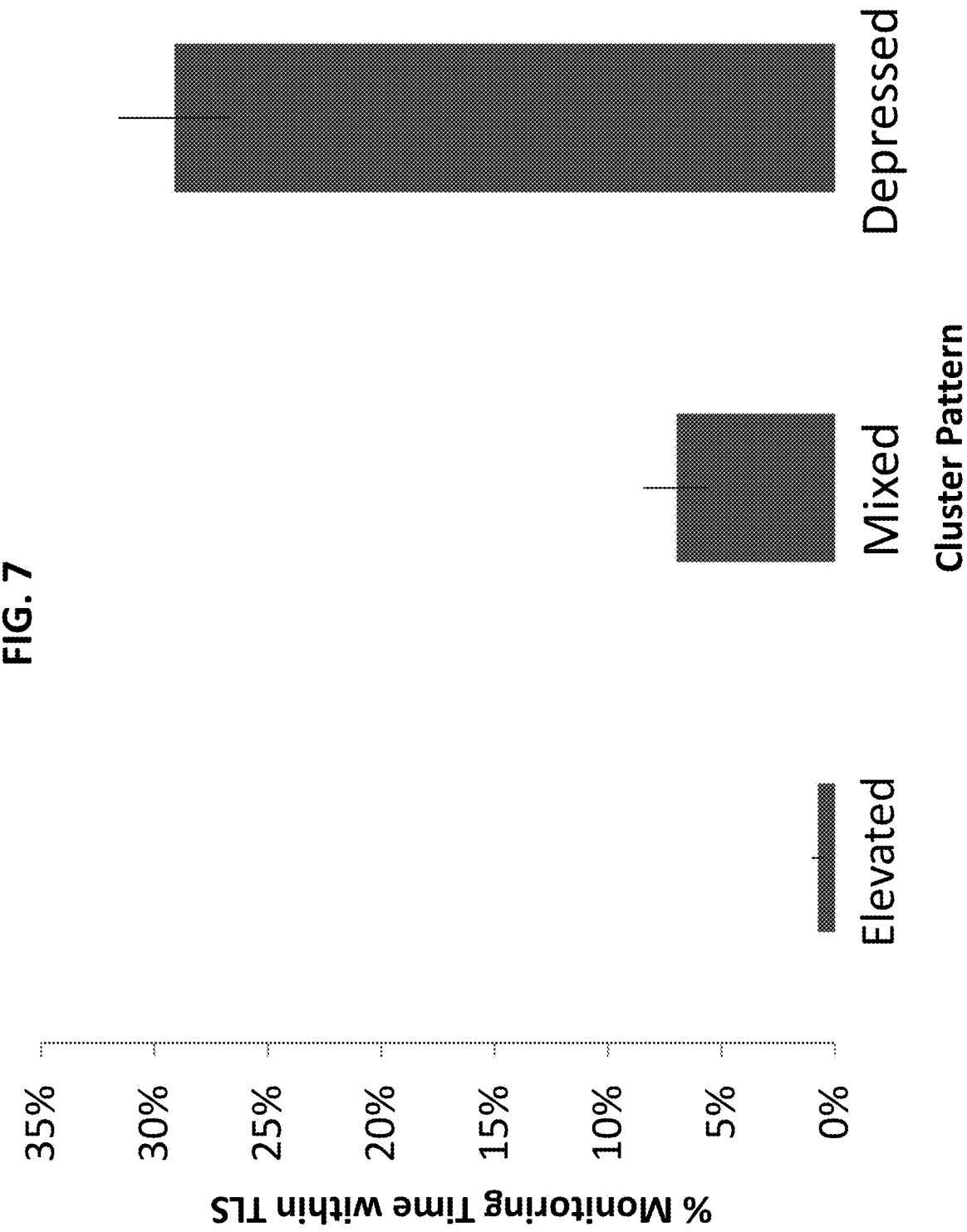
FIG. 7: Average percentage of the monitoring period spent within the Triple Low State defined as MAP<75 mmHg, MAC<0.8, and BIS<45 per case for each TVI pattern. Percentages were calculated using the same sampled TVI profiles shown in FIG. 2. Error bars represent 95% CI.

Next, the ability of patients in each TVI pattern to regulate their physiology during surgery was examined Patients enter the Triple Low State, a pathologic state defined as MAP<75 mmHg, BIS<45, and MAC<0.8, when they cannot maintain cardiovascular and neurologic function while being exposed to inhalation anesthetics. FIG. 7 shows the average amount of Triple Low State experienced per surgery across TVI patterns. Patients that expressed an elevated TVI pattern experienced the Triple Low State during less than 10% of the monitoring period, whereas patients expressing a depressed TVI pattern experienced the Triple Low State during 29% of the monitoring period.

The Triple Low State represents a single type of dysregulated physiology patients may experience, others potentially exist. To more broadly investigate organ system dysregulation that occurs during surgery, the individual relationships connecting MAC, MAP, and BIS variables were examined MAC levels are inversely related to MAP and BIS levels; thus a negative correlation for each pair represents intact, well-regulated physiology.

As shown in FIG. 8, patients that survived the 2-year post-surgical period exhibited the strongest MAC-MAP, MAC-BIS regulation compared to their random controls. As the risk of dying soon after surgery increased, patients were more likely to exhibit dysregulated MAC-MAP and MAC-BIS relationships. MAC-MAP regulation was disrupted across all TVI patterns in patients that died within 30 days of surgery. Patients that expressed a depressed TVI pattern were at risk of profound dysregulation affecting both cardiovascular and neurologic systems. MAC-BIS regulation was disrupted in patients that expressed a depressed TVI pattern and died within 30 days of surgery, whereas patients that expressed other TVI patterns maintained this relationship independent of post-surgical death. MAP and BIS variables have a less clearly defined relationship (Estruch-Perez et al. Ann Vasc Surg 24, 393-399, 2010; Hayashida et al., Br J Anaesth 90, 694-698, 2003) this is supported by the data as experimental and random correlations overlap across all TVI patterns.

Figure 9:
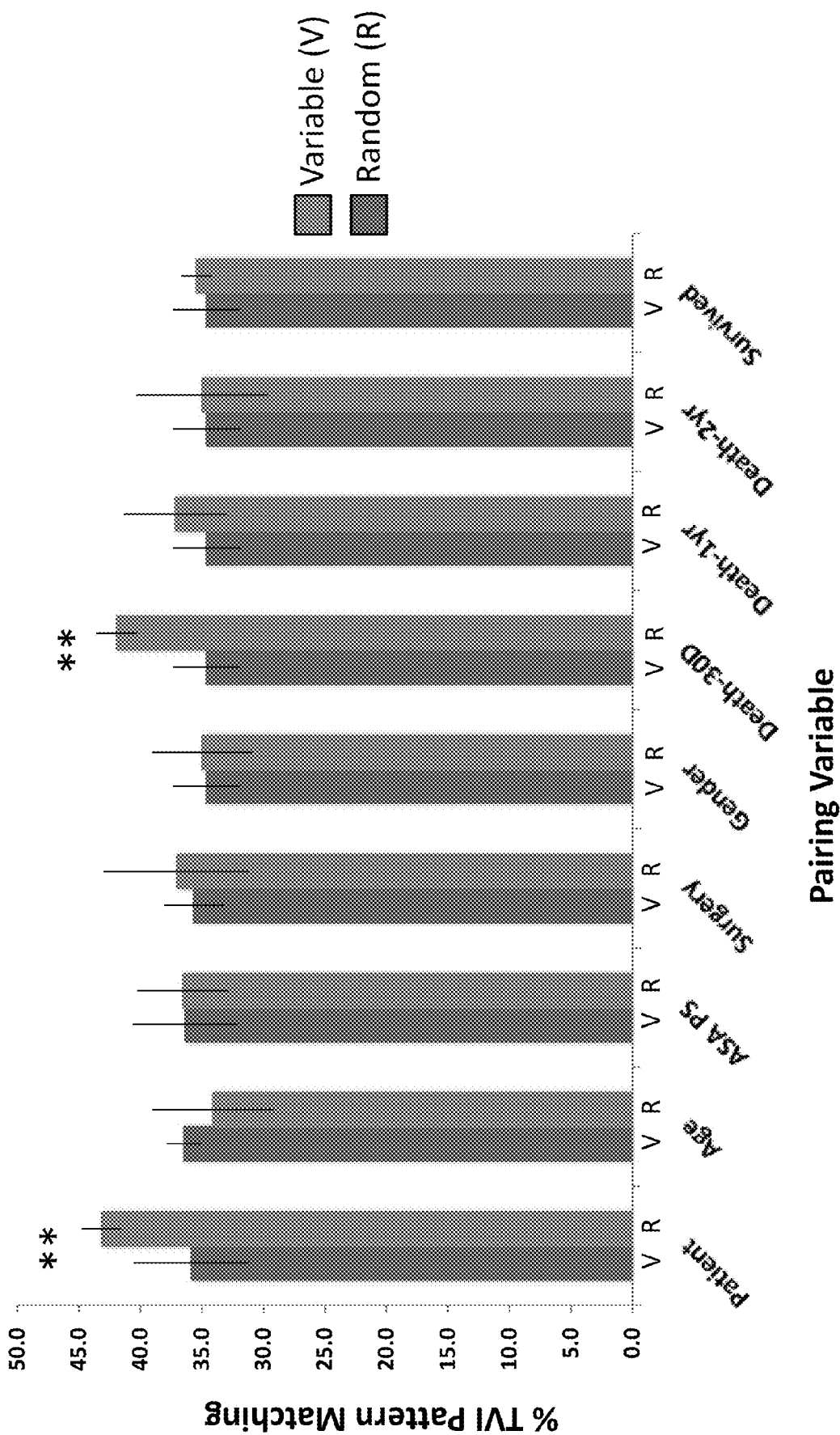
FIG. 9: 1000 random pairs of TVI profiles were selected that shared the same clinical variable (e.g. age). Profile pairs represent different surgeries and different patients unless identical patient was being tested as the clinical variable. The percentage of pairs sharing the same TVI pattern is shown on the y-axis. Three independent extractions of 1000 pairs were performed for each clinical variable and its associated random control. Error bars represent 95% CI.

Characterized by many patient and procedure-related factors, TVI patterns may reflect patient-specific physiology at the time of surgery. To test this, the TVI patterns associated with patients undergoing more than 1 surgery were evaluated (FIG. 9). TVI patterns that shared other factors linked to patient-specific physiology were also examined including age, ASA physical status, type of procedure and post-surgical outcome. As shown in FIG. 9, individual patients were more likely to express the same TVI pattern over multiple surgeries compared to the random control unlike patients that shared the same age, ASA physical status or type of surgery. Patients that died within 30 days of surgery also shared similar TVI pattern expression.

Discussion

The TVI represents a non-traditional approach to using patient data to better understand perioperative physiology. First, the TVI maps multiple, dynamic physiologic variables simultaneously over the entire monitoring period, a feature that carries clinical relevance. For example, patients that expressed a depressed TVI pattern displayed relatively low BIS and MAP values together with low MAC values and were "sickest" among all study patients. Preoperatively, these patients were assigned the highest ASA physical status classification, while intraoperatively they were most likely to experience high-risk surgery (e.g. cardiac and emergency surgery), the Triple Low State, and dysregulated MAC-MAP and MAC-BIS relationships. Post-surgically, these patients were at greatest risk of death within 30 days of surgery and repeat surgical intervention. These patients experienced the most extensive disease burden including both acute and chronic processes affecting multiple organ systems. The data demonstrate the inability to maintain MAP and BIS levels with increasing MAC levels identifies a physiological status associated with high risk and disease during the perioperative period.

Next, the TVI is broadly applicable to a wide population of surgical patients. A TVI profile can be generated for any patient where MAP, MAC and BIS data are available. In this example, patients from all ASA physical status classes were represented (except 6 whose is assignment is reserved for organ donation) as well as patients undergoing cardiac, emergency and repeat surgery. However, less than one third of available cases contained the requisite data to calculate at least 1 TVI. The reason for this are several fold: 1) BIS is not a standard monitor, 2) general anesthesia can be performed using non-inhalation agents (i.e. propofol infusion), 3) monitored anesthesia care and peripheral nerve blocks are commonly employed in place of general anesthesia for appropriately selected cases. The data demonstrate MAP values follow a similar pattern to BIS values across TVI patterns (elevated, mixed, and depressed). It may be possible to infer BIS values if only MAP and MAC data are available, thus extending TVI applicability within patient populations. In the study population, cases available for TVI analysis would increase from 5296 to 9007.

The TVI assesses patient physiology without applying variable thresholds. Thresholds produce two effects: 1) they limit the amount of data used in the analysis that may be potentially informative, and 2) they exclude patients from analysis whose data do not meet threshold. TVI profiling makes few assumptions about the underlying data that drive pattern expression for each patient. Outlier criteria was used to exclude data that were either non-physiologic (MAP>250 mmHg) or likely represent a charting/recording error (MAC>3). Cluster number is user-defined and must be selected prior to analysis, however, it was demonstrated that TVI patterns are readily identified over multiple clusters and varying monitoring periods.

TVI patterns are characterized by unique combinations of patient and procedure-related factors suggesting expression is "context-sensitive." Three lines of evidence support this finding. First, individual surgical procedures were associated with multiple TVI patterns and did not demonstrate specificity above random chance. Second, although TVI patterns demonstrate patient-specificity, patients undergoing more than one surgery expressed a different TVI pattern in randomly selected pairs of cases more than 50% of the time. Third, within a given case, TVI values associated with more than one TVI pattern occurred. The data suggest as the factors that drive TVI pattern expression change, TVI patterns change accordingly.

The TVI has the potential to provide new insight into the development of post-surgical outcomes. In contrast to Triple Low State identification, for example, the TVI provides information about the temporal relationships between MAC, MAP, and BIS variables. Patients that expressed a depressed TVI pattern and died within 30 days of surgery experienced the most severe physiologic dysregulation affecting both cardiovascular and neurologic systems over changing MAC levels. It is possible such patients had overall regulatory deficits that influenced their perioperative course. For example, sepsis, a condition characterized by multiple organ system dysfunction and overall physiologic derangement, was more commonly shared among these patients than other patients that also died within 30 days of surgery. It remains unclear if MAC-MAP and MAC-BIS dysregulation was secondary to pre-existing infections or a marker of general dysregulation that increases the risk of infection in identified patients. Future studies examining antibiotic treatment relative to surgery may shed further insight onto this question.

As a part of these efforts, a learning health system (LHS) was recently introduced as a new model of integrated care by the Institute of Medicine and expands the use of clinical data as a self-informing tool. Specifically, data collected and stored in electronic medical record (EMR) systems are applied towards generating new knowledge that can advance the care delivered in the future. TVI profiling fits well into a LHS-themed approach. Intraoperative patterns may inform post-surgical responses to common medications and adverse events. Harnessing lessons learned during surgery to improve subsequent care would require integration of diverse datasets, rapid analysis (near real-time) and clinically-meaningful interpretation, all features associated with TVI methodology.

For reasons related to TVI generation, interpretation and potential applicability as described above, TVI analysis does not fit the mold of traditional risk modeling. Regression models are commonly used to define risk by identifying isolated factors that may inform an outcome of interest (see, e.g., Tolles & Meurer, JAMA, 316, 533-534, 2016). The goal of such models is to identify risk factors that maintain their relationship to outcome despite patient differences. In contrast, the TVI leverages patient differences towards generating a time and context-dependent signal during surgery. The approach presented in this example maps complex physiology over the perioperative period to identify common trajectories taken by patients from admission to outcome. TVI-related mapping will facilitate a more fundamental understanding of the surgical experience and the development of adverse events as they evolve in real-time.

TVI is a novel method to objectively measure patient physiology. This measure is a general assessment of homeostatic capacity. As TVI indicates reduced capacity, risk of postoperative morbidity and mortality increase. Thus, the TVI value can inform how well a patient can maintain homeostasis in the context of a physical/psychological challenge. There exist many challenges during a surgical experience, TVI will help define how patients differentially respond. This has direct value to understanding patient specific responses to surgery, drugs, infection, care settings, etc. All of these factor into outcome before outcome occurs. Thus, by assessing on how a patient will respond to the most common challenges, TVI can be used to customize patient care to optimize outcome. For example, patients with depressed TVI do not adequately control their blood pressure in the face of surgical challenge. Compared to other TVI groups, these patient frequently fail to meet perioperative guidelines for blood pressure levels. Data shows that these patients are at increased risk of acute kidney injury, a known complication of guideline failure. Thus TVI can be used to predict risk of acute kidney injury, and more broadly TVI describes a patient's ability to meet established standards of care based on their physiologic status/capacity.

Tables

Tables 1A and 1B.

Patient and surgical characteristics between TVI clusters. 5296 distinct surgeries representing 4358 individual patients were included in the study. The three most common surgical specialties and procedures representing each TVI cluster are displayed in Panel B. SD=Standard Deviation.

TABLE 1A

Patient characteristics between TVI clusters.

| Cluster ID | Total Cases | Total Patients | Profiles representing repeat surgery (%) | Mean ASA (SD) | Emergent Cases (% Total) | Mean Age (SD) | Male gender (%) |
|---|---|---|---|---|---|---|---|
| 1 | 961 | 909 | 5.4 | 2.67 (0.72) | 8.0 | 53 (17) | 57.1 |
| 2 | 418 | 415 | 1.0 | 2.55 (0.72) | 5.2 | 51 (17) | 57.1 |
| 3 | 2366 | 2102 | 11.1 | 2.80 (0.79) | 10.7 | 54 (17) | 52.4 |
| 4 | 1043 | 908 | 12.9 | 2.94 (0.86) | 13.7 | 53 (16) | 53.7 |
| 5 | 508 | 491 | 3.3 | 3.07 (0.84) | 11.0 | 55 (16) | 51.0 |

TABLE 1B

Surgical characteristics between TVI clusters.

| Cluster ID | Most common surgical specialty | Most common primary procedure | Median Procedure Length, Hrs |
|---|---|---|---|
| 1 | General (35%), Orthopaedic (21%), Thoracic (10%) | Irrigation and Debridement of Wound (11%), Total Thyroidectomy (4%), Laparoscopic Cholecystectomy (4%) | 1.6 |
| 2 | General (34%), Orthopaedic (18%), Thoracic (13%) | Exploratory Laparotomy (5%), Anterior Spine Cervical Discectomy and Internal Fusion/Fixation (3%), Laparoscopic Colectomy (3%) | 3.6 |
| 3 | General (31%), Orthopaedic (20%), Thoracic (10%) | Irrigation and Debridement of Wound (12%), Exploratory Laparotomy (4%), Total Thyroidectomy (3%) | 1.5 |
| 4 | General (34%), Orthopaedic (17%), Cardiac (10%) | Irrigation and Debridement of Wound (14%), Exploratory Laparotomy (9%), Parathyoid Exploration (3%) | 1.3 |

TABLE 1B-continued

Surgical characteristics between TVI clusters.

| Cluster ID | Most common surgical specialty | Most common primary procedure | Median Procedure Length, Hrs |
|---|---|---|---|
| 5 | Cardiac (25%), General (22%), Orthopaedic (14%) | Exploratory Laparotomy (6%), Mitral Valve Repair/Replacement (4%), Aortic Valve Repair/Replacement (4%), CABG (4%) | 3.9 |

Tables 2A and 2B.

Case and patient mortality between TVI patterns. Total cases represent the number of individual surgeries (and thus TVI profiles) within each TVI pattern. Total patients represent the number of individual patients within each TVI pattern. Mortality is reported as a percentage of the total cases or patients within a given pattern. 2 Year survival represents patients that survived the 2 years following their surgery.

TABLE 2A

Case mortality between TVI cluster patterns

| TVI Pattern | Total Cases | 30 Day Mortality (%) | 31 Day-1 Year Mortality (%) | 1 Year-2 Year Mortality (%) | 2 Year Survival |
|---|---|---|---|---|---|
| Elevated | 1379 | 1.5 | 5.4 | 3.3 | 89.8 |
| Mixed | 2366 | 2.6 | 6.7 | 3.8 | 86.9 |
| Depressed | 1551 | 5.7 | 7.5 | 4.3 | 82.5 |

TABLE 2B

Patient mortality between TVI cluster patterns.

| TVI Pattern | Total Patients | 30 Day Mortality (%) | 31 Day-1 Year Mortality (%) | 1 Year-2 Year Mortality (%) | 2 Year Survival |
|---|---|---|---|---|---|
| Elevated | 1296 | 1.4 | 5.7 | 3.2 | 89.7 |
| Mixed | 2103 | 2.3 | 6.5 | 3.8 | 87.5 |
| Depressed | 1338 | 4.9 | 7.2 | 4.2 | 83.9 |

TABLE 3

Descriptive statistics of variable-cluster groups shown in FIG. 5.

| Variable | Count | Min | Max | Range | Median | Mean | SE. mean | CI. mean. 0.95 | Var | Std. Dev | Coef. Var |
|---|---|---|---|---|---|---|---|---|---|---|---|
| MAP1 | 5049 | −1.80 | 5.35 | 7.15 | 0.11 | 0.24 | 0.012 | 0.024 | 0.768 | 0.877 | 3.626 |
| MAP2 | 9148 | −2.13 | 5.33 | 7.46 | 0.11 | 0.25 | 0.009 | 0.017 | 0.690 | 0.831 | 3.377 |
| MAP3 | 5124 | −2.88 | 5.84 | 8.73 | −0.15 | 0.02 | 0.012 | 0.023 | 0.709 | 0.842 | 49.006 |
| MAP4 | 4527 | −3.29 | 7.95 | 11.25 | −0.35 | −0.23 | 0.012 | 0.023 | 0.648 | 0.805 | −3.482 |
| MAP5 | 8236 | −2.61 | 6.13 | 8.74 | −0.44 | −0.34 | 0.008 | 0.016 | 0.556 | 0.746 | −2.193 |
| BIS1 | 3711 | −3.13 | 5.31 | 8.44 | 0.23 | 0.38 | 0.016 | 0.032 | 1.002 | 1.001 | 2.646 |
| BIS2 | 7569 | −3.28 | 5.31 | 8.60 | 0.32 | 0.39 | 0.010 | 0.020 | 0.757 | 0.870 | 2.260 |
| BIS3 | 3507 | −3.72 | 5.34 | 9.06 | −0.08 | 0.02 | 0.015 | 0.030 | 0.828 | 0.910 | 57.237 |
| BIS4 | 3481 | −3.77 | 4.90 | 8.67 | −0.39 | −0.34 | 0.016 | 0.032 | 0.902 | 0.950 | −2.757 |
| BIS5 | 6749 | −3.78 | 5.31 | 9.09 | −0.39 | −0.35 | 0.012 | 0.023 | 0.944 | 0.972 | −2.750 |
| MAC1 | 4497 | −2.87 | 6.29 | 9.16 | 0.35 | 0.22 | 0.016 | 0.031 | 1.141 | 1.068 | 4.864 |
| MAC2 | 8590 | −2.87 | 5.88 | 8.75 | 0.74 | 0.60 | 0.011 | 0.021 | 1.000 | 1.000 | 1.668 |
| MAC3 | 4464 | −2.87 | 3.66 | 6.53 | 0.05 | −0.08 | 0.014 | 0.028 | 0.925 | 0.962 | −12.069 |
| MAC4 | 3956 | −2.87 | 3.82 | 6.69 | −0.37 | −0.52 | 0.015 | 0.029 | 0.872 | 0.934 | −1.812 |
| MAC5 | 7329 | −2.87 | 3.58 | 6.45 | −0.58 | −0.64 | 0.010 | 0.019 | 0.687 | 0.829 | −1.303 |
| TVI1 | 3617 | −3.86 | 6.31 | 10.17 | 0.81 | 0.85 | 0.018 | 0.035 | 1.178 | 1.085 | 1.279 |
| TVI2 | 7507 | −3.75 | 6.54 | 10.29 | 1.31 | 1.31 | 0.012 | 0.023 | 1.071 | 1.035 | 0.792 |
| TVI3 | 3342 | −4.71 | 5.34 | 10.05 | −0.09 | −0.08 | 0.016 | 0.031 | 0.832 | 0.912 | −10.810 |
| TVI4 | 3267 | −6.04 | 3.51 | 9.54 | −1.12 | −1.14 | 0.020 | 0.039 | 1.293 | 1.137 | −1.000 |
| TVI5 | 6301 | −7.83 | 5.02 | 12.85 | −1.37 | −1.40 | 0.013 | 0.025 | 1.001 | 1.001 | −0.713 |

MAP1 = All MAP Z-scores in 400 randomly selected TVI profiles in cluster 1.

Count = Total number of data points.

SE. mean = Standard Error of the Mean,

CI. mean. 0.95 = 95% Confidence Interval of the Mean,

Var = Variance,

Coef. Var = Variation Coefficient (SE/Mean).

TABLE 4

Descriptive statistics of select hypnotic medications administered within sampled TVI profiles in FIG. 5 (400 randomly selected TVI profiles from each cluster). Number of Cases represents the number of cases where "x" medication was administered at least once.

|  | No. of Cases | Min | Max | Median | Mean | SE. Mean | CI. Mean. 0.95 | Var | Std. Dev | Coef. Var |
|---|---|---|---|---|---|---|---|---|---|---|
| Midazolam | | | | | | | | | | |
| Cluster1 | 339 | 0 | 9 | 2 | 1.98 | 0.05 | 0.10 | 0.81 | 0.90 | 0.45 |
| Cluster2 | 352 | 0 | 20 | 2 | 2.22 | 0.07 | 0.14 | 1.91 | 1.38 | 0.62 |
| Cluster3 | 323 | 0 | 10 | 2 | 2.01 | 0.06 | 0.12 | 1.28 | 1.13 | 0.56 |
| Cluster4 | 333 | 0 | 15 | 2 | 2.20 | 0.09 | 0.18 | 2.68 | 1.64 | 0.74 |
| Cluster5 | 339 | 0 | 20 | 2 | 3.23 | 0.16 | 0.31 | 8.25 | 2.87 | 0.89 |
| Dexmedetomidine | | | | | | | | | | |
| Cluster1 | 82 | 0 | 224.24 | 26 | 36.29 | 4.23 | 8.41 | 1464.02 | 38.26 | 1.05 |
| Cluster2 | 71 | 0 | 405.77 | 24 | 55.12 | 9.40 | 18.74 | 6270.74 | 79.19 | 1.44 |
| Cluster3 | 77 | 4 | 160 | 40 | 45.07 | 4.30 | 8.57 | 1426.99 | 37.78 | 0.84 |
| Cluster4 | 54 | 8 | 530.83 | 40 | 50.67 | 11.22 | 22.51 | 6800.21 | 82.46 | 1.63 |
| Cluster5 | 51 | 8 | 351.33 | 32 | 44.66 | 7.80 | 15.66 | 3100.78 | 55.68 | 1.25 |
| Etomidate | | | | | | | | | | |
| Cluster1 | 26 | 10 | 40 | 20 | 21.00 | 1.29 | 2.67 | 43.60 | 6.60 | 0.31 |
| Cluster2 | 8 | 20 | 26 | 20 | 21.25 | 0.84 | 1.99 | 5.64 | 2.38 | 0.11 |
| Cluster3 | 29 | 0 | 40 | 20 | 18.86 | 1.70 | 3.48 | 83.69 | 9.15 | 0.49 |
| Cluster4 | 30 | 0 | 50 | 16 | 17.90 | 1.70 | 3.49 | 87.20 | 9.34 | 0.52 |
| Cluster5 | 81 | 0 | 100 | 20 | 18.74 | 1.25 | 2.49 | 127.24 | 11.28 | 0.60 |
| Propofol | | | | | | | | | | |
| Cluster1 | 395 | 0 | 4347.36 | 180 | 213.05 | 13.92 | 27.38 | 76586.99 | 276.74 | 1.30 |
| Cluster2 | 400 | 12 | 1931.25 | 200 | 218.43 | 8.87 | 17.45 | 31502.54 | 177.49 | 0.81 |
| Cluster3 | 398 | 0 | 1842 | 160 | 190.80 | 8.98 | 17.66 | 32098.28 | 179.16 | 0.94 |
| Cluster4 | 393 | 0 | 3740.18 | 150 | 225.45 | 19.40 | 38.14 | 147934.97 | 384.62 | 1.71 |
| Cluster5 | 388 | 0 | 4592.25 | 159.2 | 293.47 | 25.60 | 50.33 | 254285.16 | 504.27 | 1.72 |
| Ketamine | | | | | | | | | | |
| Cluster1 | 37 | 10 | 200 | 40 | 45.28 | 5.75 | 11.65 | 1221.31 | 34.95 | 0.77 |
| Cluster2 | 55 | 10 | 250 | 50 | 56.30 | 5.28 | 10.59 | 1534.20 | 39.17 | 0.70 |
| Cluster3 | 24 | 10 | 50 | 22.5 | 27.08 | 2.31 | 4.78 | 128.08 | 11.32 | 0.42 |
| Cluster4 | 9 | 20 | 120 | 50 | 51.11 | 10.86 | 25.04 | 1061.11 | 32.57 | 0.64 |
| Cluster5 | 11 | 20 | 80 | 50 | 48.18 | 6.30 | 14.03 | 436.36 | 20.89 | 0.43 |

SE. Mean = Standard Error of the Mean,
CI. Mean. 0.95 = 95% Confidence Interval of the Mean,
Var = Variance,
Coef. Var = Variation Coefficient (SE/Mean).

TABLE 5

Descriptive statistics of select opioid medications administered within sampled TVI profiles in FIG. 5 (400 randomly selected TVI profiles from each cluster). Number of Cases represents the number of cases where "x" medication was administered at least once.

|  | No. of Cases | Min | Max | Median | Mean | SE. Mean | CI. Mean. 0.95 | Var | Std. Dev | Coef. Var |
|---|---|---|---|---|---|---|---|---|---|---|
| Remifentanil | | | | | | | | | | |
| Cluster1 | 20 | 340 | 8806.13 | 3600.10 | 3909.26 | 453.46 | 949.10 | 4112536.54 | 2027.94 | 0.52 |
| Cluster2 | 21 | 1494.81 | 15024.1 | 4238.10 | 5154.60 | 818.57 | 1707.51 | 14071221.33 | 3751.16 | 0.73 |
| Cluster3 | 27 | 501.6 | 11802.45 | 3192.00 | 3341.72 | 453.00 | 931.16 | 5540741.46 | 2353.88 | 0.70 |
| Cluster4 | 23 | 246 | 6143.2 | 2416.30 | 2607.75 | 373.19 | 773.95 | 3203278.83 | 1789.77 | 0.69 |
| Cluster5 | 52 | 428.8 | 15594.6 | 3122.40 | 3839.30 | 428.34 | 859.94 | 9540913.43 | 3088.84 | 0.80 |
| Fentanil | | | | | | | | | | |
| Cluster1 | 390 | 50 | 1650 | 250.00 | 285.36 | 8.77 | 17.25 | 30012.48 | 173.24 | 0.61 |
| Cluster2 | 392 | 0 | 1250 | 262.50 | 375.78 | 10.61 | 20.86 | 44109.63 | 210.02 | 0.56 |
| Cluster3 | 390 | 0 | 19210.42 | 250.00 | 321.37 | 49.57 | 97.45 | 958191.41 | 978.87 | 3.05 |
| Cluster4 | 388 | 0 | 23466.66 | 250.00 | 331.12 | 60.97 | 119.88 | 1442533.23 | 1201.06 | 3.63 |
| Cluster5 | 391 | 0 | 3226.66 | 275.00 | 447.36 | 18.71 | 36.79 | 136877.61 | 369.97 | 0.83 |
| Hydromorphone | | | | | | | | | | |
| Cluster1 | 124 | 0.25 | 18 | 1.60 | 1.99 | 0.18 | 0.35 | 3.80 | 1.95 | 0.98 |
| Cluster2 | 245 | 0.2 | 24 | 2.00 | 2.56 | 0.15 | 0.30 | 5.54 | 2.35 | 0.92 |
| Cluster3 | 101 | 0.2 | 8 | 1.50 | 1.87 | 0.13 | 0.26 | 1.77 | 1.33 | 0.71 |

TABLE 5-continued

Descriptive statistics of select opioid medications administered within sampled TVI profiles in FIG. 5 (400 randomly selected TVI profiles from each cluster). Number of Cases represents the number of cases where "x" medication was administered at least once.

|  | No. of Cases | Min | Max | Median | Mean | SE. Mean | CI. Mean. 0.95 | Var | Std. Dev | Coef. Var |
|---|---|---|---|---|---|---|---|---|---|---|
| Cluster4 | 74 | 0.4 | 8 | 1.90 | 2.12 | 0.19 | 0.38 | 2.65 | 1.63 | 0.77 |
| Cluster5 | 144 | 0.1 | 12 | 1.60 | 2.33 | 0.17 | 0.34 | 4.23 | 2.06 | 0.88 |

SE. Mean = Standard Error of the Mean,
CI. Mean. 0.95 = 95% Confidence Interval of the Mean,
Var = Variance,
Coef. Var = Variation Coefficient (SE/Mean).

TABLE 6

Descriptive statistics of select vasopressor medications administered within sampled TVI profiles in FIG. 5 (400 randomly selected TVI profiles from each cluster). Number of Cases represents the number of cases where "x" medication was administered at least once.

|  | No. of Cases | Min | Max | Median | Mean | SE. Mean | CI. Mean. 0.95 | Var | Std. Dev | Coef. Var |
|---|---|---|---|---|---|---|---|---|---|---|
| Ephedrine | | | | | | | | | | |
| Cluster1 | 215 | 0 | 100 | 10.00 | 11.92 | 1.05 | 2.07 | 236.28 | 15.37 | 1.29 |
| Cluster2 | 248 | 0 | 240 | 10.00 | 16.29 | 1.38 | 2.71 | 470.39 | 21.69 | 1.33 |
| Cluster3 | 244 | 0 | 480 | 10.00 | 16.48 | 2.24 | 4.41 | 1225.18 | 35.00 | 2.12 |
| Cluster4 | 231 | 0 | 80 | 10.00 | 12.68 | 0.92 | 1.81 | 194.72 | 13.95 | 1.10 |
| Cluster5 | 235 | 0 | 90 | 10.00 | 15.62 | 1.15 | 2.27 | 311.10 | 17.64 | 1.13 |
| Vasopressin | | | | | | | | | | |
| Cluster1 | 18 | 0 | 31.02 | 5 | 7.50 | 1.74 | 3.67 | 54.56 | 7.39 | 0.98 |
| Cluster2 | 13 | 0.5 | 84.77 | 6 | 15.56 | 6.88 | 14.98 | 614.73 | 24.79 | 1.59 |
| Cluster3 | 31 | 0 | 101.92 | 4 | 8.69 | 3.26 | 6.66 | 329.41 | 18.15 | 2.09 |
| Cluster4 | 59 | 0 | 407.93 | 5.24 | 19.26 | 7.79 | 15.59 | 3579.59 | 59.83 | 3.11 |
| Cluster5 | 126 | 0 | 1065.48 | 8 | 33.50 | 11.85 | 23.44 | 17681.43 | 132.97 | 3.97 |
| Norepinephrine | | | | | | | | | | |
| Cluster1 | 12 | 0 | 2986.8 | 1006.66 | 1215.44 | 292.40 | 643.57 | 1025986.64 | 1012.91 | 0.83 |
| Cluster2 | 10 | 25.6 | 4457.04 | 867.42 | 1489.98 | 489.94 | 1108.33 | 2400436.08 | 1549.33 | 1.04 |
| Cluster3 | 26 | 0 | 6651.12 | 377.97 | 951.77 | 303.19 | 624.44 | 2390071.99 | 1545.99 | 1.62 |
| Cluster4 | 70 | 0 | 6138 | 653.49 | 1072.09 | 136.61 | 272.53 | 1306390.19 | 1142.97 | 1.07 |
| Cluster5 | 113 | 0 | 22748 | 705.16 | 1390.42 | 235.94 | 467.49 | 6290599.71 | 2508.11 | 1.80 |
| Phenylephrine | | | | | | | | | | |
| Cluster1 | 269 | 0 | 21392 | 320.00 | 1607.33 | 194.99 | 383.91 | 10227890.61 | 3198.11 | 1.99 |
| Cluster2 | 312 | 0 | 30250 | 480.00 | 1994.82 | 217.45 | 427.86 | 14752631.38 | 3840.92 | 1.93 |
| Cluster3 | 302 | 0 | 89283.8 | 400.00 | 1696.42 | 333.04 | 655.37 | 33495769.27 | 5787.55 | 3.41 |
| Cluster4 | 325 | 0 | 14760.32 | 480.00 | 1071.81 | 104.96 | 206.50 | 3580713.50 | 1892.28 | 1.77 |
| Cluster5 | 343 | 0 | 38285.48 | 800.00 | 2136.04 | 207.20 | 407.54 | 14724958.53 | 3837.31 | 1.80 |
| Epinephrine | | | | | | | | | | |
| Cluster1 | 9 | 0 | 3735.61 | 101.48 | 783.37 | 444.49 | 1024.98 | 1778103.04 | 1333.46 | 1.70 |
| Cluster2 | 7 | 0.2 | 1505.32 | 20.00 | 233.65 | 212.05 | 518.87 | 314759.35 | 561.03 | 2.40 |
| Cluster3 | 23 | 5 | 3088 | 302.82 | 661.40 | 172.40 | 357.54 | 683623.61 | 826.82 | 1.25 |
| Cluster4 | 54 | 0 | 6703 | 276.73 | 693.20 | 158.10 | 317.10 | 1349692.24 | 1161.76 | 1.68 |
| Cluster5 | 116 | 0 | 12159 | 473.73 | 934.93 | 144.34 | 285.91 | 2416676.29 | 1554.57 | 1.66 |

SE. Mean = Standard Error of the Mean,
CI. Mean. 0.95 = 95% Confidence Interval of the Mean,
Var = Variance,
Coef. Var = Variation Coefficient (SE/Mean).

TABLE 7

Descriptive statistics of select fluids administered within sampled TVI profiles in FIG. 5 (400 randomly selected TVI profiles from each cluster). Number of Cases represents the number of cases where "x" fluid was administered at least once.

|  | No. of Cases | Min | Max | Median | Mean | SE. Mean | CI. Mean. 0.95 | Var | Std. Dev | Coef. Var |
|---|---|---|---|---|---|---|---|---|---|---|
| NS 0.9% | | | | | | | | | | |
| Cluster1 | 398.00 | 0.00 | 7000.00 | 1000.00 | 1313.49 | 47.03 | 92.46 | 880411.25 | 938.30 | 0.71 |
| Cluster2 | 400.00 | 100.00 | 7945.83 | 1875.00 | 2094.89 | 57.56 | 113.17 | 1325471.50 | 1151.29 | 0.55 |

TABLE 7-continued

Descriptive statistics of select fluids administered within sampled TVI profiles in FIG. 5 (400 randomly selected TVI profiles from each cluster). Number of Cases represents the number of cases where "x" fluid was administered at least once.

|  | No. of Cases | Min | Max | Median | Mean | SE. Mean | CI. Mean. 0.95 | Var | Std. Dev | Coef. Var |
|---|---|---|---|---|---|---|---|---|---|---|
| Cluster3 | 400.00 | 0.00 | 4853.75 | 1000.00 | 1209.75 | 38.93 | 76.53 | 606224.23 | 778.60 | 0.64 |
| Cluster4 | 399.00 | 0.00 | 5700.00 | 1000.00 | 1081.39 | 40.17 | 78.98 | 643931.58 | 802.45 | 0.74 |
| Cluster5 | 400.00 | 0.00 | 6500.00 | 1630.84 | 1901.27 | 55.07 | 108.27 | 1213144.75 | 1101.43 | 0.58 |
| Albumin 5% | | | | | | | | | | |
| Cluster1 | 127 | 100 | 4000 | 750.00 | 927.66 | 58.54 | 115.86 | 435279.20 | 659.76 | 0.71 |
| Cluster2 | 220 | 0 | 4000 | 1000.00 | 1019.82 | 43.39 | 85.51 | 414157.71 | 643.55 | 0.63 |
| Cluster3 | 136 | 0 | 3750 | 500.00 | 829.04 | 45.17 | 89.34 | 277502.04 | 526.78 | 0.64 |
| Cluster4 | 139 | 0 | 2250 | 500.00 | 813.22 | 41.71 | 82.48 | 241836.06 | 491.77 | 0.60 |
| Cluster5 | 252 | 0 | 7000 | 1000.00 | 1037.06 | 51.77 | 101.95 | 675278.18 | 821.75 | 0.79 |
| Plasma-Lyte A | | | | | | | | | | |
| Cluster1 | 15 | 0 | 1900 | 0.00 | 126.67 | 126.67 | 271.67 | 240666.67 | 490.58 | 3.87 |
| Cluster2 | 11 | 0 | 1562.5 | 0.00 | 183.26 | 143.89 | 320.61 | 227749.88 | 477.23 | 2.60 |
| Cluster3 | 14 | 0 | 1000 | 0.00 | 171.43 | 95.17 | 205.61 | 126813.19 | 356.11 | 2.08 |
| Cluster4 | 10 | 0 | 1000 | 0.00 | 184.49 | 103.69 | 234.55 | 107506.45 | 327.88 | 1.78 |
| Cluster5 | 12 | 0 | 3200 | 0.00 | 410.45 | 264.28 | 581.68 | 838126.96 | 915.49 | 2.23 |
| Lactated Ringers | | | | | | | | | | |
| Cluster1 | 35 | 0 | 2800 | 200.00 | 372.72 | 97.22 | 197.58 | 330833.82 | 575.18 | 1.54 |
| Cluster2 | 57 | 0 | 3400 | 700.00 | 903.15 | 106.86 | 214.08 | 650945.47 | 806.81 | 0.89 |
| Cluster3 | 38 | 0 | 2400 | 411.67 | 584.50 | 107.49 | 217.80 | 439080.64 | 662.63 | 1.13 |
| Cluster4 | 25 | 0 | 2000 | 300.00 | 492.20 | 100.34 | 207.09 | 251687.67 | 501.68 | 1.02 |
| Cluster5 | 44 | 0 | 2956.67 | 400.00 | 527.59 | 87.03 | 175.50 | 333227.80 | 577.26 | 1.09 |

SE. Mean = Standard Error of the Mean,
CI. Mean. 0.95 = 95% Confidence Interval of the Mean,
Var = Variance,
Coef. Var = Variation Coefficient (SE/Mean).

Example 2

The Triple Variable Index Identifies Intraoperative Blood Pressure Trajectories that Link Inhaled Anesthetic Response to Hypotension Exposure This example shows that patients exhibit distinct responses to inhaled anesthesia and illustrates use of the Triple Variable Index to classify risk of an IOH event in a surgical patient receiving an inhaled anesthetic.

Inhaled anesthetics are a mainstay in current clinical practice and whose pharmacodynamics are well established. Inhaled anesthetics produce dose-dependent effects on the cardiovascular system. Sevoflurane, isoflurane, and desflurane are potent vasodilators and myocardial depressants. Nitrous oxide, a common adjuvant used together with these volatile agents, is a myocardial depressant but may also increase systemic vascular resistance when administered at elevated concentrations. Many patient and procedure-related factors, such as age, anemia, body temperature, acute ethanol intoxication, and administered intraoperative medications, alter the potency of inhaled anesthetics. As a result, the cardiovascular effects of inhaled anesthesia are difficult to anticipate for a given patient or type of surgery.

Intraoperative hypotension (IOH) is common and even modest exposure increases a patient's risk of serious, costly complications, including acute kidney injury and myocardial infarction, and even postoperative death. Although inhaled anesthetics have clear effects on intraoperative blood pressure levels, the relationship between inhaled anesthetic administration and IOH exposure has not been previously evaluated. Specifically, it remains unknown how IOH exposure varies between patients that demonstrate distinct responses to inhaled anesthetics.

Disclosed herein is an index that combines mean arterial blood pressure (MAP), Bispectral Index (BIS), and minimum alveolar concentration (MAC) data into a single variable, called the Triple Variable Index (TVI), that can be mapped across the intraoperative period. Three unique TVI expression patterns are identified: "elevated", "mixed", and "depressed," which are distinguished by the specific combinations of MAP, BIS, and MAC levels that occurred together across time. Thus, TVI can be applied as a tool to 1) define expression patterns as distinct responses to inhaled anesthesia, 2) identify such responses within a large surgical population, and 3) assess how differences in response relate to IOH exposure. Of the three observed patterns, patients that demonstrated a depressed pattern achieved the lowest MAP and BIS levels despite their exposure to the lowest MAC levels. It is believed that IOH exposure varies between patients demonstrating distinct responses to inhaled anesthetics and responses characterized by depressed TVI expression experience greater IOH exposure compared to other expression patterns.

This example provides TVI data using retrospective MAP, BIS, and MAC data from a large, diverse surgical population, including both cardiac and noncardiac surgery patients. Blood pressure levels over time and key IOH characteristics, including prevalence across multiple MAP thresholds, frequency, depth, intraoperative location, and exposure associated with individual IOH events, were compared between TVI expression patterns. How patient and procedure-related factors such as TVI expression and intraoperative duration translate to overall IOH exposure were examined for individual procedures.

Material and Methods

Study Population.

Surgeries that took place at University of Pittsburgh Medical Center (UPMC) Presbyterian and Montefiore hospitals were evaluated for study inclusion. Surgeries were included in the study if the patient undergoing surgery was at least 18 years old. Surgeries involving patients younger than 18 years old were excluded from further analysis.

Data Extraction.

Intraoperative data was collected for the following variables for each study surgery from the electronic health record systems at UPMC: MAP, end tidal concentration of inhaled anesthetics (isoflurane, desflurane, sevoflurane, nitrous oxide), BIS (Quatro Sensor, Covidien, Minneapolis, Minn.), administered medications, date of surgery, procedure length, and type of surgery. Non-invasive blood pressure measurements may be distinguished from invasive blood pressure measurements in the system due to distinct documentation. For each patient of each surgery ASA Physical Status, age, and gender was obtained.

TVI Generation and Expression Analysis.

Raw MAP, BIS, and end tidal inhaled anesthetic concentration data were processed in the following ways prior to TVI generation. If arterial line and noninvasive MAP measurements were recorded simultaneously, arterial line measurements were used for analysis. Each end tidal concentration recorded was converted to a MAC value using standard 1 MAC equivalents: isoflurane=1.17%, desflurane=6.6%, sevoflurane=1.8%, and nitrous oxide=105% (see, e.g., Nickalls and Mapleson, Br J Anaesth 91, 170-174, 2003). At times when multiple inhaled agents were used together, a total MAC value was calculated by summing individual agents' 1 MAC equivalents. For the purposes of this example, the term 'MAC' refers to the summed MAC values representing all inhaled anesthetics at a given measurement in time. MAC values were not age-adjusted. Inhaled anesthetics were considered to be used any time a summed MAC value was greater than 0.001; values less than this were considered clinically negligible. Extreme values, reflecting artifacts in the data, were removed. The limits were defined as MAP values greater than 250 or less than 10 mmHg, MAC values greater than 3, and BIS values greater than 100 or less than 1.

Following MAC value generation and artifact removal, MAP, BIS, and MAC data were normalized using a z-score. A z-score was calculated for each individual measurement relative to the total distribution of values that existed for that variable in the study population. MAP, BIS, and MAC data were not measured at the same frequency, thus were aggregated using a non-overlapping, sliding window approach (Zeileis and Grothendieck. J Statistical Software, 14(6), 1-27, 2005). For each variable, an average value was calculated within sequential windows, each defined as five consecutive measurements where MAP, BIS, or inhaled anesthetics were monitored as single variables or in combination, starting at the beginning of the monitoring period. In surgeries where five measurements were not available at the end of the monitoring period, an average value was calculated for the last window using the remaining measurements. A TVI value was generated for each window by summing z-scores of MAP, BIS, and MAC variables if data from all three variables existed. TVI values were not generated, by definition, for windows lacking data for any one of the MAP, BIS, or MAC variables. Inhaled anesthetic administration during cardiopulmonary bypass is recorded by a perfusionist at UPMC and not captured by the electronic anesthesia record system. TVI values were not generated for these periods due to a lack of available MAC data.

Figure 15:
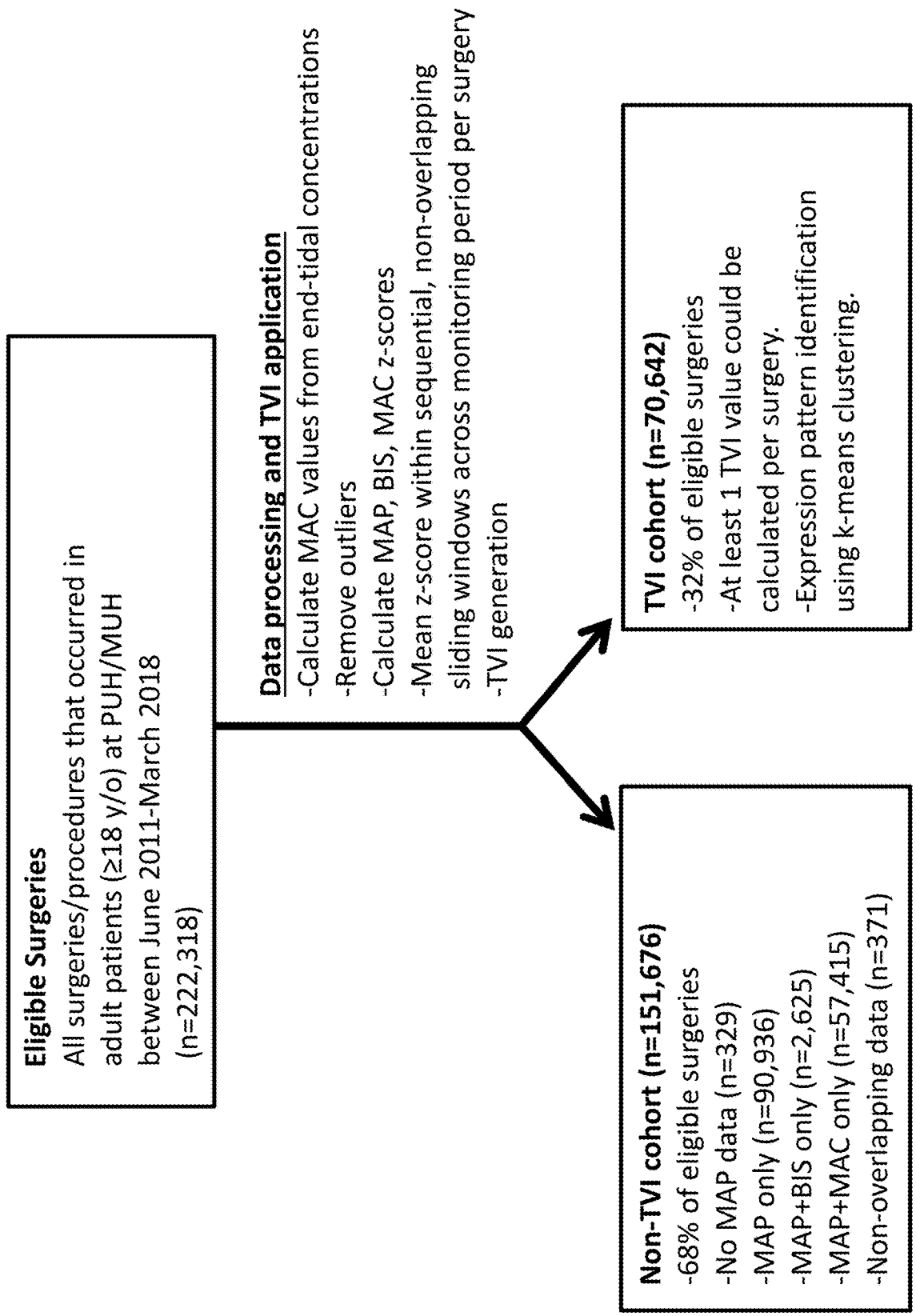
FIG. 15: Flowchart illustrating workflow for analysis of perioperative surgery parameters.

Not all study surgeries were capable of generating TVI data due to missing MAP, BIS, or MAC data or a lack of concurrent monitoring (see FIG. 15). For surgeries where TVI data was generated, a TVI profile, representing the total TVI values mapped across windows, was created. As discussed in Example 1, profiles are k-means clustered to identify those sharing similar patterns of TVI expression across the intraoperative period. Clustering was performed using 3 centroids, 10 random starts, and 100 maximum iterations. A randomly selected sample of 500 individual profiles were identified and visually compared. In this plot, "red" color represents a TVI signal above 0 and a "blue" color represents a TVI signal below 0. TVI values of 0 do not exist in the dataset. The color "white" represents a window where TVI signal could not be generated due to nonexistent (monitoring not taking place) or incomplete MAP, BIS, MAC data.

Statistical Analysis.

Descriptive statistics were calculated for the patient, procedure, anesthetic (including intraoperative medications), and TVI characteristics. Means were calculated for normally distributed variables and presented with 95% confidence intervals and standard deviation values. Medians were calculated for non-normally distributed variables and presented with 95% confidence intervals and $1^{st}$-$3^{rd}$ quartiles. Ninety-five percent confidence intervals were generated for medians by identifying 0.025, 0.975 percentiles across 10,000 bootstrapped samples. Proportions were presented with 95% confidence intervals except those calculated for the most commonly observed surgical specialties. Variable distributions were compared using boxplots and histograms. For each boxplot, upper and lower whiskers represent maximum and minimum values, respectively. Upper and lower hinges represent $3^{rd}$ and $1^{st}$ quartiles, respectively. The horizontal, bold line represents the median value. MAP, BIS, MAC and TVI data were plotted across time using a generalized additive model (GAM) with cubic regression splines and Gaussian distributions. The same model, using a binomial distribution, was employed to plot the fraction of MAP measurements below 65 mmHg across time.

The proportion of MAP measurements below three thresholds, 65, 60, and 55 mmHg, were compared between TVI expression patterns of all surgeries. For all subsequent analyses, an IOH event represented any MAP measurement below 65 mmHg. For all identified IOH events in each expression pattern, the median number of events per surgery, the median MAP level, and the proportion of total IOH events within each quarter of the intraoperative period were calculated. Medians were reported with 95% confidence intervals and $1^{st}$ and $3^{rd}$ quartiles. Individual IOH events were compared between patterns by extracting the MAP measurements that occurred 10 minutes before and after each event. MAP levels were plotted across this time interval using the GAM model described above. IOH exposure was calculated as the area defined by the time and depth MAP levels were below 65 mmHg (point-minutes).

TVI expression was evaluated in surgeries of individual procedures. All study surgeries were subsetted into groups based on their procedure ID and TVI expression. All procedure-expression groups containing 10 or more surgeries were selected for analysis. Data for the following variables were calculated for each procedure-expression group: total number of surgeries, median length of the intraoperative period, mean MAP, proportion of MAP measurements below 65 mmHg, median MAP of IOH events, median IOH events per surgery, proportion of IOH events in $1^{st}$, $2^{nd}$ and $4^{th}$ quarters of the intraoperative period. Median and means were reported with $1^{st}$ and $3^{rd}$ quartile and standard deviations, respectively. MAP levels and IOH characteristics were compared as described above between only those procedures represented by all three TVI expression patterns.

duration, non-emergent, and related to a gastrointestinal procedure compared to those of the TVI cohort. The non-TVI cohort exhibited statistically higher average intraoperative MAP (84.4 vs 81.7 mmHg) and MAC (0.86 vs 0.82) levels but lower BIS (40.0 vs 41.4) levels compared to the TVI cohort.

TABLE 8

Patient, procedure, MAP, BIS, and MAC characteristics between TVI and non-TVI cohorts.

| Variable | Non-TVI cohort | TVI cohort |
|---|---|---|
| Total Surgeries (% of eligible surgeries) | 151,676 (68) | 70,642 (32) |
| % ASA Physical Status 1 (95% CI) | 3.2 (3.2-3.3) | 3.7 (3.6-3.9) |
| % ASA Physical Status 2 (95% CI) | 31.2 (31.0-31.4) | 27.5 (27.2-27.9) |
| % ASA Physical Status 3 (95% CI) | 53.4 (53.2-53.7) | 48.2 (47.9-48.6) |
| % ASA Physical Status 4 (95% CI) | 11.4 (11.3-11.6) | 19.4 (19.2-19.7) |
| % ASA Physical Status 5 (95% CI) | 0.004 (0.004-0.005) | 0.01 (0.009-0.01) |
| % ASA Physical Status 6 (95% CI) | 0.001 (0.001-0.002) | 0 |
| % Emergent Surgery (95% CI) | 6.0 (5.9-6.1) | 16.3 (16.0-16.5) |
| Mean Age, years (SD, 95% CI) | 56 (17, ±0.1) | 54 (17, ±0.1) |
| % Male Gender (95% CI) | 52.4 (52.2-52.7) | 55.4 (55.0-55.7) |
| Most common surgical specialty (%) | 1. GI (34.4)<br>2. Neurologic (13.4)<br>3. Orthopedic (10.5)<br>4. General (7.2)<br>5. Thoracic (5.9) | 1. General (31.4)<br>2. Orthopedic (18.7)<br>3. Thoracic (10.9)<br>4. Cardiac (7.2)<br>5. Neurologic (6.9) |
| Median Length of Procedure, Hr (Q1-Q3, 95% CI) | 0.6 (0.3-1.4, 0.6-0.7) | 1.7 (0.9-3.3, 1.6-1.9) |
| Mean MAP, mmHg (SD, 95% CI) | 84.4 (17.9, ±0.02) | 81.7 (17.4, ±0.02) |
| Mean BIS (SD, 95% CI) | 40.0 (16.3, ±0.1) | 41.4 (10.8, ±0.01) |
| Mean MAC (SD, 95% CI) | 0.86 (0.30, ±0.0004) | 0.82 (0.30, ±0.0004) |

Next, how TVI expression in combination with other factors relates to overall IOH exposure for specific procedures was examined. For this analysis, IOH exposure for a given procedure was defined as the median number of IOH events that occur per surgery. All procedure-expression groups that shared the same exposure were identified at four different thresholds: 4, 5, 6, and 7 IOH events per surgery. For each threshold, the procedure-expression groups were plotted as a function of their median intraoperative duration (x-axis) and proportion of MAPs below 65 mmHg (y-axis). In these plots, each procedure was color-coded according to its associated TVI expression pattern and a line of best fit was created using the GAM model described above. Finally, intraoperative duration and proportion of MAPs below 65 mmHg was compared between two groups of procedures using boxplots: those associated with an elevated expression pattern that exhibited a median of five or more IOH events per surgery versus those associated with a depressed pattern that exhibited a median of less than five IOH events per surgery.

All above analyses were completed using RStudio Version 1.0.143 (R-project.org).

Results

Figure 16:
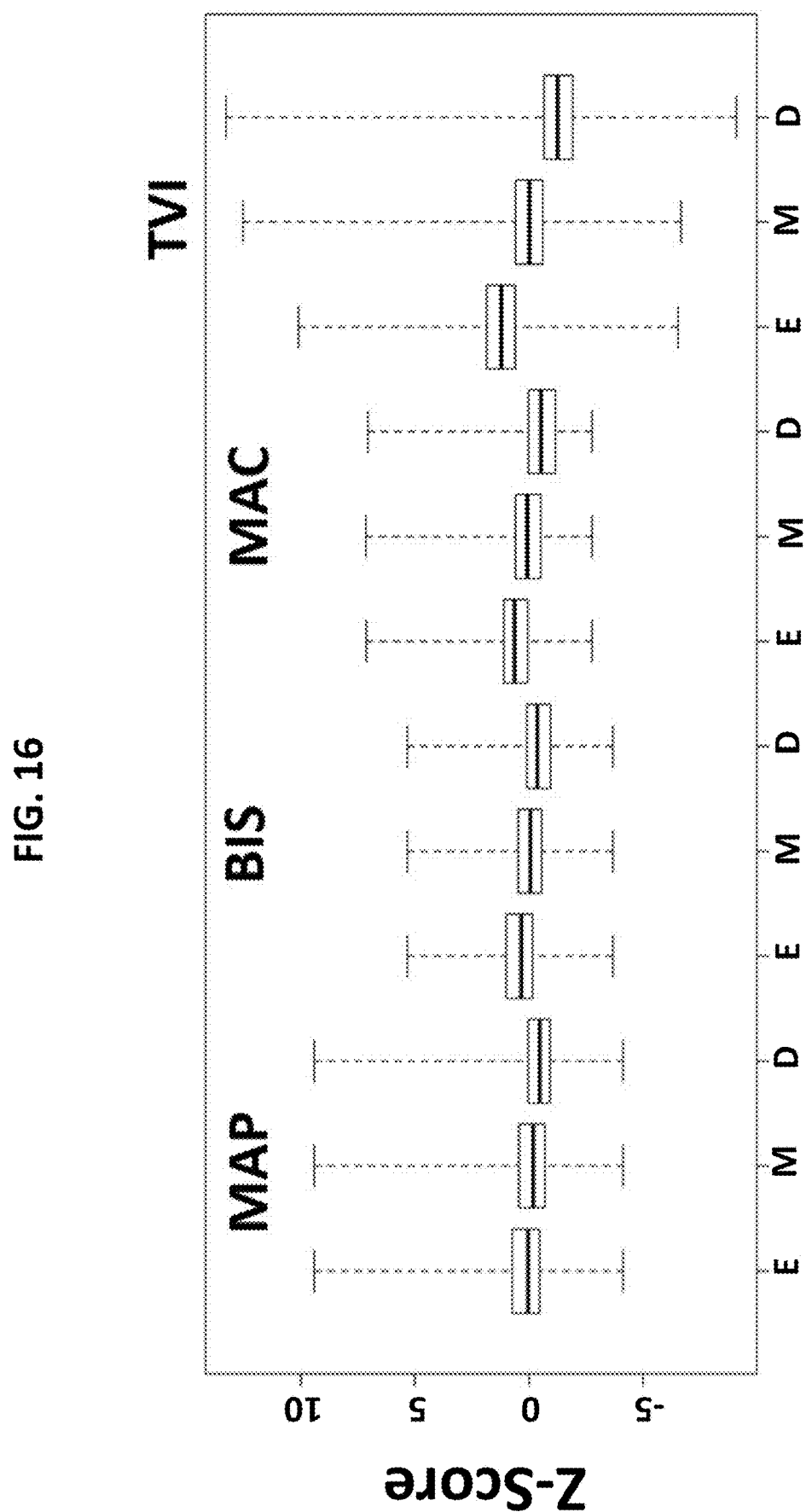
FIG. 16: Comparison of MAP, BIS, MAC, and TVI distributions between elevated (E), mixed (M), and depressed (D) TVI expression patters.
Figure 17A:
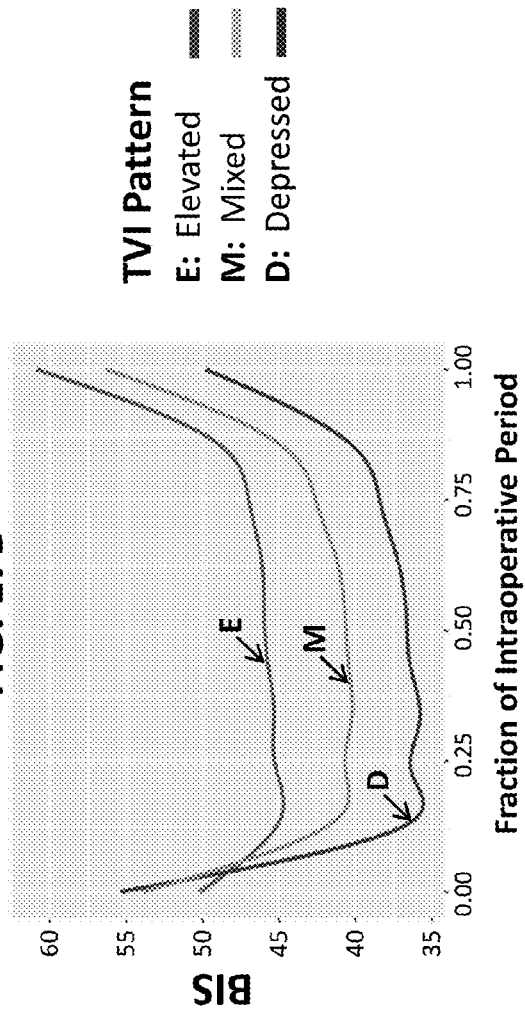
FIGS. 17A-17D: MAP, BIS, MAC, and TVI intraoperative trajectories for elevated (E), mixed (M), and depressed (D) TVI expression patterns.
Figure 17B:
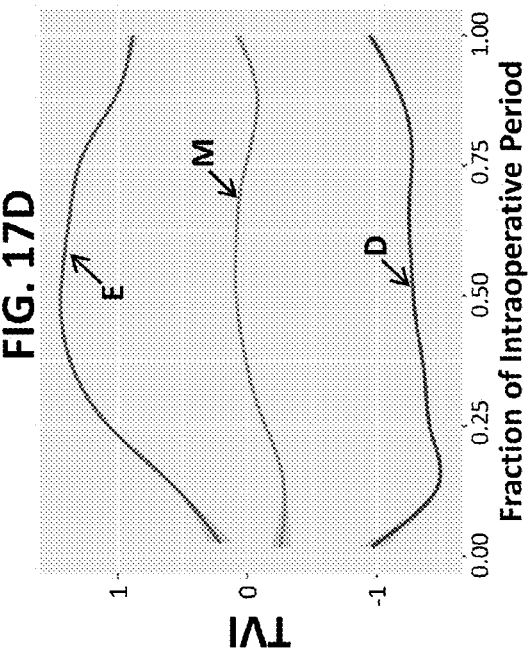
Figure 17C:
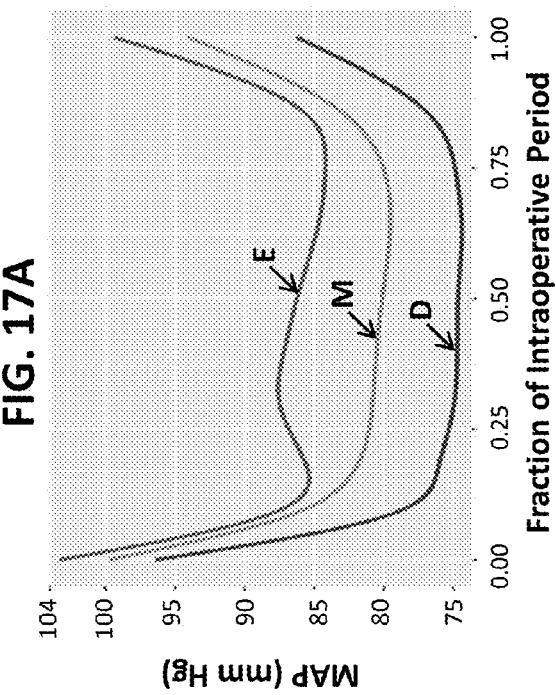
Figure 17D:
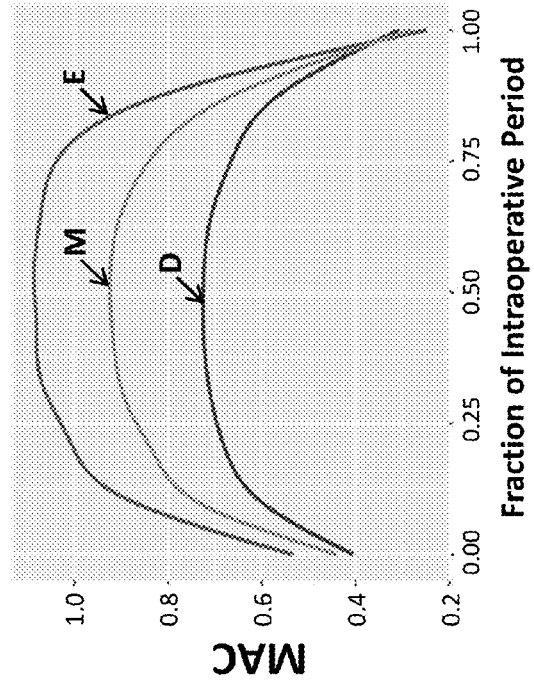

FIG. 15 depicts the selection of study surgeries from those that were eligible in the study period (n=222,318). The TVI cohort, 32% of all eligible surgeries, represents adult patients for whom TVI data was generated from concurrent MAP, BIS, and MAC monitoring. For the majority of eligible surgeries (68%), TVI data could not be generated due to missing or non-overlapping data. Missing MAC and/or BIS data were the most common reasons TVI data could not be generated from an eligible surgery. The non-TVI cohort was characterized by lower ASA physical status scores, increased age, and a higher proportion of female patients compared to TVI cohort (see Table 8). Also, surgeries in the non-TVI cohort were more likely to be short in Using k-means clustering, surgeries in the TVI cohort were distinguished into groups based on their TVI expression. FIG. 16 shows the distributions of MAP, BIS, MAC and TVI levels between the three identified expression patterns, elevated (E), mixed (M), and depressed (D). TVI expression is distinguished between patterns as a function of all three composite variables. The elevated pattern is characterized by relatively high MAP and BIS levels in combination with relatively high MAC levels. Mixed and depressed patterns are characterized by lower combined MAP, BIS, and MAC levels. In other words, patients demonstrating an elevated expression pattern achieved the highest MAP and BIS levels while being administered the highest doses of inhaled anesthetics. Patients demonstrating a mixed pattern achieved lower MAP and BIS levels with a lower dose of inhaled agents, and patients that expressed a depressed pattern achieved the lowest MAP and BIS levels while being given the lowest doses of inhaled anesthetics. Each pattern demonstrates a clear response to inhaled anesthetics that is distinct from the others.

Table 9 shows the patient, procedure, and TVI characteristics of each pattern. In sequence from the elevated to the mixed to the depressed pattern, the average MAP, BIS, MAC, and TVI levels demonstrated during surgery were as follows: 87.0, 82.4, 76.6 mmHg for MAP, 46.4, 41.7, 37.5 for BIS, 0.99, 0.83, 0.66 for MAC, and 1.22, −0.004, −1.30 for TVI. Differences between patterns for each variable were statistically significant (p<0.05). The elevated pattern was characterized by the lowest assigned ASA physical status scores, the youngest patients, and the largest proportion of male patients compared to the other patterns. The depressed pattern was characterized in the opposite fashion: the highest assigned ASA physical status scores, the oldest patients, and the highest proportion of female patients. For each of these characteristics, the mixed pattern fell between elevated and depressed pattern patients.

TABLE 9

Patient, procedure, and TVI characteristics of each identified TVI expression pattern.

| Variable | Elevated | Mixed | Depressed |
|---|---|---|---|
| Total Surgeries | 12,005 (17.0) | 40,301 (57.0) | 18,336 (26.0) |
| % ASA Physical Status 1 (95% CI) | 4.2 (3.9-4.6) | 4.1 (3.9-4.3) | 2.7 (2.5-3.0) |
| % ASA Physical Status 2 (95% CI) | 36.0 (35.2-36.9) | 28.3 (27.8-28.7) | 20.4 (19.8-21.0) |
| % ASA Physical Status 3 (95% CI) | 52.9 (52.0-53.8) | 49.6 (49.1-50.1) | 42.2 (41.5-43.0) |
| % ASA Physical Status 4 (95% CI) | 6.7 (6.3-7.2) | 17.3 (16.9-17.6) | 32.6 (31.9-33.3) |
| % ASA Physical Status 5 (95% CI) | 0.0006 (0.0003-0.001) | 0.008 (0.007-0.009) | 2.1 (1.9-2.3) |
| % Emergent Surgery (95% CI) | 9.8 (9.3-10.3) | 16.2 (15.8-16.5) | 20.8 (20.2-21.4) |
| Mean Age, years (SD, 95% CI) | 53.3 (17, ±0.3) | 54.2 (17.1, ±0.2) | 55.2 (16.4,, ±0.2) |
| % Male Gender (95% CI) | 57.6 (56.7-58.5) | 55.8 (55.3-56.3) | 53.0 (52.2-53.7) |
| Most common surgical specialty (%) | 1. General (32.8) 2. Orthopedic (21.3) 3. Thoracic (10.8) 4. Neurologic (9.2) 5. Otolaryngology (6.7) | 1. General (31.6) 2. Orthopedic (20.1) 3. Thoracic (11.4) 4. Neurologic (7.1) 5. Plastic (5.4) | 1. General (30.1) 2. Cardiac (16.1) 3. Orthopedic (14.0) 4. Thoracic (10.1) 5. Transplant (7.4) |
| Median Length of Procedure, hr (Q1-Q3, 95% CI) | 2.4 (1.6-3.8, 2.3-2.6) | 1.4 (0.7-2.7, 1.3-1.5) | 2.1 (1.2-4.0, 1.9-2.3) |
| Arterial line used (%, 95% CI) | 35.2 (34.4-36.1) | 39.9 (39.4-40.3) | 51.5 (50.8-52.2) |
| N2O administered (%, 95% CI) | 23.4 (22.7-24.2) | 17.0 (16.6-17.4) | 11.6 (11.1-12.1) |
| Mean MAP, mmHg (SD, 95% CI) | 87.0 (17.6, ±0.04) | 82.4 (17.3, ±0.02) | 76.6 (16.1, ±0.03) |
| Median frequency of MAP monitoring, minutes per measurement (Q1-Q3, 95% CI) | 3 (2.7-4.4, 2.9-3.1) | 3.3 (2.7-4.7, 3.2-3.5) | 3.8 (2.7-5.0, 3.5-4.0) |
| Mean BIS (SD, 95% CI) | 46.4 (10.5, ±0.03) | 41.7 (10.4, ±0.02) | 37.5 (10.2, ±0.02) |
| Median frequency of BIS monitoring, minutes per measurement (Q1-Q3, 95% CI) | 6.7 (6.1-7.9, 6.7-6.9) | 8.1 (6.7-11.3, 7.9-8.3) | 7.1 (6.2-8.6, 7.0-7.2) |
| Mean MAC (SD, 95% CI) | 0.99 (0.29, ±0.0007) | 0.83 (0.28, ±0.0005) | 0.66 (0.26, ±0.0006) |
| Median frequency of MAC monitoring, minutes per measurement (Q1-Q3, 95% CI) | 5.7 (5.4-6.1, 5.7-5.8) | 6.2 (5.6-7.2, 6.1-6.3) | 6.0 (5.5-7.1, 6.0-6.1) |
| Mean TVI (SD, 95% CI) | 1.22 (1.05, ±0.005) | −0.004 (1.01, ±0.003) | −1.30 (1.05, ±0.005) |
| Median TVI per hr (Q1-Q3, 95% CI) | 5.5 (3.3-6.6, 5.4-5.7) | 5.2 (3.0-7.1, 4.9-5.5) | 4.7 (2.8-6.8, 4.3-5.2) |

Patterns differed according to their procedure-related characteristics. General, orthopedic, thoracic, and neurologic surgery represented more than two-thirds of both elevated and mixed pattern surgeries. General (30.1%), orthopedic (14.0%), and thoracic (10.1%) surgery were commonly associated with the depressed pattern, but so too were cardiac (16.1%) and transplant (7.4%) surgery. More than half of depressed pattern surgeries used an arterial line for MAP monitoring. Nitrous oxide was used in 23.4% of elevated pattern surgeries, the highest proportion of the three patterns. Elevated pattern surgeries were the longest with a median surgical duration of 2.4 hours, while the mixed pattern surgeries were the shortest with a median duration of 1.4 hours. MAP, BIS, and MAC levels were monitored at different frequencies within the study population and ranged from 1 measurement captured every 3 minutes (median MAP monitoring frequency for elevated pattern surgeries) to 1 measurement captured every 8.1 minutes (median BIS monitoring frequency for mixed pattern surgeries).

Intraoperative medications and fluids were differentially administered between TVI expression patterns as shown in Table 10. Propofol, ketamine, dexmedetomidine, hydromorphone, morphine, ephedrine, and beta-blockers were more commonly administered in elevated pattern surgeries than surgeries associated with the other patterns. Etomidate, vasopressors (e.g. phenylephrine, norepinephrine, epinephrine, vasopressin), milrinone, nicardipine, nitroglycerin, and calcium were most commonly administered in depressed pattern surgeries. In elevated and mixed pattern surgeries, the most commonly administered fluids were (in order of frequency of use): normal saline, lactated ringers, and albumin. In the depressed pattern surgeries, albumin was used more frequently over lactated ringers. For both medication and fluid administration, mixed pattern surgeries generally fell between those observed between the elevated and depressed patterns.

TABLE 10

Intraoperative mediation administration for each TVI expression pattern.
Data are presented as the proportion of total surgeries in which a given medication was administered at least once during surgery.

| Variable | Elevated | Mixed | Depressed |
|---|---|---|---|
| Propofol (%, 95% CI) | 96.1 (95.7-96.4) | 90.0 (89.7-90.3) | 83.5 (83.0-84.0) |
| Etomidate (%, 95% CI) | 5.7 (5.3-6.2) | 11.0 (10.7-11.3) | 18.0 (17.4-18.6) |
| Midazolam (%, 95% CI) | 84.2 (83.6-84.9) | 79.1 (78.7-79.5) | 81.1 (80.5-81.6) |
| Ketamine (%, 95% CI) | 14.8 (14.1-15.4) | 6.0 (5.8-6.3) | 3.3 (3.1-3.6) |
| Dexmedetomidine (%, 95% CI) | 15.9 (15.2-16.5) | 12.5 (12.2-12.8) | 9.5 (9.1-9.9) |
| Fentanyl (%, 95% CI) | 94.4 (94.0-94.8) | 95.4 (95.2-95.6) | 95.0 (94.7-95.3) |
| Hydromorphone (%, 95% CI) | 45.6 (44.7-46.5) | 26.3 (25.8-26.7) | 23.5 (22.9-24.1) |
| Remifentanil (%, 95% CI) | 6.0 (5.6-6.5) | 6.2 (5.9-6.4) | 6.9 (6.5-7.3) |

TABLE 10-continued

Intraoperative mediation administration for each TVI expression pattern.
Data are presented as the proportion of total surgeries in which a
given medication was administered at least once during surgery.

| Variable | Elevated | Mixed | Depressed |
|---|---|---|---|
| Morphine (%, 95% CI) | 4.6 (4.2-5.0) | 1.9 (1.8-2.1) | 1.8 (1.6-2.0) |
| Phenylephrine (%, 95% CI) | 55.5 (54.6-56.4) | 58.2 (57.7-58.6) | 70.9 (70.2-71.6) |
| Ephedrine (%, 95% CI) | 40.6 (39.8-41.5) | 35.3 (34.8-35.8) | 35.1 (34.4-35.7) |
| Norepinephrine (%, 95% CI) | 6.6 (6.1-7.0) | 10.1 (9.8-10.4) | 23.0 (22.4-23.6) |
| Vasopressin (%, 95% CI) | 2.1 (1.9-2.4) | 6.2 (5.9-6.4) | 18.5 (17.9-19.1) |
| Epinephrine (%, 95% CI) | 2.2 (2.0-2.5) | 6.9 (6.7-7.2) | 20.3 (19.7-20.8) |
| Dopamine (%, 95% CI) | 1.3 (1.1-1.6) | 1.6 (1.5-1.7) | 3.3 (3.0-3.6) |
| Milrinone (%, 95% CI) | 0.1 (0.0-0.2) | 1.3 (1.2-1.5) | 5.4 (5.1-5.8) |
| Nicardipine (%, 95% CI) | 1.5 (1.3-1.7) | 2.0 (1.9-2.2) | 3.5 (3.2-3.8) |
| Nitroglycerin (%, 95% CI) | 4.9 (4.5-5.3) | 4.9 (4.7-5.1) | 9.2 (8.8-9.7) |
| Esmolol (%, 95% CI) | 10.5 (9.9-11.0) | 7.5 (7.3-7.8) | 6.7 (6.4-7.1) |
| Metoprolol (%, 95% CI) | 7.8 (7.3-8.3) | 4.6 (4.4-4.8) | 4.3 (4.0-4.6) |
| Labetalol (%, 95% CI) | 10.5 (10.0-11.1) | 5.2 (5.0-5.4) | 2.7 (2.5-3.0) |
| Calcium (%, 95% CI) | 18.4 (17.7-19.1) | 18.1 (17.8-18.5) | 33.9 (33.2-34.5) |
| NS 0.9% (%, 95% CI) | 69.3 (68.5-70.1) | 73.8 (73.4-74.2) | 83.6 (83.1-84.2) |
| Lactated Ringers (%, 95% CI) | 47.2 (46.3-48.1) | 36.4 (35.9-36.9) | 26.2 (25.6-26.8) |
| Plasma Lyte A (%, 95% CI) | 24.8 (24.0-25.5) | 16.0 (15.6-16.3) | 14.3 (13.8-14.8) |
| Albumin (%, 95% CI) | 35.2 (34.3-36.1) | 30.2 (29.7-30.6) | 43.6 (42.9-44.3) |
| Hetastarch (%, 95% CI) | 0.4 (0.3-0.5) | 0.3 (0.2-0.3) | 0.5 (0.4-0.6) |

Figure 24:
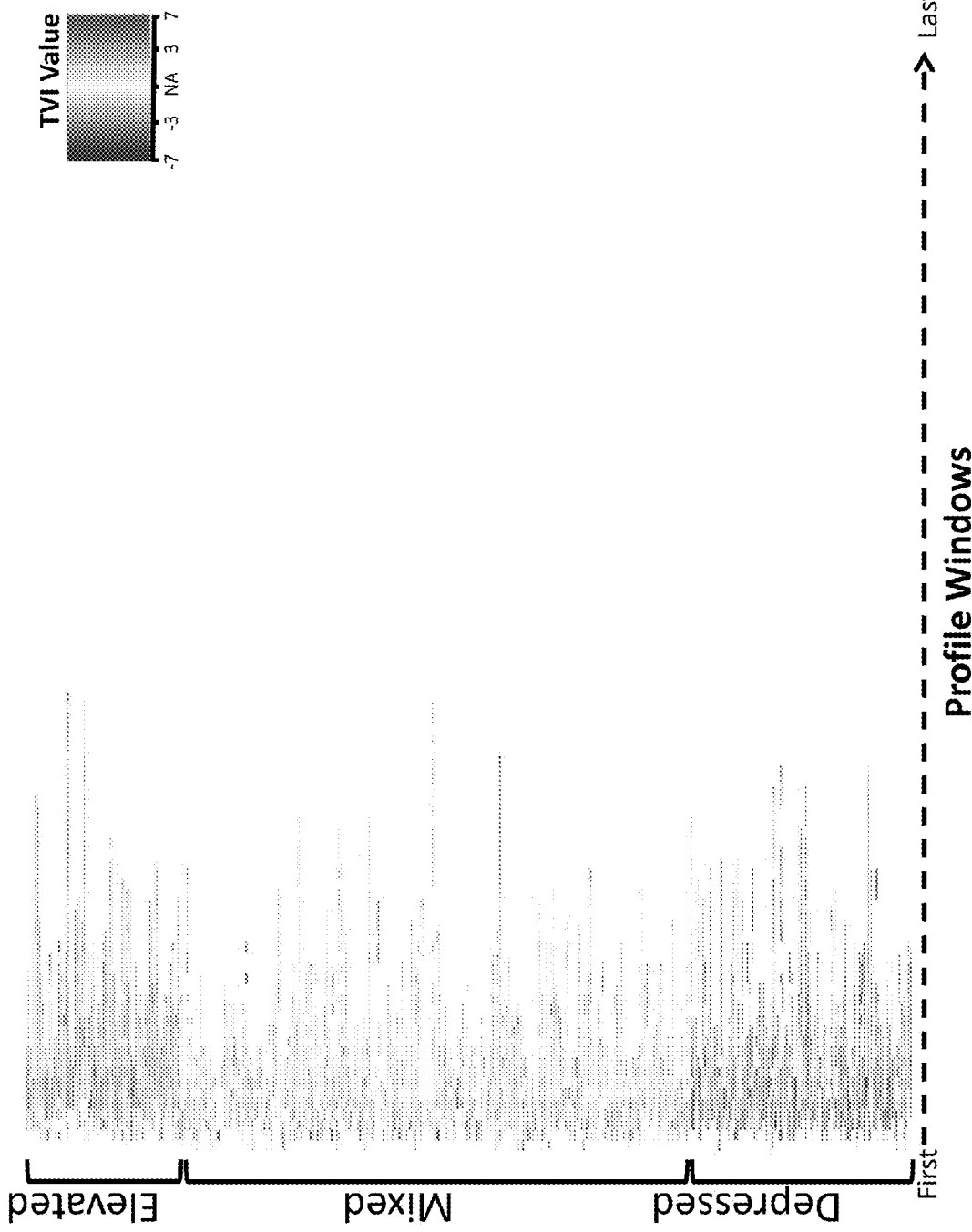
FIG. 24: TVI expression across the intraoperative period for 500 randomly-selected, individual surgeries. TVI expression is plotted along profile windows, not relative intraoperative time. Colors red, blue and white in the plot represent a relatively high, low, and missing TVI values, respectively.

MAP, BIS, MAC, and TVI levels were different between patterns as demonstrated above comparing their overall distributions. These differences were also manifest over intraoperative time. FIGS. 17A-17D show the intraoperative trajectories of each one of these variables. MAP and BIS decreased initially to reach a trough that was roughly maintained until the end of the intraoperative period when the variables increased towards their initial levels. MAC trajectories occurred in the opposite manner with levels increasing to reach a plateau that decreased towards initial levels at the end of the period. In surgeries that exhibited an elevated pattern, TVI expression increased rapidly within the first quarter of the intraoperative period and slowly declined in the last two quarters. In depressed pattern surgeries, expression increased steadily following an initial decrease. Mixed pattern surgeries expressed a TVI signal that fluctuated above and below zero without periods of rapid increases or decreases. FIG. 24 shows TVI expression in a random sample of 500 individual surgeries. Importantly, MAP, BIS, MAC, and TVI trajectories are pattern-specific.

Figure 18:
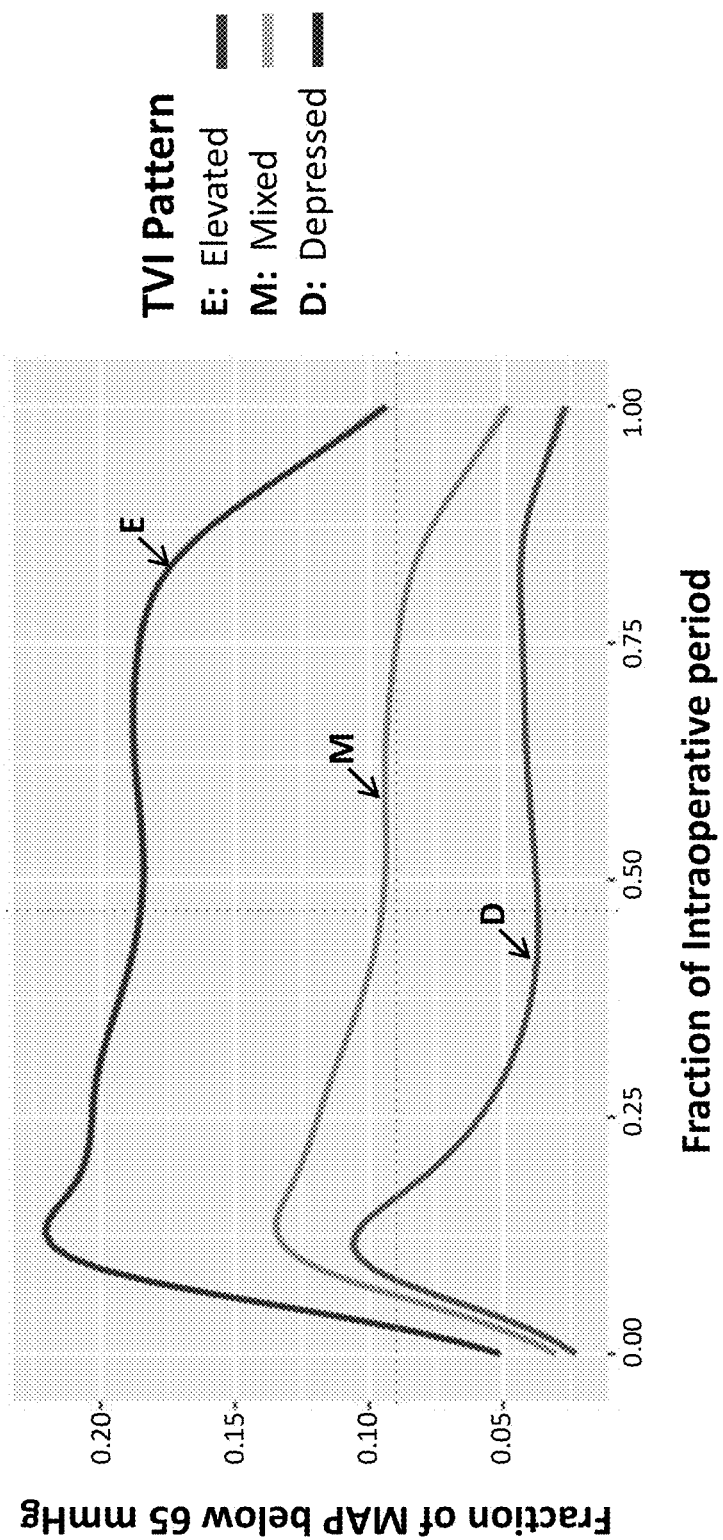
FIG. 18: Estimated fraction of MAP measurements below 65 mmHg across the intraoperative period for each TVI expression pattern.
Figure 20A:
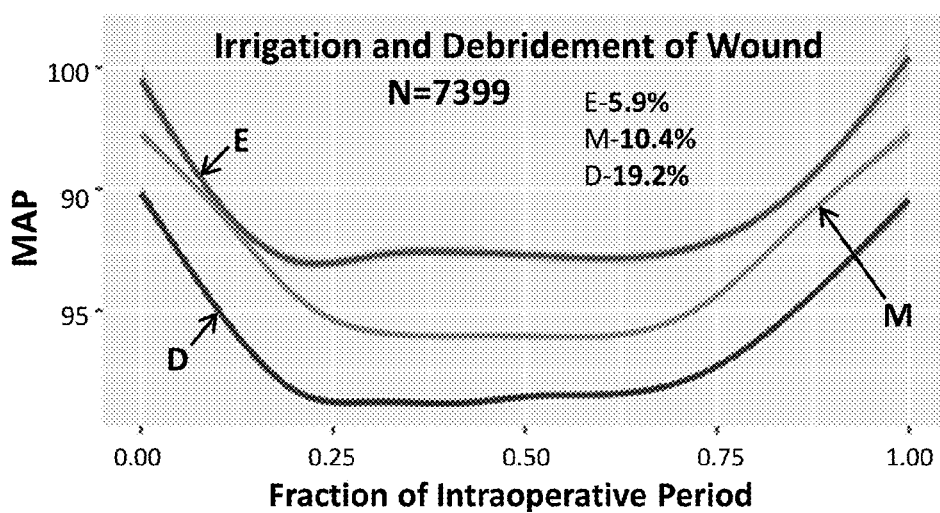
FIGS. 20A-20E: MAP trajectories for each TVI expression pattern in the following procedures: Irrigation and Debridement of Wound, Exploratory Laparotomy, Laparoscopic Cholecystectomy, Total thyroidectomy, and Anterior Cervical Discectomy and Fusion. The proportion of total MAP measurements below 65 mmHg that occurred during surgery are shown. Grey shading represents the 95% CI for each curve.
Figure 20B:
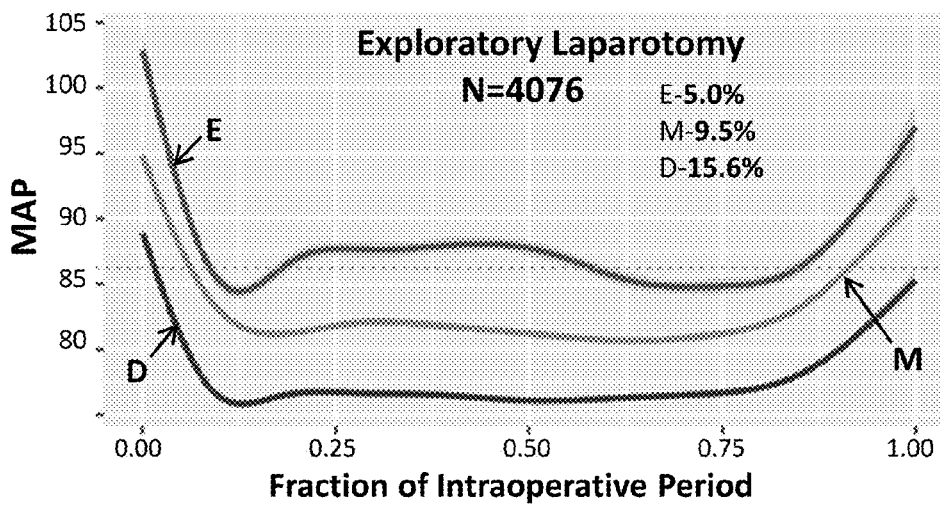
Figure 20C:
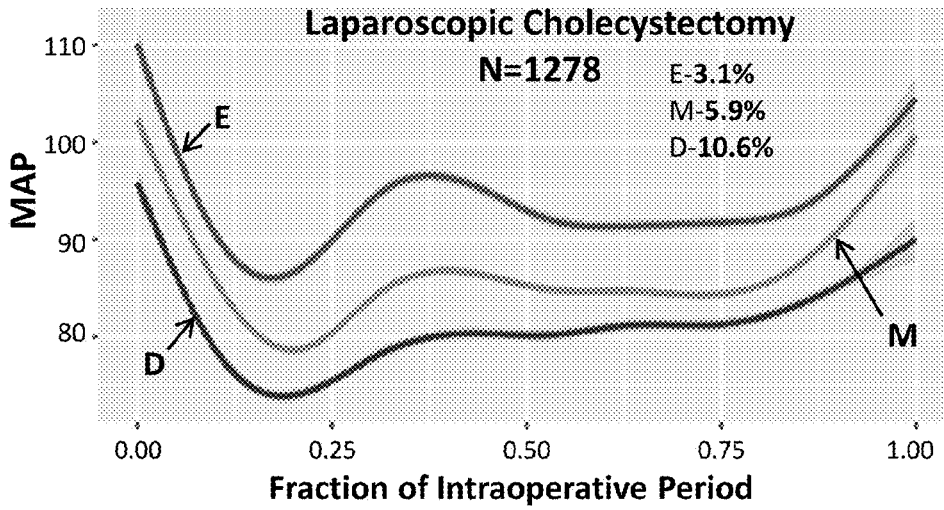
Figure 20D:
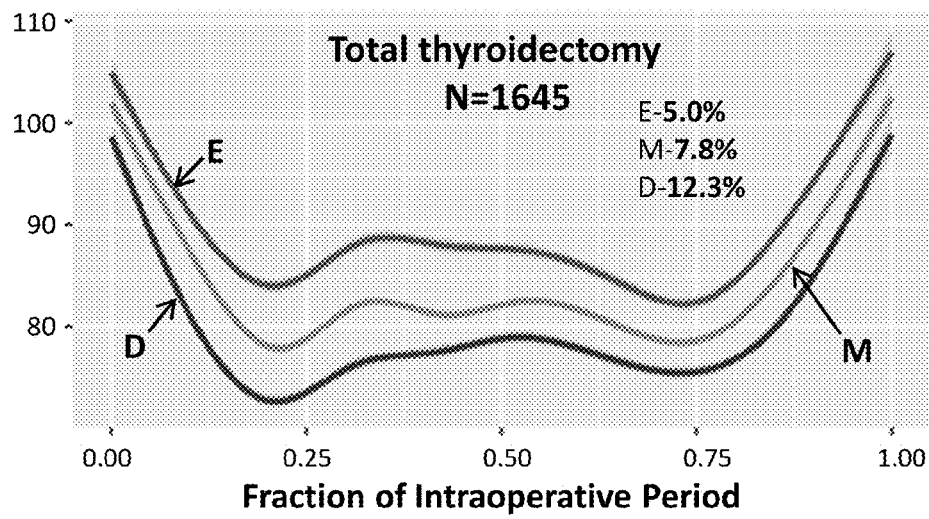
Figure 20E:
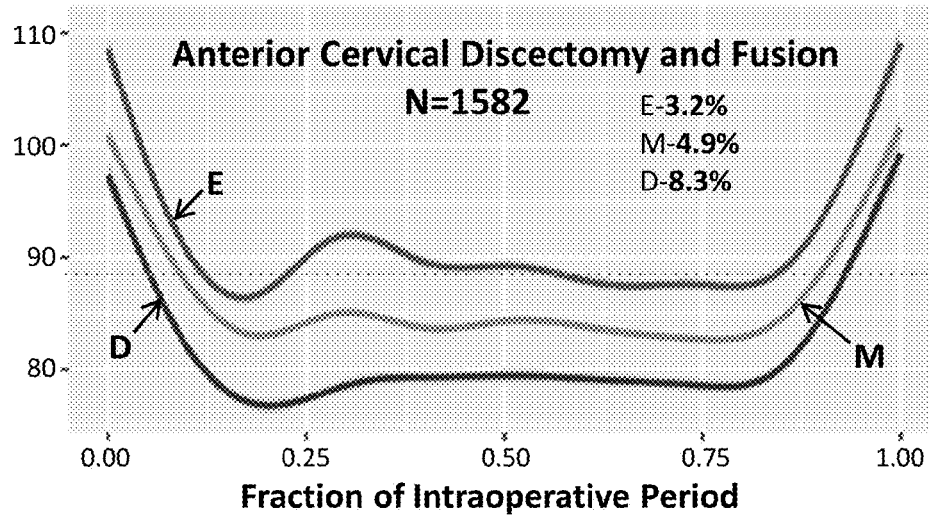
Figure 21A:
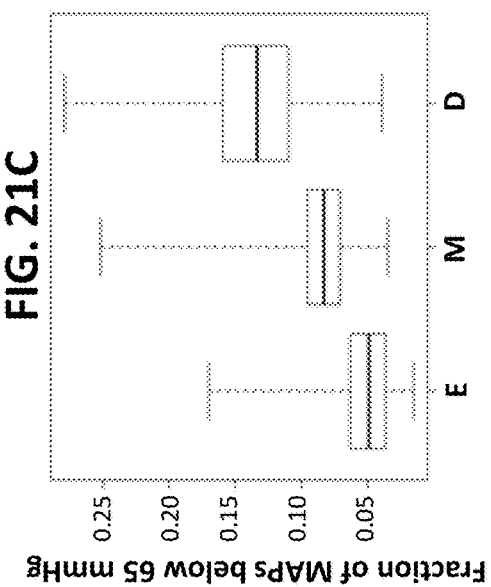
FIGS. 21A-21G: Comparison of IOH-related characteristics between TVI expression patterns in 159 surgical procedures where each pattern occurred in 10 or more surgeries in the examined population.
Figure 21B:
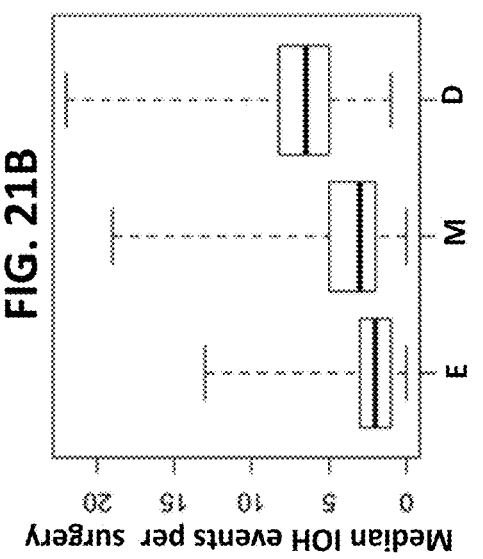
Figure 21C:
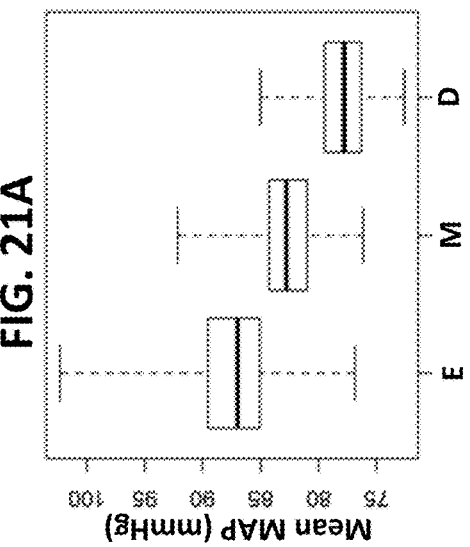
Figure 21D:
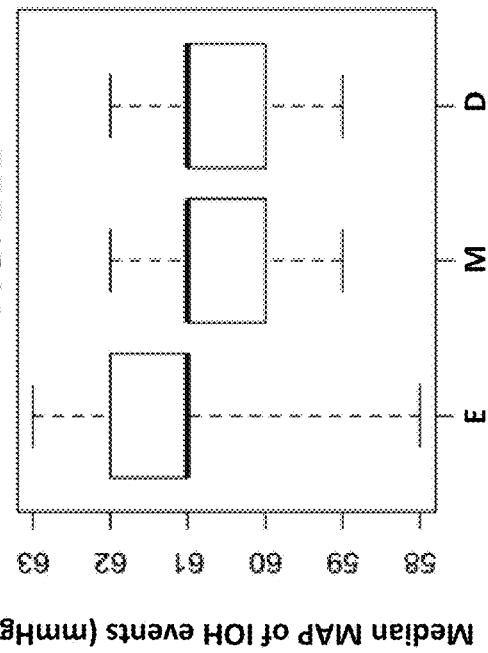
Figure 21E:
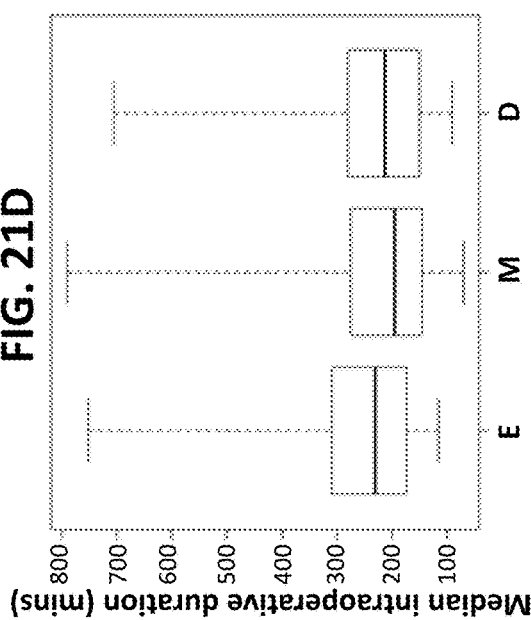
Figure 21F:
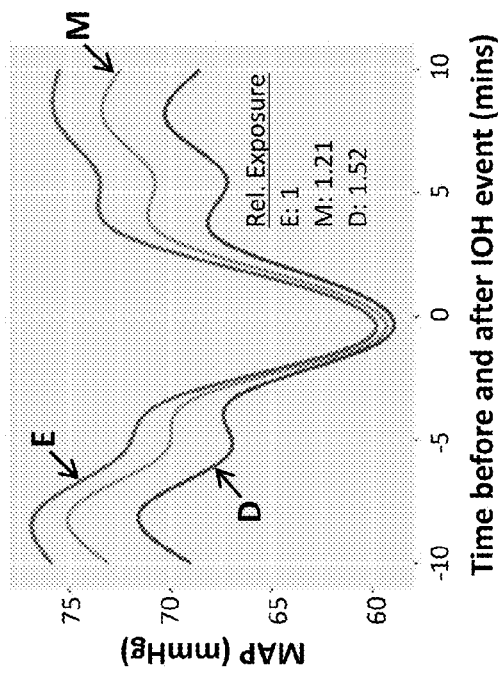
Figure 21G:
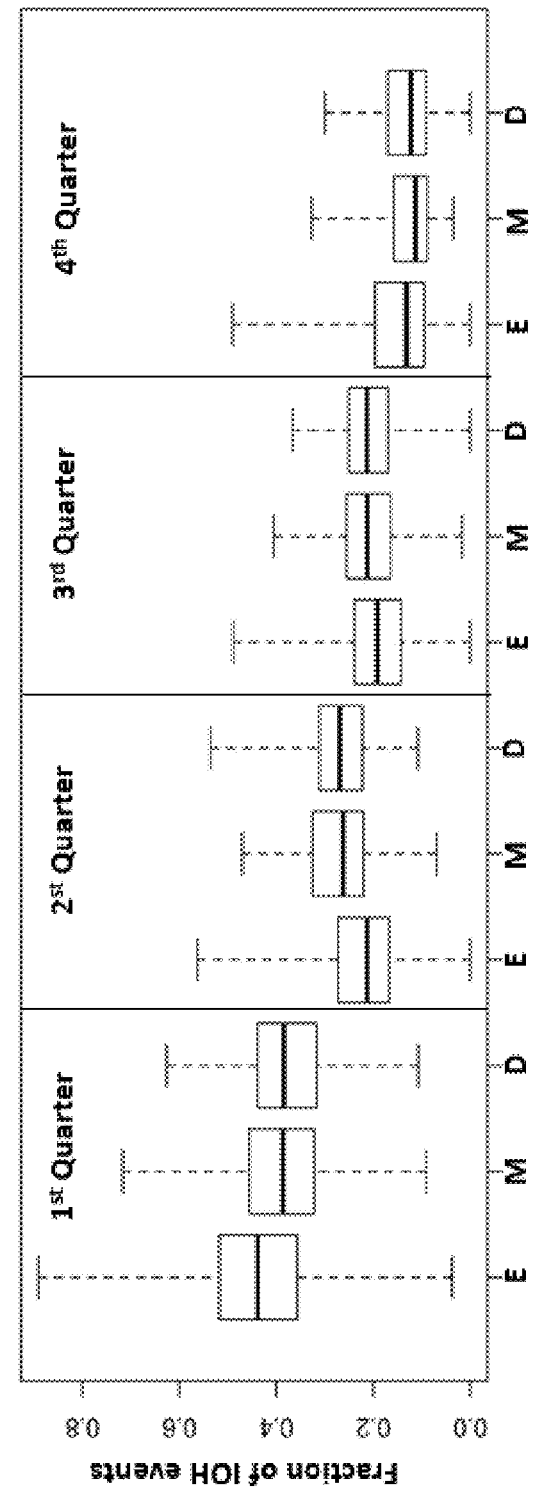
Figure 22A:
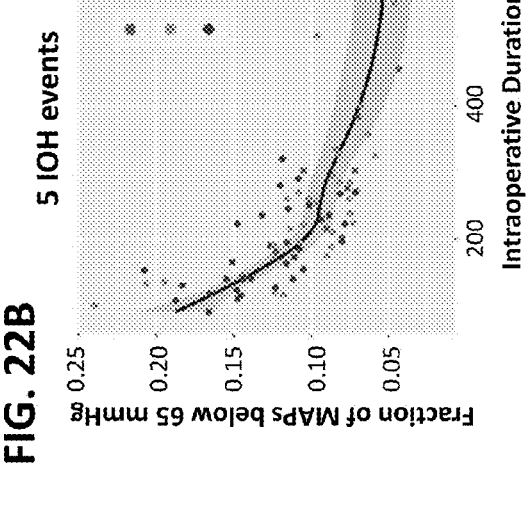
FIGS. 22A-22D: Relationship between length of intraoperative duration and fraction of MAPs below 65 mmHg for groups of procedures that share the same IOH exposure defined as the median number of IOH events that occurred per surgery. Procedures are color-coded according to their associated TVI expression pattern. Intraoperative duration is plotted using median values.
Figure 22B:
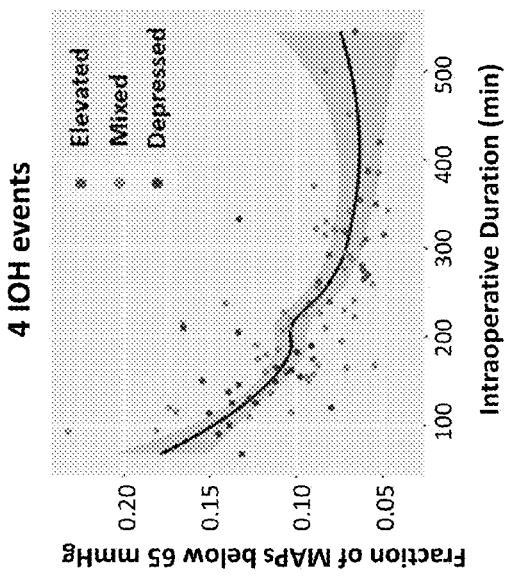
Figure 22C:
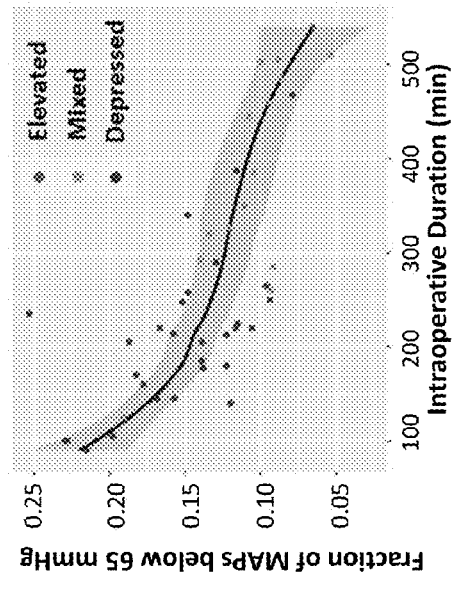
Figure 22D:
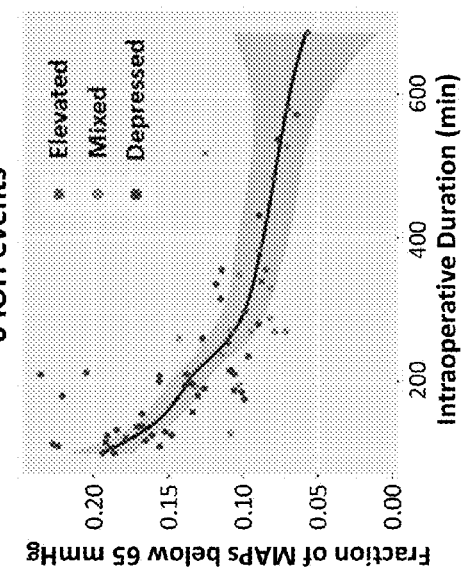

Each pattern's MAP trajectory is associated with unique IOH characteristics. FIG. 18 shows the fraction of MAP levels that were below 65 mmHg across the intraoperative period. For all patterns, the risk of experiencing a MAP below this threshold rapidly increased at the beginning of the period. In surgeries associated with the elevated pattern, IOH risk subsequently decreased and fell below 5% for the remainder of time. IOH risk also decreased in surgeries associated with mixed and depressed patterns, however, this decrease occurred more slowly so that risk remained above 8 and 15%, respectively, until the last quarter of the period.

Table 11 shows the percentage of MAP measurements below three IOH thresholds, 65, 60, and 55 mmHg, the median number of IOH events per surgery (event is defined as a MAP below 65 mmHg), median MAP level of IOH events, and the proportion of events in each quarter of the intraoperative period. FIG. 19A-19D show the MAP levels 10 minutes before and after individual IOH events for each pattern. Surgeries associated with the elevated pattern experienced the smallest proportions of MAP measurements below IOH thresholds (5.1% or less), the fewest IOH events per surgery (2), and the lowest exposure, defined as the time and depth below 65 mmHg, per IOH event (11.8 point-minutes). Surgeries associated with mixed and depressed patterns compared as follows: 9.8% and 18.3% or less MAP measurements below IOH thresholds, 3 and 8 IOH events per surgery, and 14.9 and 19.6 point-minutes of exposure per IOH event. The median MAP level of IOH events was 61 mmHg for the elevated pattern and 60 mmHg for the mixed and depressed patterns. The first quarter of the intraoperative period contained the highest proportion of IOH events in elevated pattern surgeries (41.4%), whereas IOH events were more evenly distributed within the first 3 quarters in mixed (31.3, 28.6, 25.0%) and depressed (27.8, 28.3, 26.7%) pattern surgeries.

TABLE 11

IOH characteristics for each TVI expression pattern. IOH event is defined as any MAP measurement below 65 mmHg.

| Variable | Elevated | Mixed | Depressed |
|---|---|---|---|
| Percent MAP <65 mmHg (95% CI) | 5.1 (5.1-5.2) | 9.8 (9.8-9.9) | 18.3 (18.2-18.3) |
| Percent MAP <60 mmHg (95% CI) | 1.9 (1.8-1.9) | 4.2 (4.1-4.2) | 8.9 (8.8-8.9) |
| Percent MAP <55 mmHg (95% CI) | 0.8 (0.7-0.8) | 1.8 (1.8-1.9) | 4.2 (4.1-4.2) |
| Median IOH events per surgery (Q1-Q3, 95% CI) | 2 (0-5, 1-2) | 3 (0-7, 2-3) | 8 (3-16, 7-9) |
| Median MAP of IOH events, mmHg (Q1-Q3, 95% CI) | 61 (57-63, 61-61) | 60 (56-63, 60-61) | 60 (55-62, 59-60) |
| Proportion of IOH events- $1^{st}$ Quarter (%, 95% CI) | 41.4 (40.9-41.8) | 31.3 (31.1-31.5) | 27.8 (27.6-28.0) |
| Proportion of IOH events- $2^{st}$ Quarter (%, 95% CI) | 21.7 (21.4-22.1) | 28.6 (28.4-28.8) | 28.3 (28.1-28.5) |
| Proportion of IOH events- $3^{st}$ Quarter (%, 95% CI) | 20.5 (20.2-20.9) | 25.0 (24.8-25.2) | 26.7 (26.6-26.9) |
| Proportion of IOH events- $4^{st}$ Quarter (%, 95% CI) | 16.3 (16.0-16.7) | 15.2 (15.0-15.3) | 17.2 (17.0-17.3) |

The type of procedure performed during surgery likely influences the occurrence of IOH events and their associated characteristics. Because TVI patterns do not equally represent the same procedures (Table 9), IOH events were compared between patterns within the same procedures. The MAP trajectories for the five most common procedures performed in the study population are shown in FIGS. 20A-20E. In each procedure, the MAP trajectory associated with the elevated pattern was characterized by the highest MAP levels across the intraoperative period while the trajectory of the depressed pattern was characterized by the lowest MAP levels. Also, trajectories were related to the proportion of MAP measurements that occurred below 65 mmHg Proportions varied between procedures, however the elevated pattern trajectory was associated with the smallest proportion in each procedure and the depressed pattern trajectory was associated with the largest.

159 procedures were identified in which each TVI expression pattern occurred in 10 or more surgeries. MAP levels, duration of the intraoperative period, and IOH characteristics were calculated for each procedure and compared between patterns. Results are shown in FIGS. 21A-21G. In short, the elevated pattern surgeries were associated with the highest MAP levels and characteristics consistent with the lowest IOH exposure. The depressed pattern surgeries were associated with the lowest levels and highest IOH exposure. The relative location of IOH events for each pattern was consistent with the previous analysis using all TVI surgeries displayed in Table 11.

Figure 23A:
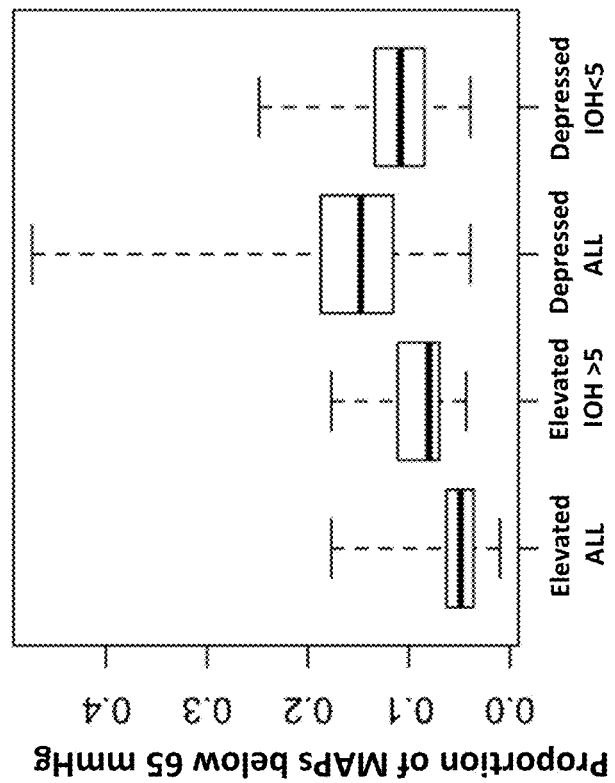
FIGS. 23A and 23B: Comparison of median intraoperative duration and proportion of MAP measurements below 65 mmHg between the following groups of procedures: 1) All procedures associated with the elevated expression pattern (n=211), 2) procedures associated with the elevated pattern and a median number of IOH events per surgery >5 (n=20), 3) All procedures associated with the depressed expression pattern (n=252), and 4) procedures associated with the depressed pattern and a median number of IOH events per surgery <5 (n=44). All procedures included in this analyses were associated with 10 or more individual surgeries.
Figure 23B:
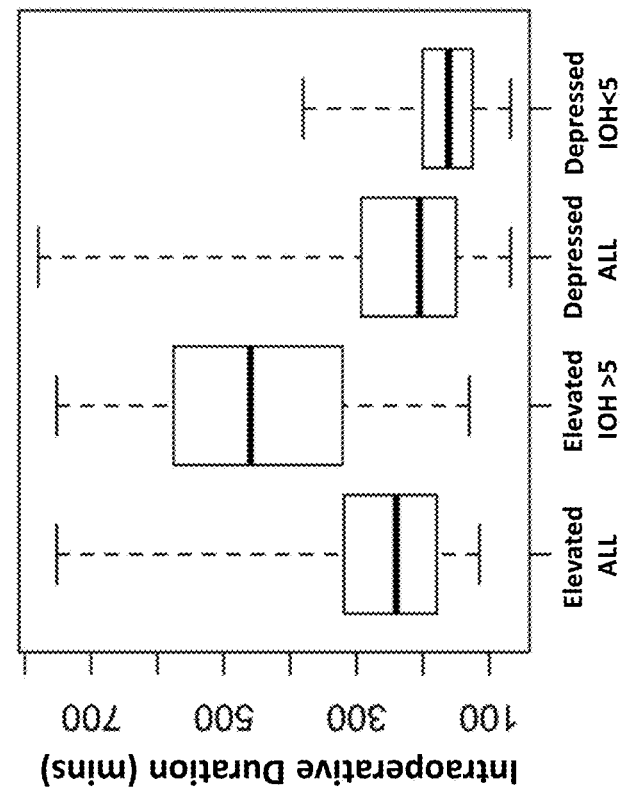

FIGS. 22A-22D show the relationship between the duration of the intraoperative period and proportion of MAP measurements below 65 mmHg for groups of procedures that experienced the same median number of IOH events per surgery. This relationship was examined at four levels of exposure: 4, 5, 6, and 7 IOH events per surgery. For each exposure level, procedures associated with the shortest median intraoperative periods were also associated with the highest proportion of MAP measurements below 65 mmHg. Similarly, procedures associated with the longest median intraoperative periods were associated with the lowest proportion of MAP measurements below 65 mmHg. As shown in FIG. 23, there existed procedures associated with an elevated expression pattern that experienced greater levels of IOH exposure than those associated with a depressed expression pattern. The elevated pattern procedures exhibited a median intraoperative period that was more than twice as long in duration than the depressed pattern procedures.

Discussion

Patients respond differently to inhaled anesthetics as a result of many patient and procedure-related factors, including even hair color (see, e.g., Liem et al., Anesthesiology 101, 279-283, 2004), however, the impact of such differences on the intraoperative period has not been previously investigated. This disclosure shows distinct responses to inhaled anesthetics using a data index. Responses are characterized, in part, by unique MAP trajectories, each associated with its own profile of IOH characteristics. Despite a difference of only 10 points between their average MAP levels (87 vs 77 mmHg), depressed pattern surgeries experienced more than three times the amount of IOH exposure, defined as the proportion of MAP levels below various IOH thresholds and the median number of MAP measurements below 65 mmHg per surgery, compared to elevated pattern surgeries. Individual IOH events that occurred in depressed pattern surgeries resulted in 66% more hypotension exposure per event than those of the elevated pattern. Also, events associated with the depressed pattern were more evenly distributed throughout the first three quarters of the intraoperative period compared to the elevated pattern in which 40% of events occurred within the first quarter alone. Importantly, TVI expression distinguished MAP trajectories for individual procedures and IOH characteristics remained consistent in procedures represented by all three patterns.

Sensitivity to inhaled anesthetics has been the subject of several recently published studies including those related to the triple low state (see, e.g., Kertai et al., Anesthesiology 121, 18-28, 2014; Sessler et al., Anesthesiology 116, 1195-1203, 2012; and Willingham et al., Anesthesiology 123, 775-785, 2015). In each study, the relationship between sensitivity and a postoperative outcome, such as delirium[20], death, and/or excessive length of hospitalization, was evaluated (see, e.g., Kertai et al., Anesthesiology 121, 18-28, 2014; Sessler et al., Anesthesiology 116, 1195-1203, 2012; Willingham et al., Anesthesiology 123, 775-785, 2015; and Fritz, Maybrier, and Avidan, Br J Anaesth 121, 241-248, 2018). The role of inhaled anesthetics in the development of intraoperative hypotension has received far less attention despite their known effects on the cardiovascular system.

Evidence is presented that suggests IOH occurs in a "context-dependent" manner. For a given procedure, surgeries vary in their risk of experiencing IOH events and risk is related to TVI expression. Depressed pattern surgeries exhibited a higher risk of IOH exposure (defined as the proportion of MAP measurements below 65 mmHg) than those of the elevated pattern in more than 98% of all procedures where each TVI pattern occurred in a least 10 surgeries. The total number of IOH events that occur per surgery also appears context dependent. Short duration procedures associated with a high risk of IOH exposure reached the same number of IOH events per surgery as procedures with lower IOH risk but whose duration was much longer. As a result, procedures associated with the depressed expression pattern did not always experience more IOH events per surgery than procedures associated with the other patterns. Neck dissections associated with an elevated pattern, for example, experienced 25% more IOH events per surgery than inguinal hernia repairs associated with the depressed pattern despite the fact the neck dissection procedure carried a lower IOH risk (7.6 vs 11.5% of MAP measurements below 65 mmHg). Taken together, the risk of IOH exposure and the total number of IOH events that occur during surgery likely depend on several factors including a patient's response to inhaled anesthetics and intraoperative duration.

This disclosure differs from the current body of literature in several ways. Like the triple low state studies, MAP, BIS, and MAC data were combined to generate information about surgical patients that goes beyond blood pressure and anesthetic depth monitoring per se. The triple low state was identified and subsequently studied as independent risk factor for postoperative death and excessive length of hospitalization in noncardiac surgery patients (see, e.g., Kertai et al., Anesthesiology 121, 18-28, 2014; Sessler et al., Anesthesiology 116, 1195-1203, 2012; and Willingham et al., Anesthesiology 123, 775-785, 2015). Additionally, the triple low state is narrowly defined according to specific variable thresholds (MAP<75 mmHg, BIS<45, MAC<0.8) so that only a fraction of all available data are used in the model. However, TVI as disclosed herein is used as a tool to measure relative responses to inhaled anesthetics in any adult patient that generated requisite MAP, BIS, and MAC data. TVI data were derived for both cardiac and noncardiac procedures using all available MAP, BIS, and MAC information. TVI expression patterns are not presented as independent risk factors for postoperative outcomes or even intraoperative hypotension. TVI expression is characterized by a host of factors including patient age, severity of comorbidities at the time of surgery (as indicated by ASA physical status), type of procedure, and administered intraoperative medications that likely contribute, singly or in combination, to observed TVI patterns and their associated IOH events.

TVI is clinically valuable by providing a framework to better understand IOH in ways that allow clinicians to better anticipate events and decrease exposure. Numerous studies have demonstrated IOH exposure leads to poor outcomes (see Sessler and Khanna, Intensive Care Med 44, 811-822, 2018), but how exposure differs between patients and procedures has not been previously characterized. Without this information, it remains difficult to anticipate IOH events and reduce exposure. By combining TVI expression and procedure ID, it is possible to distinguish exposure between patients according to characteristics that can help clinicians better anticipate both the number and nature of IOH events. Thus, if TVI expression patterns are identified at the beginning of the intraoperative period, interventional strategies can be implemented that target the specific IOH events expected to occur throughout the remainder of surgery. A machine learning model was recently developed that predicts IOH events[22], however, the model was not developed using the entire intraoperative period and required arterial line MAP monitoring. In contrast, embodiments described herein provide a larger breadth of IOH-related information, apply to the entire intraoperative period, and do not require invasive monitoring.

In conclusion, patients demonstrate markedly different responses to inhaled anesthetics during surgery. These differences deserve renewed consideration due to their clear relationship to IOH exposure. Future studies are needed to validate our findings and evaluate the potential utility of leveraging TVI data to reduce IOH exposure.

In view of the many possible examples to which the principles of the disclosed technology can be applied, it should be recognized that the illustrated examples are only preferred examples and should not be taken as limiting the scope of the disclosed technology. Rather, the scope of the claimed patient matter is defined by the following claims. We claim all such modifications and variations that fall within the scope and spirit of the claims below.

We claim:

1. A method, comprising:
on one or more computer processors having memory attached thereto:
obtaining concurrent measures of mean arterial pressure (MAP), standard minimum alveolar concentration (MAC), and bispectral index (BIS) of a test patient from sequential time intervals during a surgical procedure that comprises administration of an inhalation anesthetic to the test patient;
forming a test data vector characterizing the concurrent MAP, MAC, and BIS measures for the sequential time intervals, comprising normalizing each of the MAP, BIS, and MAC measures of the test patient from the sequential time intervals, summing the normalized MAP, BIS, and MAC measures from each time interval, and forming the test data vector from the respective sums of normalized MAP, BIS, and MAC measures for the sequential time intervals,
performing a K-means clustering procedure of the test data vector with a plurality of reference data vectors, wherein the reference data vectors characterize concurrent MAP, MAC, and BIS measures for sequential time intervals during surgical procedures of reference patients;
identifying a cluster of data vectors including the test data vector; and
outputting a representation of the identified cluster in real-time to a user.

2. The method of claim 1, wherein:
the reference data vectors characterize concurrent MAP, MAC, and BIS measures for sequential time intervals during surgical procedures of reference patients with a known physiological state during and/or following the procedure; and the method further comprises:
determining a prognosis of the test patient based on the known physiological state of the reference patients in the cluster including the test data vector.

3. The method of claim 2, wherein:
the reference data vectors characterize concurrent MAP, MAC, and BIS measures for sequential time intervals during surgical procedures of reference patients with a known post-surgical outcome; and the method comprises:
determining a prognosis of the test patient based on the known post-surgical outcome of reference patients in the cluster including the test data vector.

4. The method of claim 3, wherein the prognosis comprises a likelihood of a level of homeostatic capacity of the test patient following surgery.

5. The method of claim 3, wherein the prognosis comprises a likelihood of one or more post-surgical outcomes comprising one or more of infection, pain, nausea, vomiting, delirium, post-surgical complications, acute kidney injury, respiratory failure, acute anemia, thrombocytopenia, heart failure, coagulopathy, acidosis, malnutrition, sepsis, shock, hospital stay length of greater than average, and death.

6. The method of claim 5, wherein the prognosis comprises a likelihood of death within 30 days or 1 year following surgery.

7. The method of claim 5, wherein the prognosis of post-surgical outcome comprises a likelihood of death within 30 days following surgery.

8. The method of claim 2, further comprising outputting a post-surgical report comprising the prognosis to a user.

9. The method of claim 2, further comprising outputting data representing the prognosis secondary computer system or network.

10. The method of claim 1, comprising monitoring a risk of an intraoperative hypotension event in the test patient during the surgical procedure, wherein:
the reference patients are patients who experienced zero, one, or multiple intraoperative hypotension events during reference surgical procedures comprising administration of an inhalation anesthetic;
the K-means clustering procedure provides clusters of data vectors characterizing relative high, medium, and low concurrent MAP, MAC, and BIS measures; and
the representation of the identified cluster indicates whether the test data vector clusters with the cluster of reference data vectors characterizing the relative high, medium, or low concurrent MAP, MAC, and BIS measures.

11. The method of claim 10, wherein:
clustering of the test data vector with the cluster of reference data vectors characterizing the relative high concurrent MAP, MAC, and BIS measures indicates a low risk of an intraoperative hypotension event; and clustering of the test data vector with the cluster of reference data vectors characterizing the relative low concurrent MAP, MAC, and BIS measures indicates a high risk of an intraoperative hypotension event.

12. The method of claim 11, further comprising preemptively treating the patient for hypotension to reduce the risk of the intraoperative hypotension event if the test data vector clusters with the cluster of reference data vectors characterizing the relative low concurrent MAP, MAC, and BIS measures.

13. The method of claim 1, wherein the intraoperative hypotension event is a MAP measurement of below 65 mmHg.

14. The method of claim 1, wherein the inhalation anesthetic is administered to the test patient as a general anesthetic.

15. The method of claim 1, wherein the concurrent MAP, BIS, and MAC measures are from time intervals during the surgical procedure when the test patient was unconscious due to the inhalation anesthetic.

16. The method of claim 1, wherein the concurrent MAP, BIS, and MAC measures, are normalized by calculating a Z-score for each individual measurement relative to respective reference MAP, BIS, and MAC values.

17. The method of claim 1, wherein the K-means clustering procedure comprises at least three centroids resulting in at least three clusters of data vectors characterizing the concurrent MAP, BIS, and MAC measures, one of which comprises the test data vector.

18. The method of claim 1, wherein the reference patients are from a same hospital system that performed the surgical procedure on the test patient.

19. The method of claim 1, wherein the surgical procedure of the reference patients is the same as the surgical procedure performed on the test patient.

20. The method of claim 1, wherein the surgical procedure comprises ear-nose-throat surgery, trauma surgery, urological surgery, neurosurgery, orthopedic surgery, vascular surgery, thoracic surgery, pediatric surgery, cardiac surgery, OB-GYN surgery, ophthalmologic surgery, transplant surgery, general surgery, plastic surgery, colon and rectal surgery, gynecologic oncology surgery, oral and maxillofacial surgery, critical care procedures comprising inhalation anesthetics, or dental surgical services.

21. The method of claim 1, wherein the sequential time intervals are five minutes in length.

22. The method of claim 1, wherein the concurrent measures of MAP, MAC, and BIS are taken over at least 20 minutes during the surgical procedure.

23. A computing system comprising:
   at least one processor with memory attached thereto;
   wherein the computing system is configured to execute instructions to perform a method according to claim 1.

24. One or more non-transitory computer-readable media storing computer-readable instructions, which, when executed by one or more processors, cause a computer comprising the processors to perform the method of claim 1.

25. The method of claim 1, further comprising storing data representing the identified cluster in a non-transitory computer-readable storage medium.

* * * * *